(12) United States Patent
Wisniewski et al.

(10) Patent No.: US 12,077,752 B2
(45) Date of Patent: *Sep. 3, 2024

(54) NUCLEIC ACID PREPARATION COMPOSITIONS AND METHODS

(71) Applicant: SEQUENOM, INC., San Diego, CA (US)

(72) Inventors: Michele Elizabeth Wisniewski, San Diego, CA (US); William Hang Kwong, San Diego, CA (US); Firouz Mohsenian, San Diego, CA (US); Jian-Hua Ding, San Diego, CA (US)

(73) Assignee: SEQUENOM, INC., San Diego, CA (US)

( * ) Notice: Subject to any disclaimer, the term of this patent is extended or adjusted under 35 U.S.C. 154(b) by 859 days.

This patent is subject to a terminal disclaimer.

(21) Appl. No.: 17/088,000

(22) Filed: Nov. 3, 2020

(65) Prior Publication Data

US 2021/0163920 A1    Jun. 3, 2021

Related U.S. Application Data

(63) Continuation of application No. 16/038,071, filed on Jul. 17, 2018, now Pat. No. 10,858,645, which is a continuation of application No. 15/813,979, filed on Nov. 15, 2017, now Pat. No. 10,053,685, which is a continuation of application No. 15/409,189, filed on Jan. 18, 2017, now Pat. No. 9,850,480, which is a continuation of application No. 14/296,732, filed on Jun. 5, 2014, now Pat. No. 9,580,741, which is a continuation of application No. 13/262,624, filed as application No. PCT/US2010/029653 on Apr. 1, 2010, now Pat. No. 8,771,948.

(60) Provisional application No. 61/166,671, filed on Apr. 3, 2009.

(51) Int. Cl.
*C12N 15/10* (2006.01)
*C12Q 1/68* (2018.01)
*C12Q 1/6834* (2018.01)

(52) U.S. Cl.
CPC ..... *C12N 15/1003* (2013.01); *C12N 15/1006* (2013.01); *C12Q 1/68* (2013.01); *C12Q 1/6834* (2013.01); *Y02A 50/30* (2018.01)

(58) Field of Classification Search
CPC .. C12N 15/1003; C12N 15/1006; C12Q 1/68; C12Q 2565/137; C12Q 2527/125
USPC ............................................. 536/25.4, 25.41
See application file for complete search history.

(56) References Cited

U.S. PATENT DOCUMENTS

| | | |
|---|---|---|
| 4,656,127 A | 4/1987 | Mundy |
| 4,683,195 A | 7/1987 | Mullis et al. |
| 4,683,202 A | 7/1987 | Mullis |
| 4,851,331 A | 7/1989 | Vary et al. |
| 4,965,188 A | 10/1990 | Mullis et al. |
| 5,075,212 A | 12/1991 | Rotbart |
| 5,234,809 A | 8/1993 | Boom et al. |
| 5,346,994 A | 9/1994 | Chomczynski |
| 5,492,806 A | 2/1996 | Drmanac et al. |
| 5,510,328 A | 4/1996 | Polarek et al. |
| 5,525,464 A | 6/1996 | Drmanac et al. |
| 5,547,835 A | 8/1996 | Koester |
| 5,565,340 A | 10/1996 | Chenchik et al. |
| 5,589,330 A | 12/1996 | Shuber |
| 5,605,798 A | 2/1997 | Koester |
| 5,610,284 A | 3/1997 | Ejima et al. |
| 5,656,493 A | 8/1997 | Mullis et al. |
| 5,660,984 A | 8/1997 | Davis et al. |
| 5,674,997 A * | 10/1997 | Woodard ........... C12N 15/1006 536/25.4 |
| 5,679,524 A | 10/1997 | Nikiforov et al. |
| 5,691,141 A | 11/1997 | Koester |
| 5,695,940 A | 12/1997 | Drmanac et al. |
| 5,705,628 A * | 1/1998 | Hawkins ............ C12N 15/1013 536/25.4 |
| 5,786,146 A | 7/1998 | Herman et al. |
| 5,817,798 A | 10/1998 | Gundling |
| 5,834,189 A | 11/1998 | Stevens et al. |
| 5,849,483 A | 12/1998 | Shuber |
| 5,849,542 A | 12/1998 | Reeve et al. |
| 5,851,770 A | 12/1998 | Babon et al. |
| 5,869,242 A | 2/1999 | Kamb |
| 5,876,934 A | 3/1999 | Duthie et al. |
| 5,891,625 A | 4/1999 | Buchardt et al. |
| 5,898,071 A | 4/1999 | Hawkins |
| 5,908,755 A | 6/1999 | Kumar et al. |
| 5,912,118 A | 6/1999 | Ansorge et al. |

(Continued)

FOREIGN PATENT DOCUMENTS

| | | |
|---|---|---|
| EP | 1510577 A1 | 3/2005 |
| EP | 2414545 A2 | 2/2012 |

(Continued)

OTHER PUBLICATIONS

Dhallan et al., JAMA, 2004, 291(9), 1127-1135.*
Office Action dated Aug. 23, 2022 in U.S. Appl. No. 16/849,780, filed Apr. 15, 2020 and published as US-2020-0332279 on Oct. 22, 2020, 8 pages.
U.S. Appl. No. 16/849,780, Non-Final Office Action mailed on May 12, 2023, 12 pages.
Office Action dated Apr. 4, 2022 in U.S. Appl. No. 16/849,780, filed Apr. 15, 2020 and published as US-2020-0332279-A1 on Oct. 22, 2020, 10 pages.

(Continued)

*Primary Examiner* — Ganapathy Krishnan
(74) *Attorney, Agent, or Firm* — LOZA & LOZA LLP; Kari A. Dickinson

(57) ABSTRACT

Provided herein are methods and compositions to extract and enrich by, physical separation or amplification, relatively short nucleic acids from a nucleic acid composition containing a high background of longer nucleic acids (e.g., host or maternal nucleic acids; genomic nucleic acid and the like).

19 Claims, 2 Drawing Sheets

Specification includes a Sequence Listing.

(56) References Cited

U.S. PATENT DOCUMENTS

| | | |
|---|---|---|
| 5,928,906 A | 7/1999 | Koester et al. |
| 5,952,174 A | 9/1999 | Nikiforov et al. |
| 5,958,692 A | 9/1999 | Cotton et al. |
| 5,976,802 A | 11/1999 | Ansorge et al. |
| 5,981,186 A | 11/1999 | Gabe et al. |
| 5,998,143 A | 12/1999 | Ellis et al. |
| 6,004,744 A | 12/1999 | Goelet et al. |
| 6,013,431 A | 1/2000 | Soederlund et al. |
| 6,013,438 A | 1/2000 | Didenko et al. |
| 6,013,499 A | 1/2000 | Narumiya et al. |
| 6,017,702 A | 1/2000 | Lee et al. |
| 6,018,041 A | 1/2000 | Drmanac et al. |
| 6,043,031 A | 3/2000 | Koester et al. |
| 6,045,996 A | 4/2000 | Cronin et al. |
| 6,046,005 A | 4/2000 | Ju et al. |
| 6,087,095 A | 7/2000 | Rosenthal et al. |
| 6,110,684 A | 8/2000 | Kemper et al. |
| 6,136,541 A | 10/2000 | Gulati |
| 6,140,054 A | 10/2000 | Wittwer et al. |
| 6,142,681 A | 11/2000 | Gulati |
| 6,156,501 A | 12/2000 | Mcgall et al. |
| 6,180,778 B1 | 1/2001 | Bastian et al. |
| 6,183,958 B1 | 2/2001 | Stanton, Jr. |
| 6,194,144 B1 | 2/2001 | Koester |
| 6,197,506 B1 | 3/2001 | Fodor et al. |
| 6,210,891 B1 | 4/2001 | Nyren et al. |
| 6,214,560 B1 | 4/2001 | Yguerabide et al. |
| 6,223,127 B1 | 4/2001 | Berno |
| 6,225,625 B1 | 5/2001 | Pirrung et al. |
| 6,229,911 B1 | 5/2001 | Balaban et al. |
| 6,229,991 B1 | 5/2001 | Hietala et al. |
| 6,239,273 B1 | 5/2001 | Pease et al. |
| 6,258,538 B1 | 7/2001 | Koester et al. |
| 6,274,351 B1 | 8/2001 | Peponnet |
| 6,274,726 B1 | 8/2001 | Laugharn, Jr. et al. |
| 6,303,343 B1 | 10/2001 | Kopf-Sill |
| 6,383,393 B1 | 5/2002 | Colpan et al. |
| 6,534,262 B1 | 3/2003 | Mckernan et al. |
| 6,596,480 B1 | 7/2003 | Didenko et al. |
| 6,723,513 B2 | 4/2004 | Lexow |
| 6,777,187 B2 | 8/2004 | Makarov et al. |
| 6,787,307 B1 | 9/2004 | Bitner et al. |
| 7,074,916 B2 | 7/2006 | Bastian et al. |
| 7,129,344 B1 | 10/2006 | Butt et al. |
| 7,169,314 B2 | 1/2007 | Unger et al. |
| 7,208,271 B2 | 4/2007 | Bost et al. |
| 7,226,739 B2 | 6/2007 | Ecker et al. |
| 7,255,992 B2 | 8/2007 | Ecker et al. |
| 7,432,055 B2 | 10/2008 | Pemov et al. |
| 7,482,122 B1 | 1/2009 | Chen |
| 7,683,035 B1 | 3/2010 | Erbacher et al. |
| 8,679,741 B2 | 3/2014 | Hoyal-Wrightson et al. |
| 8,765,652 B2 | 7/2014 | Nelson et al. |
| 8,771,948 B2 * | 7/2014 | Wisniewski ......... C12Q 1/6834 435/91.1 |
| 9,371,556 B2 | 6/2016 | Nelson et al. |
| 9,453,257 B2 | 9/2016 | Hoyal-Wrightson et al. |
| 9,580,741 B2 * | 2/2017 | Wisniewski ....... C12N 15/1006 |
| 9,850,480 B2 * | 12/2017 | Wisniewski ......... C12Q 1/6834 |
| 10,053,685 B2 * | 8/2018 | Wisniewski ....... C12N 15/1006 |
| 10,662,421 B2 | 5/2020 | Hoyal-Wrightson et al. |
| 10,858,645 B2 * | 12/2020 | Wisniewski ....... C12N 15/1003 |
| 2002/0177139 A1 | 11/2002 | Greenfield et al. |
| 2003/0027135 A1 | 2/2003 | Ecker et al. |
| 2003/0044388 A1 | 3/2003 | Dennis et al. |
| 2003/0082539 A1 | 5/2003 | Ecker et al. |
| 2003/0082600 A1 | 5/2003 | Olek et al. |
| 2003/0092045 A1 | 5/2003 | Nargessi et al. |
| 2003/0124556 A1 | 7/2003 | Ecker et al. |
| 2003/0175695 A1 | 9/2003 | Ecker et al. |
| 2003/0175696 A1 | 9/2003 | Ecker et al. |
| 2003/0175697 A1 | 9/2003 | Ecker et al. |
| 2003/0180779 A1 | 9/2003 | Lofton-Day et al. |
| 2003/0190605 A1 | 10/2003 | Ecker et al. |
| 2004/0009518 A1 | 1/2004 | Lo et al. |
| 2004/0086866 A1 | 5/2004 | Chernov et al. |
| 2004/0137449 A1 | 7/2004 | Nargessi |
| 2004/0137470 A1 | 7/2004 | Dhallan |
| 2004/0180328 A1 | 9/2004 | Ecker et al. |
| 2004/0209299 A1 | 10/2004 | Pinter et al. |
| 2004/0219517 A1 | 11/2004 | Ecker et al. |
| 2005/0019769 A1 | 1/2005 | Lenz |
| 2005/0053942 A1 | 3/2005 | Kauppinen et al. |
| 2005/0053986 A1 | 3/2005 | Makarov et al. |
| 2005/0059024 A1 | 3/2005 | Conrad |
| 2005/0112590 A1 | 5/2005 | Boom et al. |
| 2005/0164241 A1 | 7/2005 | Hahn et al. |
| 2005/0175711 A1 | 8/2005 | Kralovec et al. |
| 2005/0287583 A1 | 12/2005 | Smith et al. |
| 2005/0287592 A1 | 12/2005 | Kless |
| 2006/0019278 A1 | 1/2006 | Lo et al. |
| 2006/0024712 A1 | 2/2006 | Baker et al. |
| 2006/0057566 A1 | 3/2006 | Van et al. |
| 2006/0078923 A1 | 4/2006 | McKernan et al. |
| 2006/0177836 A1 | 8/2006 | McKernan et al. |
| 2006/0275773 A1 | 12/2006 | Wangh et al. |
| 2007/0015178 A1 | 1/2007 | Chubinskaya et al. |
| 2007/0048735 A1 | 3/2007 | Ecker et al. |
| 2007/0065853 A1 | 3/2007 | Knoll et al. |
| 2007/0106071 A1 | 5/2007 | Yamashita et al. |
| 2007/0202511 A1 | 8/2007 | Chen et al. |
| 2007/0202525 A1 | 8/2007 | Quake et al. |
| 2008/0003585 A1 | 1/2008 | Ugozzoli |
| 2008/0096191 A1 | 4/2008 | Kauppinen et al. |
| 2008/0124728 A1 | 5/2008 | Baker |
| 2008/0139800 A1 | 6/2008 | Deggerdal et al. |
| 2008/0160528 A1 | 7/2008 | Lorenz |
| 2008/0166703 A1 | 7/2008 | Himmelreich et al. |
| 2008/0293043 A1 | 11/2008 | Hayashizaki et al. |
| 2008/0305479 A1 | 12/2008 | Van Den Boom |
| 2009/0018323 A1 | 1/2009 | Erbacher et al. |
| 2009/0130673 A1 | 5/2009 | Shah et al. |
| 2009/0202984 A1 | 8/2009 | Cantor |
| 2010/0297710 A1 | 11/2010 | Hoyal-wrightson et al. |
| 2012/0178918 A1 | 7/2012 | Wisniewski et al. |
| 2014/0255943 A1 | 9/2014 | Hoyal-Wrightson et al. |
| 2014/0349291 A1 | 11/2014 | Wisniewski et al. |
| 2017/0029807 A1 | 2/2017 | Hoyal-wrightson et al. |
| 2017/0198278 A1 | 7/2017 | Wisniewski et al. |
| 2018/0073010 A1 | 3/2018 | Wisniewski et al. |
| 2019/0010486 A1 | 1/2019 | Wisniewski et al. |
| 2020/0332279 A1 | 10/2020 | Hoyal-wrightson et al. |
| 2021/0163920 A1 | 6/2021 | Wisniewski et al. |

FOREIGN PATENT DOCUMENTS

| | | |
|---|---|---|
| WO | 9118117 A1 | 11/1991 |
| WO | 9737041 A2 | 10/1997 |
| WO | 9820019 A1 | 5/1998 |
| WO | 9929905 A2 | 6/1999 |
| WO | 9958664 A1 | 11/1999 |
| WO | 0052625 A2 | 9/2000 |
| WO | 01/06016 A2 | 1/2001 |
| WO | 0120039 A2 | 3/2001 |
| WO | 0125485 A2 | 4/2001 |
| WO | 0127326 A2 | 4/2001 |
| WO | 0127327 A2 | 4/2001 |
| WO | 0127329 A2 | 4/2001 |
| WO | 0129259 A2 | 4/2001 |
| WO | 03040687 A2 | 5/2003 |
| WO | 2004108925 A1 | 12/2004 |
| WO | 2005012523 A1 | 2/2005 |
| WO | 2005023091 A2 | 3/2005 |
| WO | 2006056480 A2 | 6/2006 |
| WO | 2007069991 A2 | 6/2007 |
| WO | 2007100934 A2 | 9/2007 |
| WO | 2007140417 A2 | 12/2007 |
| WO | 2007147063 A2 | 12/2007 |
| WO | 2009032779 A2 | 3/2009 |
| WO | 2009032781 A2 | 3/2009 |

(56) References Cited

FOREIGN PATENT DOCUMENTS

| WO | 2009091934 A1 | 7/2009 |
|---|---|---|
| WO | 2010115016 A2 | 10/2010 |

OTHER PUBLICATIONS

Definition of Whole Blood by the Free Online Dictionary, Thesaurus and Encyclopedia available at: http://www.thefreedictionary.com/whole+blood, 2005, 3 pages.
IDT (Modified Bases Modifications, attached, available http://www.idtdna.com/site/Catalog/Modifications/Category/7, Jul. 31, 2004, 4 pages.
Applied Biosystems, Transitioning from Standard to Fast PCR on the Applied Biosystems 9800 Fast PCR System, Dec. 1, 2005, 2 pages.
International Preliminary Report on Patentability mailed on Dec. 18, 2008 in International Patent Application No. PCT/US2007/069991, filed on May 30, 2007, 8 pages.
International Preliminary Report on Patentability mailed on Oct. 13, 2011 in International Patent Application No. PCT/US2010/029653, filed on Apr. 1, 2010, 7 pages.
International Search Report and Written Opinion mailed on Dec. 19, 2007 in International Patent Application No. PCT/US2007/069991, filed on May 30, 2007, 14 pages.
International Search Report and Written Opinion mailed on Jan. 31, 2011 in International Patent Application No. PCT/US2010/029653, filed on Apr. 1, 2010, 9 pages.
Office Action dated Apr. 23, 2018 in U.S. Appl. No. 15/813,979, filed Nov. 15, 2017 and published as US 2018-0073010 on Mar. 15, 2018, 7 pages.
Office Action dated Aug. 4, 2020 in U.S. Appl. No. 16/038,071, filed Jul. 17, 2018 and published as US 2019-0010486 on Jan. 10, 2019, 6 pages.
Office Action dated Aug. 9, 2016 in U.S. Appl. No. 14/296,732, filed Jun. 5, 2014 and published as US 2014-0349291 on Nov. 27, 2014, 5 pages.
Office Action dated Aug. 16, 2017 in U.S. Appl. No. 15/409, 189, filed Jan. 18, 2017 and published as US 2017-0198278 on Jul. 13, 2017, 8 pages.
Office Action dated Aug. 29, 2019 in U.S. Appl. No. 15/240,692, filed Aug. 18, 2016 and published as US 2017-0029807 on Feb. 2, 2017, 21 pages.
Office Action dated Dec. 13, 2012 in U.S. Appl. No. 12/301,985, filed Aug. 9, 2010 and published as US 2010-0297710 on Nov. 25, 2010, 19 pages.
Office Action dated Dec. 14, 2017 in U.S. Appl. No. 15/813,979, filed Nov. 15, 2017 and published as US 2018-0073010 on Mar. 15, 2018, 5 pages.
Office Action dated Dec. 18, 2015 in U.S. Appl. No. 14/180,810, filed Feb. 14, 2014 and published as US 2014-0255943 on Sep. 11, 2014, 39 pages.
Office Action dated Feb. 7, 2019 in U.S. Appl. No. 15/240,692, filed Aug. 18, 2016 and published as US 2017-0029807 on Feb. 2, 2017, 22 pages.
Office Action dated Jan. 31, 2020 in U.S. Appl. No. 15/240,692, filed Aug. 18, 2016 and published as US 2017-0029807 on Feb. 2, 2017, 8 pages.
Office Action dated Jul. 16, 2018 in U.S. Appl. No. 15/240,692, filed Aug. 18, 2016 and published as US 2017-0029807 on Feb. 2, 2017, 19 pages.
Office Action dated Jul. 17, 2015 in U.S. Appl. No. 14/180,810, filed Feb. 14, 2014 and published as US 2014-0255943 on Sep. 11, 2014, 28 pages.
Office Action dated Jun. 3, 2013 in U.S. Appl. No. 12/301,985, filed Aug. 9, 2010 and published as US 2010-0297710 on Nov. 25, 2010, 10 pages.
Office Action dated Jun. 6, 2017 in U.S. Appl. No. 15/409,189, filed Jan. 18, 2017 and published as US 2017-0198278 on Jul. 13, 2017, 6 pages.

Office Action dated Mar. 11, 2016 in U.S. Appl. No. 14/296,732, filed Jun. 5, 2014 and published as US 2014-0349291 on Nov. 27, 2014, 6 pages.
Office Action dated Mar. 14, 2014 in U.S. Appl. No. 13/262,624, filed Mar. 1, 2012 and published as US 2012-0178918 on Jul. 12, 2012, 6 pages.
Office Action dated Mar. 19, 2020 in U.S. Appl. No. 16/038,071, filed Jul. 17, 2018 and published as US 2019-0010486 on Jan. 10, 2019, 5 pages.
Office Action dated May 18, 2016 in U.S. Appl. No. 14/180,810, filed Feb. 14, 2014 and published as US 2014-0255943 on Sep. 11, 2014, 9 pages.
Office Action dated Nov. 5, 2013 in U.S. Appl. No. 12/301,985, filed Aug. 9, 2010 and published as US 2010-0297710 on Nov. 25, 2010, 10 pages.
Office Action dated Oct. 11, 2013 in U.S. Appl. No. 13/262,624, filed Mar. 1, 2012 and published as US 2012-0178918 on Jul. 12, 2012, 4 pages.
Office Action dated Oct. 24, 2016 in U.S. Appl. No. 14/296,732, filed Jun. 5, 2014 and published as US 2014-0349291 on Nov. 27, 2014, 5 pages.
PCR* Kits for DNA Ladder Assay, Maxim Biotech, (Cat. #:APO-DNA 1), Feb. 15, 2000, 9 pages.
Allemand et al., "pH-Dependent Specific Binding and Combing of DNA", Biophysical Journal, 1997, 73:2064-2070.
Amicucci et al., "Prenatal Diagnosis of Myotonic Dystrophy Using Fetal DNA Obtained from Maternal Plasma", Clinical Chemistry, 2000, 46:301-302.
Anantha et al., "Porphyrin Binding to Quadruplexed T4G4", Biochemistry, 1998, 37(9):2709-2714.
Anker et al., "Detection of Circulating Tumour DNA in the Blood (Plasma/serum) of Cancer Patients", Cancer and Metastasis Reviews, 1999, 18:65-73.
Anker et al., "Progress in the Knowledge of Circulating Nucleic Acids: Plasma RNA is Particle-Associated. Can it Become a General Detection Marker for a Cancer Blood Test", Clinical Chemistry, 2002, 48(8):1210-1211.
Atamaniuk et al., "Cell-Free Plasma DNA: A Marker for Apoptosis during Hemodialysis", Clinical Chemistry, Mar. 2006, 52(3):523-526.
Beaucage et al., "Deoxynucleoside Phosphoramidites—A New Class of Key Intermediates for Deoxypolynucleotide Synthesis", Tetrahedron Letters, 1981, 22(20):1859-1862.
Birnboim et al., "A Rapid Alkaline Extraction Procedure for Screening Recombinant Plasmid DNA", Nucleic Acids Research, 1979, 7(6):1513-1523.
Bischoff et al., "Cell-Free Fetal DNA and Intact Fetal Cells in Maternal Blood Circulation: Implications for First and Second Trimester Non-Invasive Prenatal Diagnosis", Human Reproduction Update, Nov. 1, 2002, 8(6):493-500.
Bischoff et al., "Cell-Free Fetal DNA in Maternal Blood: Kinetics, Source and Structure", Human Reproduction Update, 2005, 11(1):59-67.
Braslavsky et al., "Sequence Information Can Be Obtained from Single DNA Molecules", PNAS, Jan. 25, 2003, 100(7):3960-3964.
Budelier, "Purification of DNA by Anion-Exchange Chromatography", Current Protocols in Molecular Biology, May 2001, 2(2.1B):8 pages.
Chan et al., "Circulating Nucleic Acids as a Tumor Marker", Histology and Histopathology, 2002, 17:937-943.
Chan et al., "Size Distributions of Maternal and Fetal DNA in Maternal Plasma", Clinical Chemistry, 2004, 50(1):88-92.
Chen et al., "Fluorescence Energy Transfer Detection as a Homogeneous DNA Diagnostic Method", PNAS, Sep. 1997, 94(20):10756-10761.
Chen et al., "Microsatellite Alterations in Plasma DNA of Small Cell Lung Cancer Patients", Nature Medicine, Sep. 1996, 2(9):1033-1035.
Chen et al., "Template-Directed Dye-Terminator Incorporation (TDI) Assay: A Homogeneous DNA Diagnostic Method Based on Fluorescence Resonance Energy Transfer", Nucleic Acids Research, 1997, 25(2):347-353.

(56) References Cited

OTHER PUBLICATIONS

Chiu et al., "Prenatal Exclusion of β Thalassaemia Major by Examination of Maternal Plasma", The Lancet, 2002, 360:998-1000.
Choi et al., "Release of DNA from Dead and Dying Lymphocyte and Monocyte Cell Lines In Vitro", Scandinavian Journal of Immunology, Jul.-Aug. 2004., 60(1-2):159-166.
Clontech et al., "LM-PCR Ladder Assay Kit User Manual", Aug. 17, 2001, 15 pages.
Costa et al., "Automated Assay for Fetal DNA Analysis in Maternal Serum", Clinical Chemistry, 2002, 48(4):679-680.
Costa et al., "First-Trimester Fetal Sex Determination in Maternal Serum Using Real-Time PCR", Prenatal Diagnosis, 2001, 21:1070-1074.
Dear Paul H., "One by One: Single Molecule Tools for Genomics", Briefings in Functional Genomic & Proteomics, Jan. 2003, 1(4):397-416.
Dhallan et al., "Methods to Increase the Percentage of Free Fetal DNA Recovered from Maternal Circulation", JAMA: The Journal of the American Medical Association, Mar. 1, 2004, 291(9):1114-1119.
Didenko et al., "Early Necrotic DNA Degradation-Presence of Blunt-Ended DNA Breaks, 3' and 5' Overhangs in Apoptosis, but only 5' Overhangs in Early Necrosis", American Journal of Pathology, May 2003, 162(5):1571-1578.
Egger et al., "Reverse Transcription Multiplex PCR for Differentiation Between Polio- and Enteroviruses from Clinical and Environmental Samples", Journal of Clinical Microbiology, Jun. 1995, 33(6):1442-1447.
Finning et al., "Prediction of Fetal D Status from Maternal Plasma: Introduction of a New Noninvasive Fetal RHD Genotyping Service", Transfusion, Aug. 2002, 42:1079-1085.
Fournie et al., "Plasma DNA as a Marker of Cancerous Cell Death. Investigations in Patients Suffering from Lung Cancer and in Nude Mice Bearing Human Tumours", Cancer Letters, 1995, 91:221-227.
Fournie et al., "Plasma DNA as Cell Death Marker in Elderly Patients", Gerontology, 1993, 39(4):215-221.
Fucharoen et al., "Prenatal Detection of Fetal Hemoglobin E Gene from Maternal Plasma", Prenatal Diagnosis, 2003, 23:393-396.
Geneclean, "Geneclean: Gel Isolation and Reaction Cleanup", GENECLEAN: Gel Isolation and Reaction Cleanup Information Flyer, QBIOGENE, Inc., 2002, 3 pages.
Gonzalez-Gonzalez et al., "Huntington Disease-Unaffected Fetus Diagnosed from Maternal Plasma Using QF-PCR", Prenatal Diagnosis, 2003, 23:232-234.
Gonzalez-Gonzalez et al., "Prenatal Detection of a Cystic Fibrosis Mutation in Fetal DNA from Maternal Plasma", Prenatal Diagnosis, 2002, 22:946-948.
Goya et al., "Glucocorticoid-Induced Apoptosis in Lymphoid Organs S Associated with a Delayed Increase in Circulating Deoxyribonucleic Acid", Apoptosis, Mar. 2003, 8(2):171-177.
Grompe et al., "Scanning Detection of Mutations in Human Ornithine Transcarbamoylase by Chemical Mismatch Cleavage", PNAS, 1989, 86:5888-5892.
Grompe et al., "The Rapid Detection of Unknown Mutations in Nucleic Acids", Nature Genetics, 1993, 5(2):111-117.
Haase et al., "Detection of Viral Nucleic Acids by In Situ Hybridization", Methods in Virology, 1984, 7:189-226.
Hames et al., "Nucleic Acid Hybridisation: A Practical Approach", IRL Press, 1985, 16 pages.
Harris et al., "Single-Molecule DNA Sequencing of a Viral Genome", Science, Apr. 4, 2008, 320:106-109.
Herzer, "Dna Purification, in Molecular Biology Problem Solver: A Laboratory Guide, Edited by Alan S. Gerstein", Dec. 31, 2001, 7:167-195.
Ikeda et al., "Apoptosis in Cumulus Cells During In vitro Maturation of Bovine Cumulus-Enclosed Oocytes", Reproduction, Jan. 1, 2003, 125:369-376.
Illanes et al., "Cell-free Fetal DNA in Maternal Plasma: An Important Advance to Link Fetal Genetics to Obstetric Ultrasound", Ultrasound in Obstetrics & Gynecology, Apr. 2005, 25(4):317-322.
Imagemaster VDS, "Imaging DNA Agarose Gels Stained with Ethidium Bromide", Amersham Biosciences, Aug. 1996.
Innis et al., "PCR Protocols: A Guide to Methods and Applications", 1990, 7 pages.
Jahr et al., "DNA Fragments in the Blood Plasma of Cancer Patients: Quantitations and Evidence for Their Origin from Apoptotic and Necrotic Cells", Cancer Research, Feb. 15, 2001, 61(4):1659-1665.
Jen, "An Overview on the Isolation and Analysis of Circulating Tumor DNA in Plasma and Serum", Annals of the New York Academy of Sciences Academic journal, Apr. 2000, 906:8-12.
Jurinke et al., "MALDI-TOF Mass Spectrometry: A Versatile Tool for High-Performance DNA Analysis", Molecular Biotechnology, 2004, 26:147-164.
Kalinina et al., "Nanoliter Scale PCR with TaqMan Detection", Nucleic Acids Research, May 15, 1997, 25(10):1999-2004.
Li et al., "Size Separation of Circulatory DNA in Maternal Plasma Permits Ready Detection of Fetal DNA Polymorphisms", Clinical Chemistry, 2004, 50(6):1002-1011.
Li et al., "Whole Genome Amplification of Plasma-Circulating DNA Enables Expanded Screening for Allelic Imbalance in Plasma", The Journal of Molecular Diagnostics, Feb. 2006, 8(1):22-30.
Lichtenstein et al., "Circulating Nucleic Acids and Apoptosis", Annals of the New York Academy of Sciences, Sep. 2001, 945(1):239-249.
Lo et al., "Analysis of Cell-Free Epstein-Barr Virus Associated RNA in the Plasma of Patients with Nasopharyngeal Carcinoma", Clinical Chemistry, 1999, 45:1292-1294.
Lo et al., "Fetal Nucleic Acids in Maternal Plasma", Annals of the New York Academy of Sciences, Aug. 1, 2008, 1137:140-143.
Lo et al., "Plasma DNA as a Prognostic Marker in Trauma Patients", Clinical Chemistry, 2000, 46(3):319-323.
Lo et al., "Prenatal Diagnosis of Fetal RhD Status by Molecular Analysis of Maternal Plasma", The New England Journal of Medicine, 1998, 339:1734-1738.
Lo et al., "Presence of Donor-Specific DNA in Plasma of Kidney and Liver-Transplant Recipients", The Lancet, 1998, 351:1329-1330.
Lo et al., "Presence of Fetal DNA in Maternal Plasma and Serum", The Lancet, 1997, 350(9076):485-487.
Lo et al., "Quantitative Analysis of Fetal DNA in Maternal Plasma and Serum: Implications for Noninvasive Prenatal Diagnosis", American Journal of Human Genetics, Apr. 1, 1998, 62(4):768-775.
Lo et al., "Rapid Clearance of Fetal DNA from Maternal Plasma", American Journal of Human Genetics, 1999, 64:218-224.
Lo et al., "Recent Advances in Fetal Nucleic Acids in Maternal Plasma", Journal of Histochemistry and Cytochemistry, Mar. 2005, 53(3):293-296.
Margulies et al., "Genome Sequencing in Microfabricated High-density Picolitre Reactors", Nature, Sep. 15, 2005, 437(7057):376-380.
Mirvana Mirna et al., "Instruction Manual", mirVana miRNA Isolation Kit, Ambion, 2006, 30 pages.
Nagata et al., "Apoptotic DNA Fragmentation", Experimental Cell Research (2000), 2000, 256(1):12-18.
Nakano et al., "Single-Molecule PCR Using Water-in-Oil Emulsion", Journal of Biotechnology, Apr. 24, 2003, 102(2):117-124.
Nawroz et al., "Microsatellite Alterations in Serum DNA of Head and Neck Cancer Patients", Nature Medicine, Sep. 1996, 2(9):1035-1037.
Needham-Vandevanter et al., "Characterization of an Adduct Between CC-1065 and a Defined Oligodeoxynucleotide Duplex", Nucleic Acids Research, 1984, 12(15):6159-6168.
Ng et al., "mRNA of Placental Origin Is Readily Detectable in Maternal Plasma", PNAS, 2003, 100(8):4748-4753.
Nolte Frederick S., "Branched DNA Signal Amplification for Direct Quantitation of Nucleic Acid Sequences in Clinical Specimens", Advanced Clinical Chemistry, 1998, 33:201-235.

(56) References Cited

OTHER PUBLICATIONS

Oeth et al., "iPLEX™ Assay: Increased Plexing Efficiency and Flexibility for MassARRAY® System Through Single Base Primer Extension with Mass-Modified Terminators", iPLEX Assay, 2005, 12 pages.
Orita et al., "Detection of Polymorphisms of Human DNA by Gel Electrophoresis as Single-Strand Conformation Polymorphisms", PNAS, 1989, 86:2766-2770.
Pearson et al., "High-Performance Anion-Exchange Chromatography of Oligonucleotides", Journal of Chromatography, 1983, 255:137-149.
Pichl et al., "Magnetic Bead Technology in Viral RNA and DNA Extraction from Plasma Minipools", Transfusion, Jul. 2005, 45:1106-1110.
Qiagen, "For DNA Purification from Whole Blood, Plasma, Serum, Buffy Coat, Body Fluids, Lymphocytes, Cultured Cells, Tissue, Swabs, Dried Blood Spots", Qiagen QIAamp DNA Mini Kit and QIAamp DNA Blood Mini Kit Handbook, Sep. 2001, 68 pages.
Qiagen, "For Simultaneous Purification of Genomic DNA and Total RNA from the Same Animal Cell or Tissue Sample", Qiagen AllPrep DNA/RNA Mini Handbook, Nov. 2005, 3-55.
Qu et al., "Analysis of Drug-DNA Binding Data", Methods Enzymology, 2000, 321:353-369.
Rijnders et al., "Fetal Sex Determination from Maternal Plasma in Pregnancies at Risk for Congenital Adenal Hyperplasia", Obstetrics & Gynecology, 2001, 98:374-378.
Romero et al., "PCR Detection of the Human Enteroviruses", Diagnostic Molecular Microbiology, Principles and Applications, 1993, 401-406.
Rumore et al., "Endogenous Circulating DNA in Systemic Lupus Erythematosus", Journal of Clinical Investigation, Jul. 1990, 86(1):69-74.
Saito et al., "Prenatal DNA Diagnosis of a Single-gene Disorder from Maternal Plasma", Lancet, Sep. 30, 2000, 356:1170.
Saiyed et al., "Application of Magnetic Techniques in the Field of Drug Discovery and Biomedicine", BioMagnetic Research and Technology, 2003, 1:1-18.
Sambrook et al., "Molecular Cloning: A Laboratory Manual", Molecular Cloning: A Laboratory Manual, 2001, 3(10):52 pages.
Schmidt et al., "Detection and Direct Genomic Sequencing of Multiple Rare Unknown Flanking DNA in Highly Complex Samples", Human Gene Therapy, May 1, 2001, 12(7):743-749.
Sheffield et al., "Identification of Novel Rhodopsin Mutations Associated with Retinitis Pigmentosa by GC-clamped Denaturing Gradient Gel Electrophoresis", Proceedings of the National Academy of Sciences, 1991, 49:699-706.
Shiels et al., "MagneSil, C'est Magnifique!", Promega Notes, 2001, 79:22-24.
Singer et al., "Optimization of In Situ Hybridization Using Isotopic and Non-Isotopic Detection Methods", Biotechniques, 1986, 4:230-250.
Slor et al., "A New Assay of Deoxyribonucleases Using as a Substrate Radioactively Labeled DNA Bound Either Directly or Through Anti-DNA Antibodies to Plastic Depression Plates", Nucleic Acids Research, 1975, 2(5):745-756.
Soni et al., "Progress Toward Ultrafast DNA Sequencing Using Solid-State Nanopores", Clinical Chemistry, Nov. 2007, 53(11):1996-2001.
Staley et al., "Apoptotic DNA Fragmentation Is Detected by a Semiquantitative Ligation-Mediated PCR of Blunt DNA Ends", Cell Death & Differentiation, Jan. 1997, 4(1):66-75.
Struass William M., "Current Protocols in Molecular Biology", John Wiley & Sons, N.Y., 1993, 6.3.1-6.3.6.
Stroun et al., "About the Possible Origin and Mechanism of Circulating DNA Apoptosis and Active DNA Release", Clinica Chimica Acta, Nov. 2001, 313(1-2):139-142.
Stroun et al., "Neoplastic Characteristics of the DNA found in the Plasma of Cancer Patients", Oncology, 1989, 46:318-322.
Su et al., "Removal of High-Molecular-Weight DNA by Carboxylated Magnetic Beads Enhances the Detection of Mutated K-Ras DNA in Urine", Annals of the New York Academy of Sciences, New York Academy of Sciences, US, Aug. 1, 2008, 1137:82-91.
Thermofisher, "Sodium Acetate Precipitation of Small Nucleic Acids", available at https://www.thermofisher.com/us/en/home/references/protocols/nucleic-acid-purification-and-analysis/dna-protocol/sodium-acetate-precipitation-of-small-nucleic-acids.html, Mar. 18, 2005, 2 pages.
Thomas et al., "Hybridization of Denatured RNA and Small DNA Fragments Transferred to Nitrocellulose", PNAS, 1980, 77(9):5201-5205.
Vaickus et al., "Immune Markers in Hematologic Malignancies", Critical Reviews in Oncology/Hematology, Dec. 1991, 11(4):267-297.
Van Der Hel, "Quality and Quantity of DNA Isolated from Frozen Urine in Population-Based Research", Analytical Biochemistry, May 15, 2002, 304(2):206-11.
Venter et al., "The Sequence of the Human Genome", Science, Feb. 16, 2001, 291(5507):1304-1351.
Vincent et al., "Helicase-Dependent Isothermal DNA Amplification", EMBO Reports, 2004, 5(8):795-800.
Vogelstein et al., "Digital PCR", PNAS, Aug. 3, 1999, 96(16):9236-9241.
Vogelstein et al., "Preparative and Analytical Purification of DNA from Agarose", PNAS, 1979, 76(2):615-619.
Wang et al., "Preferential Isolation of Fragmented DNA Enhances the Detection of Circulating Mutated K-Ras DNA", Clinical Chemistry, Jan. 2004, 50(1):211-213.
White et al., "Detecting Single Base Substitutions as Heteroduplex Polymorphisms", Genomics, Feb. 1992, 12:301-306.
Widlak et al., "Cleavage Preferences of the Apoptotic Endonuclease DFF40 (Caspase-activated Dnase or Nuclease) on Naked DNA and Chromatin Substrates", The Journal of Biological Chemistry, Mar. 17, 2000, 275(11):8226-8232.
Xu et al., "Immobilization of DNA on an Aluminum(III) Alkanebisphosphonate Thin Film with Electrogenerated Chemiluminescent Detection", Journal of American Chemical Society, 1994, 116(18):8386-8387.
U.S. Appl. No. 14/180,810, Notice of Allowance mailed on Aug. 17, 2016, 3 pages.
U.S. Appl. No. 15/240,692, Advisory Action mailed on May 23, 2019, 3 pages.
U.S. Appl. No. 15/240,692, Notice of Allowability mailed on Mar. 25, 2020, 3 pages.
U.S. Appl. No. 16/849,780, Advisory Action mailed on Jan. 17, 2023, 4 pages.
U.S. Appl. No. 16/849,780, Notice of Allowance mailed on Sep. 20, 2023, 7 pages.

* cited by examiner

NUCLEIC ACID PREPARATION COMPOSITIONS AND METHODS

RELATED PATENT APPLICATION(S)

This application is a continuation of U.S. patent application Ser. No. 16/038,071, filed on Jul. 17, 2018, entitled NUCLEIC ACID PREPARATION COMPOSITIONS AND METHODS, naming Michele Elizabeth Wsniewski, William Hang Kwong, Firouz Mohsenian, and Jian-Hua Ding as inventors, and designated by, which is a continuation of U.S. patent application Ser. No. 15/813,979, now U.S. Pat. No. 10,053,685, filed on Nov. 15, 2017, entitled NUCLEIC ACID PREPARATION COMPOSITIONS AND METHODS, naming Michele Elizabeth Wisniewski, William Hang Kwong, Firouz Mohsenian, and Jian-Hua Ding as inventors, and designated by, which is a continuation of U.S. patent application Ser. No. 15/409,189, now U.S. Pat. No. 9,850,480, filed on Jan. 18, 2017, entitled NUCLEIC ACID PREPARATION COMPOSITIONS AND METHODS, naming Michele Elizabeth Wisniewski, William Hang Kwong, Firouz Mohsenian, and Jian-Hua Ding as inventors, and designated by, which is a continuation application of U.S. patent application Ser. No. 14/296,732, filed on Jun. 5, 2014, now U.S. Pat. No. 9,580,741, entitled NUCLEIC ACID PREPARATION COMPOSITIONS AND METHODS, naming Michele Elizabeth Wisniewski, William Hang Kwong, Firouz Mohsenian, and Jian-Hua Ding as inventors, and designated by, which is a continuation application of U.S. patent application Ser. No. 13/262,624, now U.S. Pat. No. 8,771,948, filed on Mar. 1, 2012, entitled NUCLEIC ACID PREPARATION COMPOSITIONS AND METHODS, naming Michele Elizabeth Wisniewski, William Hang Kwong, Firouz Mohsenian, and Jian-Hua Ding as applicants and inventors, and designated by, which is a national stage of international patent application number PCT/US2010/029653 filed on Apr. 1, 2010, entitled NUCLEIC ACID PREPARATION COMPOSITIONS AND METHODS, naming Michele Elizabeth Wisniewski, William Hang Kwong, Firouz Mohsenian, and Jian-Hua Ding as applicants and inventors, and designated by, which claims the benefit of U.S. provisional patent application No. 61/166,671 filed on Apr. 3, 2009, entitled NUCLEIC ACID PREPARATION COMPOSITIONS AND METHODS, naming Michele Elizabeth Wisniewski, William Hang Kwong, Firouz Mohsenian, and Jian-Hua Ding as inventors and designated by. The entire contents of the foregoing patent applications are incorporated herein by reference, including, without limitation, all text, tables and drawings.

SEQUENCE LISTING

The instant application contains a Sequence Listing which has been submitted electronically in ASCII format and is hereby incorporated by reference in its entirety. Said ASCII copy, created on Jul. 28, 2014, is named SEQ-6026-CT_SL.txt and is 9,028 bytes in size.

FIELD OF THE TECHNOLOGY

The technology relates in part to compositions and methods for nucleic acid preparation and enrichment.

BACKGROUND

The isolation and subsequent amplification of nucleic acids play a central role in molecular biology. Isolated, purified nucleic acids may be used, inter alia, as a starting material for diagnosis and prognosis of diseases or disorders. Therefore, the isolation of nucleic acids, particularly by non-invasive means, is of particular importance for use in genetic analyses.

Current methods for the extraction of nucleic acids include the use of organic-based methods (e.g., phenol/chloroform/isoamyl alcohol), or capitalize upon ion interaction of nucleic acids in an aqueous solution (e.g., salting out in combination with alcohol, solution pH and temperature) alone or in combination with anion exchange chromatography or cation exchange chromatography. Organic-based methods employ the use of phenol/chloroform/isoamyl alcohol or variations thereof for isolating DNA, but have serious disadvantages, namely the processes are very time-consuming, require considerable experimental effort, and are associated with an acute risk of exposure to toxic substances to those carrying out the isolation. Chromatography-based methods increase flexibility and automation since these methods can be used in combination with multiple matrices (e.g., membranes, latex, magnetic beads, micro-titer plate, etc.) and in the presence or absence of ligands (e.g., DEAE, silica, acrylamide, etc.). However, these methods are better suited to extract larger strands of nucleic acids to ensure greater success in downstream analysis.

Previously, the recovery of smaller, fragmented nucleic acids from biological samples was considered unimportant, and extraction methods were designed to isolate large, undegraded nucleic acid molecules. Recently, however, it is shorter base pair nucleic acids (e.g., highly degraded RNA or mRNA and apoptotic DNA) that have been shown to be highly informative for a wide range of applications, including prenatal diagnostics and the study of apoptotic DNA from host or non-host sources.

SUMMARY

The present technology provides improved nucleic acid preparation compositions and methods suitable for enrichment, isolation and analysis of relatively short nucleic acid species targets, sometimes found in cell free or substantially cell free biological compositions containing mixed compositions (e.g., viral nucleic acid in host background, fetal nucleic acid in maternal background, mixed nucleic acid populations from environmental samples, and the like), and often associated with various disease conditions or apoptotic cellular events (e.g., cancers and cell proliferative disorders, prenatal or neonatal diseases, genetic abnormalities, and programmed cell death events). The relatively short nucleic acid species targets, which can represent degraded or fractionated nucleic acids, can also be used for haplotyping and genotyping analysis, such as fetal genotyping for example.

Methods and compositions described herein are useful for size selection of nucleic acids, in a simple, cost effective manner that also can be compatible with automated and high throughput processes and apparatus. Methods and compositions provided herein are useful for enriching or extracting a target nucleic acid from a cell free or substantially cell free biological composition containing a mixture of non-target nucleic acids, based on the size of the nucleic acid, where the target nucleic acid is of a different size, and often is smaller, than the non-target nucleic acid.

Thus provided in some embodiments is a method for enriching relatively short nucleic acid from a nucleic acid composition, which comprises, (a) contacting nucleic acid of a nucleic acid composition with a solid phase under association conditions, wherein: (i) the nucleic acid of the nucleic acid composition comprises relatively short nucleic acid and relatively long nucleic acid, (ii) the relatively short nucleic acid is about 300 base pairs or less, and (iii) the relatively long nucleic acid is larger than about 300 base pairs; whereby the relatively short nucleic acid and the relatively long nucleic acid are associated with the solid phase; (b) introducing the solid phase after (a) to dissociation conditions that comprise a volume exclusion agent and a salt, wherein: (i) the salt is not a chaotropic salt, and (ii) the relatively short nucleic acid preferentially dissociates from the solid phase under the dissociation conditions as compared to the relatively long nucleic, thereby yielding dissociated nucleic acid; and (c) separating the dissociated nucleic acid from the solid phase, whereby the relatively short nucleic acid is enriched in the dissociated nucleic acid relative to the relatively long nucleic acid in the nucleic acid composition. In some embodiments, the dissociated nucleic acid comprises ribonucleic acid (RNA), and in certain embodiments consists essentially of RNA. In some embodiments, the dissociated nucleic acid comprises deoxyribonucleic acid (DNA), and in certain embodiments consists essentially of DNA.

In some embodiments, about 30% to about 90% of the nucleic acid of the nucleic acid composition associates with the solid phase. In certain embodiments, about 60% of the nucleic acid of the nucleic acid composition associates with the solid phase. In some embodiments, the method further comprises washing the solid phase after (a). In certain embodiments, the solid phase is washed under conditions that remove material of the nucleic acid composition not associated with the solid phase from the solid phase. In some embodiments, the solid phase is washed under conditions that dissociate any non-nucleic acid material of the nucleic acid composition from the solid phase. In certain embodiments, the wash comprises an alcohol solution.

In some embodiments, the association conditions comprise a C1-C6 alkyl alcohol, and in certain embodiments the association conditions consist essentially of a C1-C6 alkyl alcohol. In certain embodiments, the association conditions do not comprise a C1-C6 alkyl alcohol. In some embodiments, the alcohol comprises ethanol. In some embodiments, the association conditions comprise a salt. In certain embodiments, the salt comprises a chaotropic salt, an ionic salt or combination thereof. In some embodiments using ionic salts or a combination of salts, the ionic salt is sodium chloride. In certain embodiments, the association conditions consist essentially of a salt. In some embodiments, the association conditions do not comprise a salt. In some embodiments, the association conditions do not comprise a chaotropic agent (e.g., no chaotropic salt).

In certain embodiments, the association conditions comprise a volume exclusion agent. In some embodiments, the association conditions consist essentially of a volume exclusion agent. In certain embodiments, the volume exclusion agent comprises a polyalkyl alcohol (e.g., polyalkyl glycol or polyethylene glycol), dextran, Ficoll, polyvinyl pyrollidone or combination thereof. In some embodiments, the polyalkyl alcohol is polyethylene glycol (PEG), and in certain embodiments the PEG is PEG 8000. In some embodiments, the association conditions do not comprise a volume exclusion agent. In some embodiments, the association conditions do not comprise polyethylene glycol.

In some embodiments, the dissociation conditions comprise about 0.25M to about 0.5M of the ionic salt. In certain embodiments, the dissociation conditions comprise about 10% PEG. In some embodiments, the salt and the volume exclusion agent are present in the dissociation conditions at concentrations according to Table 1 (presented below in Example 3). In some embodiments, the dissociation conditions do not comprise a chaotropic agent (e.g., no chaotropic salt). In certain embodiments, the relatively short nucleic acid preferentially dissociates from the solid phase under the association conditions as compared to the relatively long nucleic acid at a ratio of about 1.05 to about 5 relatively short nucleic acid to relatively long nucleic acid. In certain embodiments, the relatively short nucleic acid is enriched about 10% to about 45% in the dissociated nucleic acid relative to in the nucleic acid composition.

In some embodiments, the solid phase is paramagnetic and the dissociated nucleic acid is separated from the solid phase by a magnet or magnetic field. In certain embodiments, the solid phase is separated from the dissociated nucleic acid by centrifugation. In certain embodiments, the solid phase is not paramagnetic. In some embodiments, the solid phase is separated from the dissociated nucleic acid by transferring the dissociated nucleic acid to an environment that does not contain the solid phase used in (a) of the method described above. In certain embodiments, the solid phase is separated from the dissociated nucleic acid by transferring the solid phase to an environment that does not contain the dissociated nucleic acid. In certain embodiments, the environment is a vessel. The term "vessel" as used herein, refers to any container, plate (e.g., multiwell plate), tube, and the like, suitable for carrying out the methods described herein.

In some embodiments, the method further comprises associating the dissociated nucleic acid to a second solid phase. In certain embodiments, the method further comprises dissociating the dissociated nucleic acid from the second solid phase, thereby releasing the dissociated nucleic acid from the second solid phase. In some embodiments, the method further comprises analyzing the dissociated nucleic acid and/or nucleic acid associated with the solid phase after (c) by mass spectrometry. In certain embodiments, the method further comprises contacting the dissociated nucleic acid and/or nucleic acid associated with the solid phase after (c) with an oligonucleotide that hybridizes to the dissociated nucleic acid and is extended under extension conditions, thereby yielding extended oligonucleotide.

In some embodiments, the method further comprises amplifying the dissociated nucleic acid and/or the nucleic acid associated with the solid phase after (c), thereby yielding amplified product. In certain embodiments, the method further comprises contacting the amplified product with an oligonucleotide that hybridizes to the amplified product and is extended under extension conditions, thereby yielding extended oligonucleotide. In some embodiments, the method further comprises analyzing the extended oligonucleotide or the amplified product. In certain embodiments, the extended oligonucleotide or the amplified product is analyzed by mass spectrometry.

In some embodiments, the nucleic acid composition is a biological composition. In certain embodiments, the biological composition is a substantially cell-free biological composition. In certain embodiments, the nucleic acid is cell free nucleic acid. In some embodiments, the substantially cell free biological composition is from a pregnant female. In certain embodiments, the pregnant female is in the first trimester of pregnancy. In some embodiments, the substantially cell-free biological composition is blood plasma and in certain embodiments the substantially cell-free biological composition is blood serum. In certain embodiments, the substantially cell-free biological composition is urine.

In some embodiments, the method further comprises detecting the presence or absence of fetal nucleic acid, and in some embodiments comprises detecting the presence or absence of a fetal-specific nucleotide sequence. In certain embodiments, the fetal-specific nucleotide sequence is a Y-chromosome sequence. In some embodiments, the fetal-specific nucleotide sequence is a mRNA sequence. In some embodiments, the fetal-specific nucleotide sequence is labeled. In certain embodiments, the method further comprises quantifying the labeled fetal-specific nucleotide sequence. In certain embodiments, the method further comprises detecting the presence or absence of a prenatal disorder. In some embodiments, the prenatal disorder is a chromosome abnormality. In certain embodiments, the chromosome abnormality is a trisomy. In some embodiments, the trisomy is trisomy 21, trisomy 18, trisomy 13 or combination thereof. In certain embodiments, the method further comprises detecting the presence or absence of a cell proliferation disorder. In some embodiments, the cell proliferation disorder is a cancer.

Certain embodiments are described further in the following description, examples, claims and drawings.

BRIEF DESCRIPTION OF THE DRAWINGS

The drawings illustrate embodiments of the technology and are not limiting. For clarity and ease of illustration, the drawings are not made to scale and, in some instances, various aspects may be shown exaggerated or enlarged to facilitate an understanding of particular embodiments.

FIG. 1A shows the results of sample nucleic acid association to solid support followed by dissociation to illustrate the size distribution of fragments in the sample. FIG. 1B shows the results of elution of nucleic acids from the solid support after an initial size selection was performed and the initially eluted fragments were separated from the material still bound to the solid support. The initial size selection dissociates the smaller fragments (shown in FIG. 1C), leaving behind larger fragments, according to the salt concentration used. FIG. 1C illustrates the size distribution of the nucleic acids initially dissociated, according to the dissociation conditions given above each gel lane.

In FIG. 2, "short" fragment refers to DNA fragments less than the designated cutoff size provided, for example, less than 500 base pairs at 0.375M NaCl/10% PEG, less than 400 base pairs at 0.5M NaCl/10% PEG, and less than 300 base pairs at 1M NaCl/10% PEG.

DETAILED DESCRIPTION

Figure 1C:
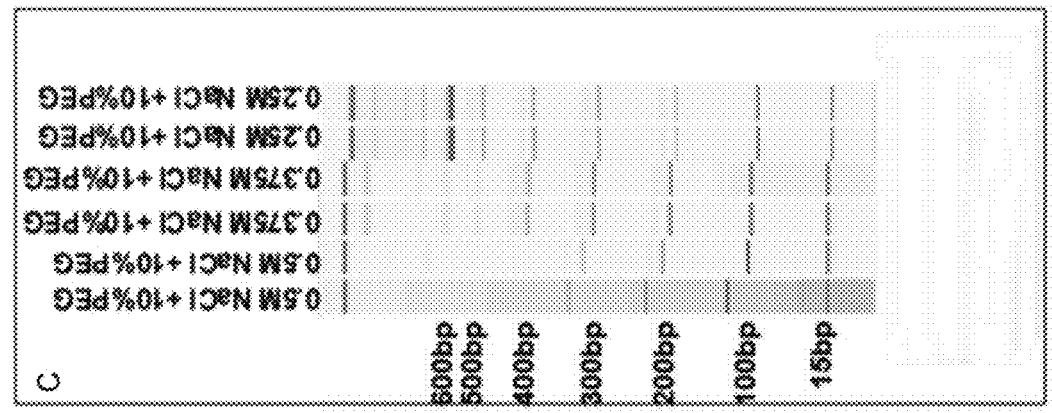
FIGS. 1A, 1B and 1C illustrate the results of gel electrophoresis of nucleic acids, in a 1-kilobase size ladder, extracted or enriched after association and size selective dissociation of nucleic acids.

The presence of cell-free nucleic acid in peripheral blood is a well established phenomenon. While cell-free nucleic acid may originate from several sources, it has been demonstrated that one source of circulating extracellular nucleic acid originates from programmed cell death, also known as apoptosis. The source of nucleic acid that arise as a result of apoptosis may be found in many body fluids and originate from several sources, including, but not limited to, normal programmed cell death in the host, induced programmed cell death in the case of an autoimmune disease, septic shock, neoplasms (malignant or non-malignant), or non-host sources such as an allograft (transplanted tissue), or the fetus or placenta of a pregnant woman. The applications for the detection, extraction and relative enrichment of extracellular nucleic acid from peripheral blood or other body fluids are widespread and may include inter alia, non-invasive prenatal diagnosis, cancer diagnostics, pathogen detection, autoimmune response and allograft rejection.

In some embodiments, methods and compositions are provided that enable enrichment and/or extraction of relatively short target nucleic acid fragments, of specific size ranges (e.g., 50-500 nucleotides or base pairs, and more specifically 50 to 200 nucleotides or base pairs, for example, and herein referred to as "target" or "sample" nucleic acid), contained within a nucleic acid composition of mixed fragment sizes (e.g., 1 to 100,000 nucleotides or base pairs (bp), or more). The enrichment and/or extraction of the target nucleic acid can be accomplished by a partial, or complete, physical separation of the target nucleic acid from the rest of the nucleic acid in the nucleic acid composition. More specifically, the methods and compositions described herein, are useful for the selective extraction and relative enrichment, based on size discrimination, of nucleic acids of in the range of about 50 to about 500 nucleotides or base pairs, and more specifically about 50 to about 200 nucleotides or base pairs, in a high background of genomic nucleic acids (herein referred to as "non-target" nucleic acid). The methods and compositions described herein lead to a relatively enriched fraction of nucleic acids that has a higher concentration of smaller nucleic acids, where the smaller nucleic acids sometimes contain target nucleic acids. In some embodiments, further enrichment of the specific target nucleic acids can be accomplished by amplification of the specific size selected target nucleic acid sequences using amplification procedures known in the art or described below.

Disorders

Nucleic acid prepared using methods and compositions described herein can be utilized to detect the presence or absence of one or more prenatal or neonatal disorders. Non-limiting examples of prenatal and neonatal disorders include achondroplasia, Angelman syndrome, Cockayne syndrome, cystic fibrosis (autosomal recessive), congenital adrenal hyperplasia (autosomal recessive), DiGeorge syndrome, Duchenne's muscular dystrophy, (X-linked recessive), hemophilia A (X-linked recessive), alpha- and beta-thalassemia (autosomal recessive), fragile X syndrome (X-linked dominant), polycystic kidney disease (adult type; autosomal dominant), sickle cell anemia (autosomal recessive), Marfan syndrome, Prader-Wlli syndrome, Waardenburg syndrome, Tay-Sachs disease (autosomal) and the like.

A prenatal or neonatal disorder in some embodiments is a chromosome abnormality. In certain embodiments chromosome abnormalities include, without limitation, a gain or loss of an entire chromosome or a region of a chromosome comprising one or more genes. Chromosome abnormalities include monosomies, trisomies, polysomies, loss of heterozygosity, deletions and/or duplications of one or more nucleotide sequences (e.g., one or more genes), including deletions and duplications caused by unbalanced translocations in some embodiments. The terms "aneuploidy" and "aneuploid" as used herein refer to an abnormal number of chromosomes in cells of an organism. As different organisms have widely varying chromosome complements, the term "aneuploidy" does not refer to a particular number of chromosomes, but rather to the situation in which the chromosome content within a given cell or cells of an organism is abnormal.

The term "monosomy" as used herein refers to lack of one chromosome of the normal complement. Partial monosomy can occur in unbalanced translocations or deletions, in which only a portion of the chromosome is present in a single copy (see deletion (genetics)). Monosomy of sex chromosomes (45, X) causes Turner syndrome.

The term "disomy" refers to the presence of two copies of a chromosome. For organisms such as humans that have two copies of each chromosome (those that are diploid or "euploid"), it is the normal condition. For organisms that normally have three or more copies of each chromosome (those that are triploid or above), disomy is an aneuploid chromosome complement. In uniparental disomy, both copies of a chromosome come from the same parent (with no contribution from the other parent).

The term "trisomy" refers to the presence of three copies, instead of the normal two, of a particular chromosome. The presence of an extra chromosome 21, which is found in Down syndrome, is called trisomy 21. Trisomy 18 and Trisomy 13 are the two other autosomal trisomies recognized in live-born humans. Trisomy of sex chromosomes can be seen in females (47, XXX) or males (47, XXY which is found in Klinefelter's syndrome; or 47,XYY).

The terms "tetrasomy" and "pentasomy" as used herein refer to the presence of four or five copies of a chromosome, respectively. Although rarely seen with autosomes, sex chromosome tetrasomy and pentasomy have been reported in humans, including)(XXX, XXXY, XXYY, XYYY, XXXXX, XXXXY, XXXYY, XXYYY and XYYYY.

Chromosome abnormalities can be caused by a variety of mechanisms. Mechanisms include, but are not limited to (i) nondisjunction occurring as the result of a weakened mitotic checkpoint, (ii) inactive mitotic checkpoints causing nondisjunction at multiple chromosomes, (iii) merotelic attachment occurring when one kinetochore is attached to both mitotic spindle poles, (iv) a multipolar spindle forming when more than two spindle poles form, (v) a monopolar spindle forming when only a single spindle pole forms, and (vi) a tetraploid intermediate occurring as an end result of the monopolar spindle mechanism.

The terms "partial monosomy" and "partial trisomy" as used herein refer to an imbalance of genetic material caused by loss or gain of part of a chromosome. A partial monosomy or partial trisomy can result from an unbalanced translocation, where an individual carries a derivative chromosome formed through the breakage and fusion of two different chromosomes. In this situation, the individual would have three copies of part of one chromosome (two normal copies and the portion that exists on the derivative chromosome) and only one copy of part of the other chromosome involved in the derivative chromosome.

The term "mosaicism" as used herein refers to aneuploidy in some cells, but not all cells, of an organism. Certain chromosome abnormalities can exist as mosaic and non-mosaic chromosome abnormalities. For example, certain trisomy 21 individuals have mosaic Down syndrome and some have non-mosaic Down syndrome. Different mechanisms can lead to mosaicism. For example, (i) an initial zygote may have three 21st chromosomes, which normally would result in simple trisomy 21, but during the course of cell division one or more cell lines lost one of the 21st chromosomes; and (ii) an initial zygote may have two 21st chromosomes, but during the course of cell division one of the 21st chromosomes were duplicated. Somatic mosaicism most likely occurs through mechanisms distinct from those typically associated with genetic syndromes involving complete or mosaic aneuploidy. Somatic mosaicism has been identified in certain types of cancers and in neurons, for example. In certain instances, trisomy 12 has been identified in chronic lymphocytic leukemia (CLL) and trisomy 8 has been identified in acute myeloid leukemia (AML). Also, genetic syndromes in which an individual is predisposed to breakage of chromosomes (chromosome instability syndromes) are frequently associated with increased risk for various types of cancer, thus highlighting the role of somatic aneuploidy in carcinogenesis. Methods and kits described herein can identify presence or absence of non-mosaic and mosaic chromosome abnormalities.

Following is a non-limiting list of chromosome abnormalities that can be potentially identified by methods and kits described herein.

| Chromosome | Abnormality | Disease Association |
|---|---|---|
| X | XO | Turner's Syndrome |
| Y | XXY | Klinefelter syndrome |
| Y | XYY | Double Y syndrome |
| Y | XXX | Trisomy X syndrome |
| Y | XXXX | Four X syndrome |
| Y | Xp21 deletion | Duchenne's/Becker syndrome, congenital adrenal hypoplasia, chronic granulomatus disease |
| Y | Xp22 deletion | steroid sulfatase deficiency |
| Y | Xq26 deletion | X-linked lymph proliferative disease |
| 1 | 1p (somatic) monosomy trisomy | neuroblastoma |
| 2 | monosomy trisomy 2q | growth retardation, developmental and mental delay, and minor physical abnormalities |
| 3 | monosomy trisomy (somatic) | Non-Hodgkin's lymphoma |
| 4 | monosomy trisomy (somatic) | Acute non lymphocytic leukemia (ANLL) |
| 5 | 5p | Cri du chat; Lejeune syndrome |
| 5 | 5q (somatic) monosomy trisomy | myelodysplastic syndrome |
| 6 | monosomy trisomy (somatic) | clear-cell sarcoma |

-continued

| Chromosome | Abnormality | Disease Association |
|---|---|---|
| 7 | 7q11.23 deletion | William's syndrome |
| 7 | monosomy | trisomy monosomy 7 syndrome of childhood; somatic: renal cortical adenomas; myelodysplastic syndrome |
| 8 | 8q24.1 deletion | Langer-Giedon syndrome |
| 8 | monosomy trisomy | myelodysplastic syndrome; Warkany syndrome; somatic: chronic myelogenous leukemia |
| 9 | monosomy 9p | Alfi's syndrome |
| 9 | monosomy 9p partial trisomy | Rethore syndrome |
| 9 | trisomy | complete trisomy 9 syndrome; mosaic trisomy 9 syndrome |
| 10 | Monosomy trisomy (somatic) | ALL or ANLL |
| 11 | 11p- | Aniridia; Wilms tumor |
| 11 | 11q- | Jacobson Syndrome |
| 11 | monosomy (somatic) trisomy | myeloid lineages affected (ANLL, MDS) |
| 12 | monosomy trisomy (somatic) | CLL, Juvenile granulosa cell tumor (JGCT) |
| 13 | 13q- | 13q-syndrome; Orbeli syndrome |
| 13 | 13q14 deletion | retinoblastoma |
| 13 | monosomy trisomy | Patau's syndrome |
| 14 | monosomy trisomy (somatic) | myeloid disorders (MDS, ANLL, atypical CML) |
| 15 | 15q11-q13 deletion monosomy | Prader-Willi, Angelman's syndrome |
| 15 | trisomy (somatic) | myeloid and lymphoid lineages affected, e.g., MDS, ANLL, ALL, CLL) |
| 16 | 16q13.3 deletion | Rubenstein-Taybi |
| | monosomy trisomy (somatic) | papillary renal cell carcinomas (malignant) |
| 17 | 17p-(somatic) | 17p syndrome in myeloid malignancies |
| 17 | 17q11.2 deletion | Smith-Magenis |
| 17 | 17q13.3 | Miller-Dieker |
| 17 | monosomy trisomy (somatic) | renal cortical adenomas |
| 17 | 17p11.2-12 trisomy | Charcot-Marie Tooth Syndrome type 1; HNPP |
| 18 | 18p- | 18p partial monosomy syndrome or Grouchy Lamy Thieffry syndrome |
| 18 | 18q- | Grouchy Lamy Salmon Landry Syndrome |
| 18 | monosomy trisomy | Edwards Syndrome |
| 19 | monosomy trisomy | |
| 20 | 20p- | trisomy 20p syndrome |
| 20 | 20p11.2-12 deletion | Alagille |
| 20 | 20q- | somatic: MDS, ANLL, polycythemia vera, chronic neutrophilic leukemia |
| 20 | monosomy trisomy (somatic) | papillary renal cell carcinomas (malignant) |
| 21 | monosomy trisomy | Down's syndrome |
| 22 | 22q11.2 deletion | DiGeorge's syndrome, velocardiofacial syndrome, conotruncal anomaly face syndrome, autosomal dominant Opitz G/BBB syndrome, Caylor cardiofacial syndrome |
| 22 | monosomy trisomy | complete trisomy 22 syndrome |

In certain embodiments, presence or absence of a fetal chromosome abnormality is identified (e.g., trisomy 21, trisomy 18 and/or trisomy 13). In some embodiments, presence or absence of a chromosome abnormality related to a cell proliferation condition or cancer is identified. Presence or absence of one or more of the chromosome abnormalities described in the table above may be identified in some embodiments.

In some embodiments, a prenatal or neonatal condition is a cell proliferation condition. Cell proliferation conditions include, without limitation, cancers of the colorectum, breast, lung, liver, pancreas, lymph node, colon, prostate, brain, head and neck, skin, liver, kidney, and heart. Examples of cancers include hematopoietic neoplastic disorders, which are diseases involving hyperplastic/neoplastic cells of hematopoietic origin (e.g., arising from myeloid, lymphoid or erythroid lineages, or precursor cells thereof). The diseases can arise from poorly differentiated acute leukemias, e.g., erythroblastic leukemia and acute megakaryoblastic leukemia. Additional myeloid disorders include, but are not limited to, acute promyeloid leukemia (APML), acute myelogenous leukemia (AML) and chronic myelogenous leukemia (CML) (reviewed in Vaickus, Crit. Rev. in Oncol./Hemotol. 11:267-297 (1991)); lymphoid malignancies include, but are not limited to acute lymphoblastic leukemia (ALL), which includes B-lineage ALL and T-lineage ALL, chronic lymphocytic leukemia (CLL), prolymphocytic leukemia (PLL), hairy cell leukemia (HLL) and Waldenstrom's macroglobulinemia (WM). Additional forms of malignant lymphomas include, but are not limited to non-Hodgkin lymphoma and variants thereof, peripheral T cell lymphomas, adult T cell leukemia/lymphoma (ATL), cutaneous T-cell lymphoma (CTCL), large granular lymphocytic leukemia (LGF), Hodgkin's disease and Reed-Sternberg disease. In a particular embodiment, a cell proliferative disorder is non-endocrine tumor or endocrine tumors. Illustrative examples of non-endocrine tumors include but are not limited to adenocarcinomas, acinar cell carcinomas, adenosquamous carcinomas, giant cell tumors, intraductal papillary mucinous neoplasms, mucinous cystadenocarcinomas, pancreatoblastomas, serous cystadenomas, solid and pseudopapillary tumors. An endocrine tumor may be an islet cell tumor.

Cell proliferative conditions also include inflammatory conditions, such as inflammation conditions of the skin, including, for example, eczema, discoid lupus erythematosus, lichen planus, lichen sclerosus, mycosis fungoides, photodermatoses, pityriasis rosea, psoriasis. Also included are cell proliferative conditions related to obesity, such as proliferation of adipocytes, for example.

Cell proliferative conditions also include viral diseases, including for example, Acquired Immunodeficiency Syndrome, Adenoviridae Infections, Alphavirus Infections, Arbovirus Infections, Borna Disease, Bunyaviridae Infections, Caliciviridae Infections, Chickenpox, Coronaviridae Infections, Coxsackievirus Infections, Cytomegalovirus Infections, Dengue, DNA Virus Infections, Ecthyma, Contagious, Encephalitis, Arbovirus, Epstein-Barr Virus Infections, Erythema Infectiosum, Hantavirus Infections, Hemorrhagic Fevers, Viral, Hepatitis, Viral, Human, Herpes Simplex, Herpes Zoster, Herpes Zoster Oticus, Herpesviridae Infections, Infectious Mononucleosis, Influenza in Birds, Influenza, Human, Lassa Fever, Measles, Molluscum Contagiosum, Mumps, Paramyxoviridae Infections, Phlebotomus Fever, Polyomavirus Infections, Rabies, Respiratory Syncytial Virus Infections, Rift Valley Fever, RNA Virus Infections, Rubella, Slow Virus Diseases, Smallpox, Subacute Sclerosing Panencephalitis, Tumor Virus Infections, Warts, West Nile Fever, Virus Diseases and Yellow Fever. For example, Large T antigen of the SV40 transforming virus acts on UBF, activates it and recruits other viral proteins to Pol I complex, and thereby stimulates cell proliferation to promote virus propagation.

Cell proliferative conditions also include cardiac conditions resulting from cardiac stress, such as hypertension, balloon angioplasty, valvular disease and myocardial infarction. For example, cardiomyocytes are differentiated muscle cells in the heart that constitute the bulk of the ventricle wall, and vascular smooth muscle cells line blood vessels. Although both are muscle cell types, cardiomyocytes and vascular smooth muscle cells vary in their mechanisms of contraction, growth and differentiation. Cardiomyocytes become terminally differentiated shortly after heart formation and thus lose the capacity to divide, whereas vascular smooth muscle cells are continually undergoing modulation from the contractile to proliferative phenotype. Under various pathophysiological stresses such as hypertension, balloon angioplasty, valvular disease and myocardial infarction, for example, the heart and vessels undergo morphologic growth-related alterations that can reduce cardiac function and eventually manifest in heart failure. Cell proliferative conditions also include conditions related to angiogenesis (e.g., cancers) and obesity caused by proliferation of adipocytes and other fat cells.

In some embodiments, methods and compositions described herein can be used to extract cell-free nucleic acids from biological samples, from animals or humans for example, for the purpose of detecting or diagnosing a disease condition (e.g., cancer, genetic abnormality, and the like). In certain embodiments, the biological sample is from a human, who also may be a cancer patient in certain embodiments. Methods and compositions described herein may be used in conjunction with any method known to elevate nucleic acids (e.g., nucleotide sequences) associated with cancer conditions, from sample nucleic acid compositions (e.g., patient samples). Alternatively, methods and compositions described herein may be used in conjunction with any method known to decrease nucleic acid sequences associated with cancer conditions, from in sample nucleotide compositions.

Nucleic Acids

Target or sample nucleic acid may be derived from one or more samples or sources. "Sample nucleic acid" as used herein refers to a nucleic acid from a sample. "Target nucleic acid" and "template nucleic acid" are used interchangeably throughout the document and refer to a nucleic acid of interest. The terms "total nucleic acid" or "nucleic acid composition" as used herein, refer to the entire population of nucleic acid species from or in a sample or source. Non-limiting examples of nucleic acid compositions containing "total nucleic acids" include, host and non-host nucleic acid, maternal and fetal nucleic acid, genomic and acellular nucleic acid, or mixed-population nucleic acids isolated from environmental sources. As used herein, "nucleic acid" refers to polynucleotides such as deoxyribonucleic acid (DNA) and ribonucleic acid (RNA), and refers to derivatives, variants and analogs of RNA or DNA made from nucleotide analogs, single (sense or antisense) and double-stranded polynucleotides. The term "nucleic acid" does not refer to or infer a specific length of the polynucleotide chain, thus nucleotides, polynucleotides, and oligonucleotides are also included within "nucleic acid."

In some embodiments, target nucleic acid is relatively short and may comprise fragments in the of about 5 to about 500 nucleotides or base pairs, for example. In certain embodiments, the target nucleic acid can be in the range of about 5 to about 300 nucleotides or base pairs. In certain embodiments, the relatively short target nucleic acid can be in the range of about 5 to about 200 nucleotides or base pairs. That is, target nucleic acids can be about 10, 15, 20, 25, 30, 35, 40, 45, 50, 55, 60, 65, 70, 75, 80, 85, 90, 95, 100, 110, 120, 130, 140, 150, 160, 170, 180, 190, 200, 210, 220, 230 250, 300, 350, 400, 450, or up to about 500 nucleotides or base pairs in length. In certain embodiments, the relatively long nucleic acid can be greater than about 200 nucleotides or base pairs. The term "nucleotides", as used herein, in reference to the length of nucleic acid chain, refers to a single stranded nucleic acid chain. The term "base pairs", as used herein, in reference to the length of nucleic acid chain, refers to a double stranded nucleic acid chain.

Deoxyribonucleotides include deoxyadenosine, deoxycytidine, deoxyguanosine and deoxythymidine. For RNA, the uracil base is uridine. A source or sample containing sample nucleic acid(s) may contain one or a plurality of sample nucleic acids. A plurality of sample nucleic acids as described herein refers to at least 2 sample nucleic acids and includes nucleic acid sequences that may be identical or different. That is, the sample nucleic acids may all be representative of the same nucleic acid sequence, or may be representative of two or more different nucleic acid sequences (e.g., from 1, 2, 3, 4, 5, 6, 7, 8, 9, 10, 11, 12, 13, 14, 15, 16, 17, 18, 19, 20, 50, 100, 1000 or more sequences).

A sample containing nucleic acids may be collected from an organism, mineral or geological site (e.g., soil, rock, mineral deposit, combat theater), forensic site (e.g., crime scene, contraband or suspected contraband), or a paleontological or archeological site (e.g., fossil, or bone) for example. A sample may be a "biological sample," which refers to any material obtained from a living source or formerly-living source, for example, an animal such as a human or other mammal, a plant, a bacterium, a fungus, a protist or a virus. The biological sample can be in any form, including without limitation a solid material such as a tissue, cells, a cell pellet, a cell extract, or a biopsy, or a biological fluid such as urine, blood, saliva, amniotic fluid, exudate from a region of infection or inflammation, or a mouth wash containing buccal cells, urine, cerebral spinal fluid and synovial fluid and organs.

The biological sample can be maternal blood, including maternal plasma or serum. In some circumstances, the biological sample is acellular. In other circumstances, the biological sample does contain cellular elements or cellular remnants in maternal blood. Other biological samples include amniotic fluid, chorionic villus sample, biopsy material from a pre-implantation embryo, maternal urine, maternal saliva, a celocentesis sample, fetal nucleated cells or fetal cellular remnants, or the sample obtained from washings of the female reproductive tract. In some embodiments, a biological sample may be blood.

As used herein, the term "blood" encompasses whole blood or any fractions of blood, such as serum and plasma as conventionally defined. Blood plasma refers to the fraction of whole blood resulting from centrifugation of blood treated with anticoagulants. Blood serum refers to the watery portion of fluid remaining after a blood sample has coagulated. Fluid or tissue samples often are collected in accordance with standard protocols hospitals or clinics generally follow. For blood, an appropriate amount of peripheral blood (e.g., between 3-40 milliliters) often is collected and can be stored according to standard procedures prior to further preparation in such embodiments. A fluid or tissue sample from which template nucleic acid is extracted may be acellular. In some embodiments, a fluid or tissue sample may contain cellular elements or cellular remnants. In some embodiments, the nucleic acid composition containing the target nucleic acid or nucleic acids may be collected from a cell free or substantially cell free biological composition, blood plasma, blood serum or urine for example.

The term "substantially cell free" as used herein, refers to biologically derived preparations or compositions that contain a substantially small number of cells, or no cells. A preparation intended to be completely cell free, but containing cells or cell debris can be considered substantially cell free. That is, substantially cell free biological preparations can include up to about 50 cells or fewer per milliliter of preparation (e.g., up to about 50 cells per milliliter or less, 45 cells per milliliter or less, 40 cells per milliliter or less, 35 cells per milliliter or less, 30 cells per milliliter or less, 25 cells per milliliter or less, 20 cells per milliliter or less, 15 cells per milliliter or less, 10 cells per milliliter or less, 5 cells per milliliter or less, or up to about 1 cell per milliliter or less).

For prenatal applications of technology described herein, fluid or tissue sample may be collected from a female at a gestational age suitable for testing, or from a female who is being tested for possible pregnancy. Suitable gestational age may vary depending on the chromosome abnormality tested. In certain embodiments, a pregnant female subject sometimes is in the first trimester of pregnancy, at times in the second trimester of pregnancy, or sometimes in the third trimester of pregnancy. In certain embodiments, a fluid or tissue is collected from a pregnant woman at 1-4, 4-8, 8-12, 12-16, 16-20, 20-24, 24-28, 28-32, 32-36, 36-40, or 40-44 weeks of fetal gestation, and sometimes between 5-28 weeks of fetal gestation.

Target and/or total nucleic acid can be extracellular nucleic acid in certain embodiments. The term "extracellular nucleic acid" as used herein refers to nucleic acid isolated from a source having substantially no cells (e.g., no detectable cells, or fewer than 50 cells per milliliter or less as described above, or may contain cellular elements or cellular remnants). Examples of acellular sources for extracellular nucleic acid are blood plasma, blood serum and urine. Without being limited by theory, extracellular nucleic acid may be a product of cell apoptosis and cell breakdown, which provides basis for extracellular nucleic acid often having a series of lengths across a large spectrum (e.g., a "ladder"). In some embodiments, the nucleic acids can be cell free nucleic acid.

Extracellular template nucleic acid can include different nucleic acid species. For example, blood serum or plasma from a person having cancer can include nucleic acid from cancer cells and nucleic acid from non-cancer cells. In another example, blood serum or plasma from a pregnant female can include maternal nucleic acid and fetal nucleic acid. In some instances, fetal nucleic acid sometimes is about 5% to about 40% of the overall template nucleic acid (e.g., about 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38 or 39% of the template nucleic acid is fetal nucleic acid). In some embodiments, the majority of fetal nucleic acid in template nucleic acid is of a length of about 500 base pairs or less (e.g., about 80, 85, 90, 91, 92, 93, 94, 95, 96, 97, 98, 99 or 100% of fetal nucleic acid is of a length of about 500 base pairs or less).

The amount of fetal nucleic acid (e.g., concentration) in template nucleic acid sometimes is determined. In certain embodiments, the amount of fetal nucleic acid is determined according to markers specific to a male fetus (e.g., Y-chromosome STR markers (e.g., DYS 19, DYS 385, DYS 392 markers); RhD marker in RhD-negative females), or according to one or more markers specific to fetal nucleic acid and not maternal nucleic acid (e.g., fetal RNA markers in maternal blood plasma; Lo, 2005, Journal of Histochemistry and Cytochemistry 53 (3): 293-296). The amount of fetal nucleic acid in extracellular template nucleic acid can be quantified and utilized for the identification of the presence or absence of a chromosome abnormality in certain embodiments.

In some embodiments, extracellular nucleic acid can be enriched or relatively enriched for fetal nucleic acid, using methods described herein alone, or in conjunction with other methods known in the art. Non-limiting examples of additional methods known in the art for enriching a sample for a particular species of nucleic acid are described in; PCT Patent Application Number PCT/US07/69991, filed May 30, 2007, PCT Patent Application Number PCT/US2007/071232, filed Jun. 15, 2007, U.S. Provisional Application Nos. 60/968,876 and 60/968,878, and PCT Patent Application Number PCT/EP05/012707, filed Nov. 28, 2005, herein incorporated by reference in their entirety. In certain embodiments, maternal nucleic acid can be selectively removed (partially, substantially, almost completely or completely) from the sample.

A sample also may be isolated at a different time point as compared to another sample, where each of the samples may be from the same or a different source. A sample nucleic acid may be from a nucleic acid library, such as a cDNA or RNA library, for example. A sample nucleic acid may be a result of nucleic acid purification or isolation and/or amplification of nucleic acid molecules from the sample. Sample nucleic acid provided for sequence analysis processes described herein may contain nucleic acid from one sample or from two or more samples (e.g., from 1, 2, 3, 4, 5, 6, 7, 8, 9, 10, 11, 12, 13, 14, 15, 16, 17, 18, 19 or 20 samples).

Sample nucleic acid may comprise or consist essentially of any type of nucleic acid suitable for use with processes of the technology, such as sample nucleic acid that can hybridize to solid phase nucleic acid (described hereafter), for example. A sample nucleic in certain embodiments can comprise or consist essentially of DNA (e.g., complementary DNA (cDNA), genomic DNA (gDNA) and the like), RNA (e.g., message RNA (mRNA), short inhibitory RNA (siRNA), microRNA, ribosomal RNA (rRNA), tRNA and the like), and/or DNA or RNA analogs (e.g., containing base analogs, sugar analogs and/or a non-native backbone and the like). A nucleic acid can be in any form useful for conducting processes herein (e.g., linear, circular, supercoiled, single-stranded, double-stranded and the like). A nucleic acid may be, or may be from, a plasmid, phage, autonomously replicating sequence (ARS), centromere, artificial chromosome, chromosome, a cell, a cell nucleus or cytoplasm of a cell in certain embodiments. A sample nucleic acid in some embodiments is from a single chromosome (e.g., a nucleic acid sample may be from one chromosome of a sample obtained from a diploid organism).

Sample nucleic acid may be provided for conducting methods described herein without processing of the sample(s) containing the nucleic acid in certain embodiments. In some embodiments, sample nucleic acid is provided for conducting methods described herein after processing of the sample(s) containing the nucleic acid. For example, a sample nucleic acid may be extracted, isolated, purified or amplified from the sample(s). The term "isolated" as used herein refers to nucleic acid removed from its original environment (e.g., the natural environment if it is naturally occurring, or a host cell if expressed exogenously), and thus is altered "by the hand of man" from its original environment. An isolated nucleic acid generally is provided with fewer non-nucleic acid components (e.g., protein, lipid) than the amount of components present in a source sample. A composition comprising isolated sample nucleic acid can be substantially isolated (e.g., about 90%, 91%, 92%, 93%, 94%, 95%, 96%, 97%, 98%, 99% or greater than 99% free of non-nucleic acid components). The term "purified" as used herein refers to sample nucleic acid provided that contains fewer nucleic acid species than in the sample source from which the sample nucleic acid is derived. A composition comprising sample nucleic acid may be substantially purified (e.g., about 90%, 91%, 92%, 93%, 94%, 95%, 96%, 97%, 98%, 99% or greater than 99% free of other nucleic acid species). The term "amplified" as used herein refers to subjecting nucleic acid of a sample to a process that linearly or exponentially generates amplicon nucleic acids having the same or substantially the same nucleotide sequence as the nucleotide sequence of the nucleic acid in the sample, or portion thereof.

Sample nucleic acid also may be processed by subjecting nucleic acid to a method that generates nucleic acid fragments, in certain embodiments, before providing sample nucleic acid for a process described herein. In some embodiments, sample nucleic acid subjected to fragmentation or cleavage may have a nominal, average or mean length of about 5 to about 10,000 base pairs, about 100 to about 1,000 base pairs, about 100 to about 500 base pairs, or about 10, 15, 20, 25, 30, 35, 40, 45, 50, 55, 60, 65, 70, 75, 80, 85, 90, 95, 100, 200, 300, 400, 500, 600, 700, 800, 900, 1000, 2000, 3000, 4000, 5000, 6000, 7000, 8000, 9000 or 10000 base pairs. Fragments can be generated by any suitable method known in the art, and the average, mean or nominal length of nucleic acid fragments can be controlled by selecting an appropriate fragment-generating procedure by the person of ordinary skill. In certain embodiments, sample nucleic acid of a relatively shorter length can be utilized to analyze sequences that contain little sequence variation and/or contain relatively large amounts of known nucleotide sequence information. In some embodiments, sample nucleic acid of a relatively longer length can be utilized to analyze sequences that contain greater sequence variation and/or contain relatively small amounts of unknown nucleotide sequence information.

Sample nucleic acid fragments often contain overlapping nucleotide sequences, and such overlapping sequences can facilitate construction of a nucleotide sequence of the previously non-fragmented sample nucleic acid, or a portion thereof. For example, one fragment may have subsequences x and y and another fragment may have subsequences y and z, where x, y and z are nucleotide sequences that can be 5 nucleotides in length or greater. Overlap sequence y can be utilized to facilitate construction of the x-y-z nucleotide sequence in nucleic acid from a sample. Sample nucleic acid may be partially fragmented (e.g., from an incomplete or terminated specific cleavage reaction) or fully fragmented in certain embodiments.

Sample nucleic acid can be fragmented by various methods known to the person of ordinary skill, which include without limitation, physical, chemical and enzymic processes. Examples of such processes are described in U.S. Patent Application Publication No. 20050112590 (published on May 26, 2005, entitled "Fragmentation-based methods and systems for sequence variation detection and discovery," naming Van Den Boom et al.). Certain processes can be selected by the person of ordinary skill to generate non-specifically cleaved fragments or specifically cleaved fragments. Examples of processes that can generate non-specifically cleaved fragment sample nucleic acid include, without limitation, contacting sample nucleic acid with apparatus that expose nucleic acid to shearing force (e.g., passing nucleic acid through a syringe needle; use of a French press); exposing sample nucleic acid to irradiation (e.g., gamma, x-ray, UV irradiation; fragment sizes can be controlled by irradiation intensity); boiling nucleic acid in water (e.g., yields about 500 base pair fragments) and exposing nucleic acid to an acid and base hydrolysis process. Sample nucleic acid may be specifically cleaved by contacting the nucleic acid with one or more specific cleavage agents. The term "specific cleavage agent" as used herein refers to an agent, sometimes a chemical or an enzyme that can cleave a nucleic acid at one or more specific sites. Specific cleavage agents often will cleave specifically according to a particular nucleotide sequence at a particular site.

Examples of enzymic specific cleavage agents include without limitation endonucleases (e.g., DNase (e.g., DNase I, II); RNase (e.g., RNase E, F, H, P); Cleavase™ enzyme; Taq DNA polymerase; E. coli DNA polymerase I and eukaryotic structure-specific endonucleases; murine FEN-1 endonucleases; type I, II or III restriction endonucleases such as Acc I, Afl III, Alu I, Alw44 I, Apa I, Asn I, Ava I, Ava II, BamH I, Ban II, Bcl I, Bgl I. Bgl II, Bln I, Bsm I, BssH II, BstE II, Cfo I, Cla I, Dde I, Dpn I, Dra I, EcIX I, EcoR I, EcoR I, EcoR II, EcoR V, Hae II, Hae II, Hind II, Hind III, Hpa I, Hpa II, Kpn I, Ksp I, Mlu I, MluN I, Msp I, Nci I, Nco I, Nde I, Nde II, Nhe I, Not I, Nru I, Nsi I, Pst I, Pvu I, Pvu II, Rsa I, Sac I, Sal I, Sau3A I, Sca I, ScrF I, Sfi I, Sma I, Spe I, Sph I, Ssp I, Stu I, Sty I, Swa I, Taq I, Xba I, Xho I.); glycosylases (e.g., uracil-DNA glycolsylase (UDG), 3-methyladenine DNA glycosylase, 3-methyladenine DNA glycosylase II, pyrimidine hydrate-DNA glycosylase, FaPy-DNA glycosylase, thymine mismatch-DNA glycosylase, hypoxanthine-DNA glycosylase, 5-Hydroxymethyluracil DNA glycosylase (HmUDG), 5-Hydroxymethylcytosine DNA glycosylase, or 1,N6-etheno-adenine DNA glycosylase); exonucleases (e.g., exonuclease III); ribozymes, and DNAzymes. Sample nucleic acid may be treated with a chemical agent, or synthesized using modified nucleotides, and the modified nucleic acid may be cleaved. In non-limiting examples, sample nucleic acid may be treated with (i) alkylating agents such as methylnitrosourea that generate several alkylated bases, including N3-methyladenine and N3-methylguanine, which are recognized and cleaved by alkyl purine DNA-glycosylase; (ii) sodium bisulfite, which causes deamination of cytosine residues in DNA to form uracil residues that can be cleaved by uracil N-glycosylase; and (iii) a chemical agent that converts guanine to its oxidized form, 8-hydroxyguanine, which can be cleaved by formamidopyrimidine DNA N-glycosylase. Examples of chemical cleavage processes include without limitation alkylation, (e.g., alkylation of phosphorothioate-modified nucleic acid); cleavage of acid lability of P3'-N5'-phosphoroamidate-containing nucleic acid; and osmium tetroxide and piperidine treatment of nucleic acid.

As used herein, the term "complementary cleavage reactions" refers to cleavage reactions that are carried out on the same sample nucleic acid using different cleavage reagents or by altering the cleavage specificity of the same cleavage reagent such that alternate cleavage patterns of the same target or reference nucleic acid or protein are generated. In certain embodiments, sample nucleic acid may be treated with one or more specific cleavage agents (e.g., 1, 2, 3, 4, 5, 6, 7, 8, 9, 10 or more specific cleavage agents) in one or more reaction vessels (e.g., sample nucleic acid is treated with each specific cleavage agent in a separate vessel).

Sample nucleic acid also may be exposed to a process that modifies certain nucleotides in the nucleic acid before providing sample nucleic acid for a method described herein. A process that selectively modifies nucleic acid based upon the methylation state of nucleotides therein can be applied to sample nucleic acid. The term "methylation state" as used herein refers to whether a particular nucleotide in a polynucleotide sequence is methylated or not methylated. Methods for modifying a target nucleic acid molecule in a manner that reflects the methylation pattern of the target nucleic acid molecule are known in the art, as exemplified in U.S. Pat. No. 5,786,146 and U.S. patent publications 20030180779 and 20030082600. For example, non-methylated cytosine nucleotides in a nucleic acid can be converted to uracil by bisulfite treatment, which does not modify methylated cytosine. Non-limiting examples of agents that can modify a nucleotide sequence of a nucleic acid include methylmethane sulfonate, ethylmethane sulfonate, diethylsulfate, nitrosoguanidine (N-methyl-N'-nitro-N-nitrosoguanidine), nitrous acid, di-(2-chloroethyl)sulfide, di-(2-chloroethyl)methylamine, 2-aminopurine, t-bromouracil, hydroxylamine, sodium bisulfite, hydrazine, formic acid, sodium nitrite, and 5-methylcytosine DNA glycosylase. In addition, conditions such as high temperature, ultraviolet radiation, x-radiation, can induce changes in the sequence of a nucleic acid molecule.

Sample nucleic acid may be provided in any form useful for conducting a sequence analysis or manufacture process described herein, such as solid or liquid form, for example. In certain embodiments, sample nucleic acid may be provided in a liquid form optionally comprising one or more other components, including without limitation one or more buffers or salts selected by the person of ordinary skill.

Solid Supports

The term "solid support" or "solid phase" as used herein refers to an insoluble material with which nucleic acid can be associated, and the terms can be used interchangeably. Examples of solid supports for use with processes described herein include, without limitation, chips, flat surfaces filters, one or more capillaries and/or fibers, arrays, filters, beads, beads (e.g., paramagnetic beads, magnetic beads, microbeads, nanobeads) and particles (e.g., microparticles, nanoparticles). Beads and/or particles may be free or in connection with one another (e.g., sintered). In some embodiments, the solid phase can be a collection of particles. In certain embodiments, the particles can comprise silica, and the silica may comprise silica dioxide. In some embodiments the silica can be porous, and in certain embodiments the silica can be non-porous. In some embodiments, the particles further comprise an agent that confers a paramagnetic property to the particles. In certain embodiments, the agent comprises a metal, and in certain embodiments the agent is a metal oxide, (e.g., iron or iron oxides, where the iron oxide contains a mixture of $Fe^{2+}$ and $Fe^{3+}$). Magnetically responsive silica dioxide beads can be obtained commercially. Non-limiting examples of magnetically responsive silica beads are; DynaL® beads (Invitrogen, Carlsbad, California), SiMag® beads (Chemicell, Berlin, Germany), MagAttract® beads (Qiagen, Hilden, Germany), Magnesil® beads (Promega, Madison, Wisconsin), and functional magnetic silica beads (MoBiTec, Gottingen, Germany; Microspheres-Nanospheres.com (a division of Corpuscular, Inc) Lincolndale, New York; G. Kisker Biotech, Steinfurt, Germany).

In some embodiments, the solid phase does not comprise a functional group that interacts with the nucleic acid. In certain embodiments, the solid phase does not comprise a carboxy functional group. In some embodiments, the solid phase has a net charge. In certain embodiments, the net charge is positive, and sometimes the net charge is negative.

Nucleic acids may reversibly associate with a solid support (e.g., magnetic silica dioxide particles) under association conditions. The association may be reversed under dissociation conditions, and all or a subset of nucleic acid associated with the solid phase may dissociate from the solid phase under the dissociation conditions. The term "associate" as used herein refers to an interaction between a nucleic acid and a solid phase, which interaction often is non-covalent, often is adsorption, sometimes is absorption, often is binding, and generally is reversible. The term "association conditions" as used herein, refers to conditions under which nucleic acid from a nucleic acid composition is associated with a solid support. In some embodiments, nucleic acid of substantially all sizes in the composition associates with a solid support under the association conditions. Sometimes, substantially all of the nucleic acid in a composition associates with a solid support, and sometimes about 30 percent to about 100 percent of the nucleic acid, from the total nucleic acid in a sample, associates or binds to the solid support (e.g., 30% or greater, 35% or greater, 40% or greater, 45% or greater, 50% or greater, 55% or greater, 60% or greater, 65% or greater, 70% or greater, 75% or greater, 80% or greater, 85% or greater, 90% or greater, 95% or greater, or 99% or greater of the total nucleic acid present in a sample associates with the solid phase).

In some embodiments, association conditions can include one or more of the following: salts, alcohols, volume excluding agents (e.g., sometimes also referred to as crowding agents), or combinations thereof. Salts may comprise chaotropic salts, ionic salts or a combination of such salts. Non-limiting examples of chaotropic salts include guanidine salt, guanidinium salt, sodium iodide, potassium iodide, sodium thiocyanate and urea. Non-limiting examples of ionic salts include sodium chloride, magnesium chloride, calcium chloride, potassium chloride, lithium chloride, barium chloride, cesium chloride, ammonium acetate, sodium acetate, ammonium perchlorate and sodium perchlorate. In some embodiments, a chaotropic salt can be a guanidine salt (e.g., guanidine (iso)thiocyanate, for example). In certain embodiments, an ionic salt can be a sodium salt (e.g., sodium chloride, for example).

In certain embodiments, a salt may be introduced at a concentration sufficient to associate the nucleic acid to a solid support (e.g., substantially all of the nucleic acid), and the salt may be the only component that associates the nucleic acid to the solid phase or more be utilized in combination with other components to perform the same function. Salt concentrations for binding nucleic acids may be dependent on length of nucleic acid, base sequence, combinations thereof and the like, and can be determined. In some embodiments a salt is utilized in an amount that yields a final salt concentration in the range of about 0.25M to about 5M of the salt (e.g., 0.5M, 1M, 1.5M, 2M, 2.5M, 3M, 4M, or 5M). Salt concentrations also can be expressed as percent weight per volume and salt concentration ranges expressed as ranges of percent weight per volume (e.g., 40 to 60% weight per volume), and can be used interchangeably with Molar concentrations. In some embodiments, the salt concentration chosen may be sufficient to bind substantially all non-target nucleic acid to a solid support, while minimizing the binding of target nucleic acid. In certain embodiments, the salt concentration chosen may be sufficient to associate all or substantially all the nucleic acid in solution. In some embodiments a salt can be added to yield a solution with a concentration in the range of about 5% to about 60% weight per volume that may be sufficient to associate target or total nucleic acid to a solid support. In some embodiments, additional solid phase also may be used to ensure capture of all nucleic acid from a sample.

Alcohols suitable for use in association conditions with the methods described herein are the C1-C6 alkyl alcohols, and their branched chain derivatives or isoforms. Non-limiting examples of the C1-C6 alcohols are methanol (C1), ethanol (C2), propanol (C3), butanol (C4), pentanol (C5), and hexanol (C6), and linear and branched variants thereof. In some embodiments the alkyl alcohol is included in a final amount (percent volume of alcohol in water or aqueous buffered solution) in the range of about 25% or more, 30% or more, 35% or more, 40% or more, 45% or more, 50% or more, 55% or more, 60% or more, 65% or more, 70% or more, 75% or more, 80% or more, 85% or more, 90% or more, 95% or more, or up to 99% or more. In some embodiments, ethanol is used for associating nucleic acids with the solid phase (e.g., magnetically responsive silica dioxide beads). In certain embodiments, the final concentration of ethanol is about 33%. In some embodiments, an alcohol is used as a wash solution to remove impurities. In embodiments using an alcohol as a wash solution, the alcohol often is between about 75% to about 95% alcohol (e.g., ethanol).

Volume excluding agents sometimes may be included in association conditions, in some embodiments. In certain embodiments, volume excluding agents can be used in size selection (e.g., dissociation) buffers or solutions. Volume excluding agents can be suitable for use in (i) association conditions, and/or (ii) dissociation conditions that allow for preferential dissociation of nucleic acid of a particular size (e.g., size selection). Volume excluding agents include, without limitation, polyalkyl glycol (e.g., polyethylene glycol (PEG), for example), dextran, Ficoll, polyvinyl pyrollidone or combinations thereof. In some embodiments, volume exclusion agents (also referred to as "crowding agents") can be added to yield a solution containing between about 5% to about 30% volume exclusion agent, and more specifically between about 8% to about 20% volume exclusion agent. That is, a volume excluding agent may be added to size selection or dissociation conditions to yield solutions containing up to about 5% volume excluding agent, up to about 6%, up to about 7%, up to about 8%, up to about 9%, up to about 10%, up to about 11%, up to about 12%, up to about 13%, up to about 14%, up to about 15%, up to about 16%, up to about 17%, up to about 18%, up to about 19%, up to about 20%, up to about 25%, up to about, and up to about 30% volume excluding agent.

The term "dissociation conditions" as used herein refers to conditions under which (i) a subset of nucleic acid associated with the solid phase, or (ii) substantially all of the nucleic acid associated with a solid phase, is removed from the solid phase. For example, target nucleic acid may exist in a population that is smaller than 300 nucleotides or base pairs, and dissociation conditions may be selected to selectively dissociate nucleic acids smaller than 300 nucleotides or base pairs. The terms "preferential dissociation", "preferentially dissociates" and grammatical variants thereof, as used herein, refers to conditions under which target nucleic acids within a specific size range (e.g., between 5 and 300 nucleotides or base pairs, for example) are substantially or completely eluted from the solid support, while the larger, non-target nucleic acid remains substantially bound. That is, a specifically selected size range of nucleic acids (e.g., relatively short nucleic acids) may be preferentially removed from the solid support under the appropriate dissociation conditions, while leaving behind the larger, unwanted or non-target nucleic acids.

The term "eluate" as used herein refers to the solution portion in a composition that comprises a solid phase and a solution. An eluate under dissociation conditions can include relatively short nucleic acid and relatively long nucleic acid dissociated from the solid phase, where the relatively short nucleic acid is preferentially dissociated from the solid phase as compared to the relatively long nucleic acid under the dissociation conditions, in some embodiments. Thus, in certain embodiments, an eluate can include about 1.5-fold to about 5-fold more relatively short nucleic acid as compared to relatively long nucleic acid, where the relatively short nucleic acid is about 300 base pairs or less (e.g., 10, 20, 30, 40, 50, 60, 70, 80, 90, 100, 110, 120, 130, 140, 150, 160, 170, 180, 190, 200, 210, 220, 230, 340, 250, 260, 270, 280, 290 base pairs), after the nucleic acid and solid phase have been exposed to dissociation conditions to completion.

Certain dissociation conditions for eluting specific size ranges of nucleic acids are presented below in Table 1 (presented below in Example 3). In some embodiments, dissociation conditions contain one or more salts (e.g., ionic salt, chaotropic salt) and one or more volume exclusion agents (e.g., polyalkyl glycol, Ficoll, dextran, polyvinyl pyrollidone (PVP) and the like). In some embodiments, a dissociation condition may include C1-C6 alkyl alcohols. The components utilized in the dissociation conditions can be utilized in any suitable amount that allow for preferential dissociation of a relatively short nucleic acid, in some embodiments. In some embodiments, an ionic salt may be utilized in dissociation conditions in an amount between about 0.05M to about 2.0M, and sometimes between about 0.05M to about 1.0M (e.g., about 0.1, 0.2, 0.3, 0.4, 0.5, 0.6, 0.7, 0.8, 0.9 and 1.0 M). In some embodiments, the ionic salt used for dissociation of specific size fractions of nucleic acids is sodium chloride (NaCl). In some embodiments the concentration of sodium chloride is in the range of about 0.25M to about 1.0M NaCl, and specific concentrations useful for isolating specific sized fractions may be found in Table 1.

In certain embodiments, a volume exclusion agent may be utilized in dissociation conditions in an amount between about 5% to about 30% (e.g., weight to volume). Where the volume exclusion agent is a polyalkyl glycol, the polyalkyl glycol sometimes is utilized within a range of about 5% to about 25% in certain embodiments (e.g., about 6, 7, 8, 9, 10, 11, 12, 13, 14, 15, 16, 17, 18, 19 or 20%). The polyalkyl glycol can have an average, mean or nominal molecular weight of about 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000 or 90000 grams per mole. The polyalkyl glycol sometimes is branched or linear, and sometimes is a polyethylene glycol (PEG).

Where one volume exclusion agent is utilized at an optimum amount, the amount of a different volume exclusion agent for alternative dissociation conditions can be optimized based in part on the molecular weight of the different volume exclusion agent. For example, if a volume exclusion agent that has been included in optimized dissociation conditions has a particular molecular weight, a different volume exclusion agent having a higher molecular weight sometimes will be utilized at a lower amount, and a different volume exclusion agent having a lower molecular weight sometimes will be utilized at a higher amount. Where PEG8000 is utilized at a particular percentage for optimized dissociation conditions, for example, a person of ordinary skill in the art often use a lower amount of a different volume exclusion agent having a higher molecular weight (e.g., PEG16000, Ficoll, dextran or polyvinyl pyrollidone), and often will use a higher amount of a different volume exclusion agent having a lower molecular weight (e.g., PEG4000). In some embodiments, dissociation conditions can include about 5% to about 8% Ficoll, about 2% to about 4% dextran, or about 8% to about 10% polyvinyl pyrollidone (PVP). The PVP sometimes is PVP40 and often is not PVP10.

Particles or beads having a nominal, average or mean diameter of about 1 nanometer to about 500 micrometers can be utilized, such as those having a nominal, mean or average diameter, for example, of about 10 nanometers to about 100 micrometers; about 100 nanometers to about 100 micrometers; about 1 micrometer to about 100 micrometers; about 10 micrometers to about 50 micrometers; about 1, 5, 10, 15, 20, 25, 30, 35, 40, 45, 50, 55, 60, 65, 70, 75, 80, 85, 90, 95, 100, 200, 300, 400, 500, 600, 700, 800 or 900 nanometers; or about 1, 5, 10, 15, 20, 25, 30, 35, 40, 45, 50, 55, 60, 65, 70, 75, 80, 85, 90, 95, 100, 200, 300, 400, 500 micrometers.

A solid support can comprise virtually any insoluble or solid material, and often a solid support composition is selected that is insoluble in water. For example, a solid support can comprise or consist essentially of silica gel, glass (e.g. controlled-pore glass (CPG)), nylon, Sephadex®, Sepharose®, cellulose, a metal surface (e.g. steel, gold, silver, aluminum, silicon and copper), a magnetic material, a plastic material (e.g., polyethylene, polypropylene, polyamide, polyester, polyvinylidenedifluoride (PVDF)) and the like. Beads or particles may be swellable (e.g., polymeric beads such as Wang resin) or non-swellable (e.g., CPG). Commercially available examples of beads include without limitation Wang resin, Merrifield resin and Dynabeads® and SoluLink.

A solid support may be provided in a collection of solid supports. A solid support collection comprises two or more different solid support species. The term "solid support species" as used herein refers to a solid support in association with one particular solid phase nucleic acid species or a particular combination of different solid phase nucleic acid species. In certain embodiments, a solid support collection comprises 2 to 10,000 solid support species, 10 to 1,000 solid support species or about 2, 3, 4, 5, 6, 7, 8, 9, 10, 15, 20, 25, 30, 35, 40, 45, 50, 55, 60, 65, 70, 75, 80, 85, 90, 95, 100, 200, 300, 400, 500, 600, 700, 800, 900, 1000, 2000, 3000, 4000, 5000, 6000, 7000, 8000, 9000 or 10000 unique solid support species. The solid supports (e.g., beads) in the collection of solid supports may be homogeneous (e.g., all are Wang resin beads) or heterogeneous (e.g., some are Wang resin beads and some are magnetic beads). Each solid support species in a collection of solid supports sometimes is labeled with a specific identification tag. An identification tag for a particular solid support species sometimes is a nucleic acid (e.g., "solid phase nucleic acid") having a unique sequence in certain embodiments. An identification tag can be any molecule that is detectable and distinguishable from identification tags on other solid support species.

In certain embodiments, a biological sample can be contacted with a solid support in the presence of a lysing/binding reagent to bind all nucleic acids to a solid support, the inhibitors are washed away, then size selection is performed by adding different concentrations of salts and crowding agents to the solid support selectively removing smaller fragments and leaving larger fragments on the solid support. Additional size selected elutions can be performed if a particular range of fragments is required that is not eluted in the first size elution. Larger fragments or non-target fragments also can be enriched by eluting the larger fragments from the solid support under appropriate conditions, or by eluting the smaller fragments and removing the supernatant to a new tube, where the larger fragments remain on the solid support and are thereby enriched. In some embodiments, the eluted small or target fragments can be further concentrated, enriched and/or purified by binding to new beads in the presence of the appropriate concentration of salt and precipitating agent, washing to remove non-nucleic acid impurities, and eluting in an appropriate aqueous buffer or water.

Enrichment

Target nucleic acid (e.g., relatively short nucleic acids from about 50 to about 200 nucleotides or base pairs in length), can be enriched relative to the target nucleic acid concentration in a total nucleic acid composition, or with respect to larger non-target nucleic acid fractions, using methods and compositions described herein. In some embodiments, relatively short nucleic acids may be enriched relative to the total population of nucleic acids from a sample. Total nucleic acid from a sample may be bound to solid support under appropriate association conditions (see Example 1 for a non-limiting example of appropriate association conditions). Relatively short, target nucleic acids may be purified by collecting the solid support (e.g., by centrifugation or use of a magnetic field for paramagnetic particles, for example), and optionally removing the supernatant to a new tube, after incubating under dissociation conditions for a sufficient period of time that preferentially release the relatively short nucleic acid from the solid phase. The relatively short nucleic acid is thereby enriched, relative to total nucleic acid by virtue of preferential dissociation from the solid phase relative to the relatively large non-target nucleic acid.

In certain embodiments, enrichment is a measure of the percent increase in the amount of relatively short nucleic acid in the disassociated nucleic acid as compared to in the nucleic acid composition subjected to the enrichment process (e.g., percent increase in the relatively small nucleic acid). In certain embodiments, this measure of enrichment is about 10% to about 45% (e.g., about 15, 20, 25, 26, 27, 28, 29, 30, 31, 32, 33, 34, 35, 36, 37, 38, 39, 40, 41, 42, 43 or 44% enrichment).

In some embodiments, enrichment is a ratio of relatively small nucleic acid to relatively large nucleic acid in all of the nucleic acid eluted from the solid support under dissociation conditions. In certain embodiments, the ratio is about 1.05 to about 5 (e.g., ratio of about 1.2, 1.4, 1.6, 1.8, 2.0, 2.2, 2.4, 2.6, 2.8, 3.0, 3.2, 3.4, 3.6, 3.8, 4.0, 4.2, 4.4, 4.6, 4.8 relatively short nucleic acid to relatively long nucleic acid).

Further enrichment of subspecies of relatively short target nucleic acids also may be performed using similar procedures and the appropriate association and dissociation conditions, using the size selected nucleic acids described above, in certain embodiments. Longer target, or non-target nucleic acids also may be enriched using similar methods. The total nucleic acid can be subjected to association conditions sufficient to bind only larger nucleic acids, while leaving smaller nucleic acids in solution. The solid support is removed from the non-bound nucleic acids in the supernatant, thereby enriching larger nucleic acids.

Enriched nucleic acids of any size also may be further concentrated using the methods and compositions described herein. Concentration of nucleic acids may be performed by binding the size selected fraction of nucleic acids, under appropriate association conditions, washing, one or more times, to remove impurities, followed by dissociation (elution) in a smaller volume, of an appropriate buffer or solution, than the original starting volume, thereby concentrating the previously size selected fraction. In some embodiments, concentration and additional size selection can be performed concurrently using the appropriate elution or dissociation buffer, as shown in Table 1 (see Example 3). Concentration also may be achieved by precipitating dissociated target nucleic, for example.

Figure 2:
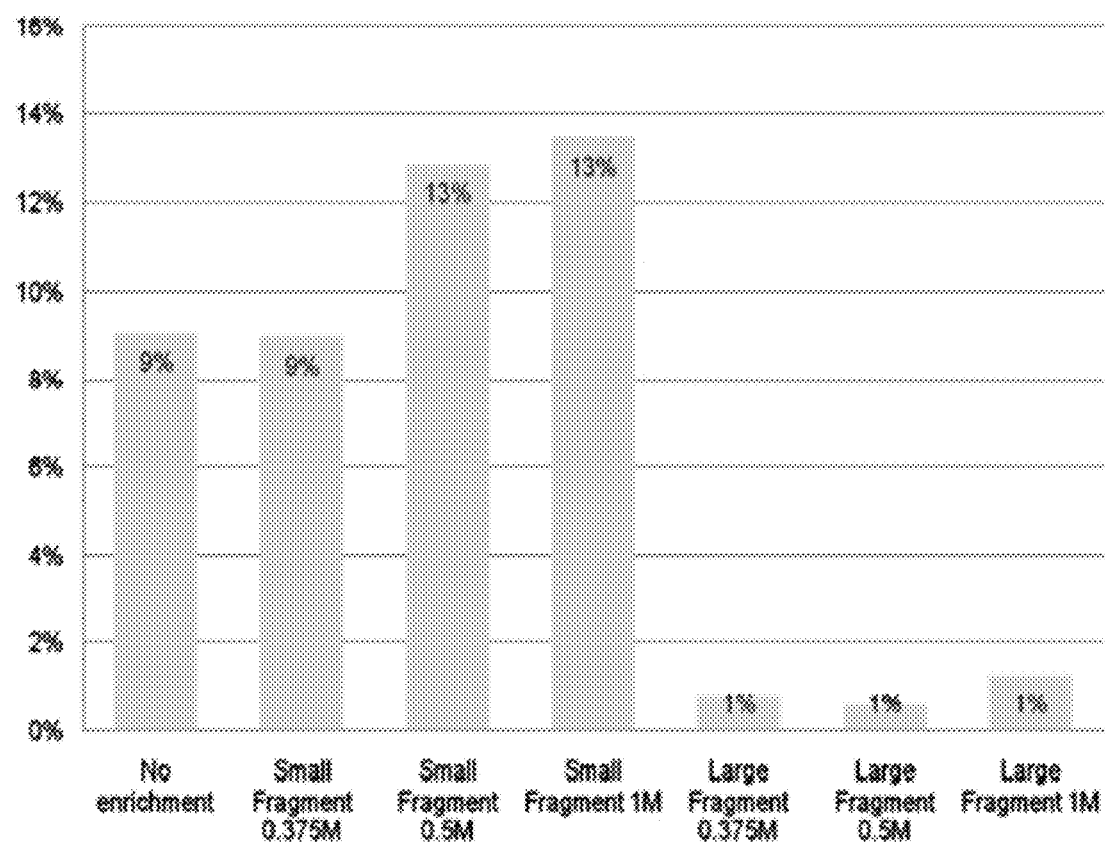
FIG. 2 shows the percent male fetus DNA relative to total DNA isolate from the serum of a pregnant female, and the recovery of small fragments at various salt concentrations as compared to the recovery of large fragments at the same salt concentrations. The percent fold enrichment (e.g., approximately 30%) can be calculated from the data presented in FIG. 2, as described in Example 2. Enrichment was performed using three different salt titrations 0.375M NaCl/10% PEG, 0.5M NaCl/10% PEG, and 1M NaCl/10% PEG, which selects for less than 500 base pairs, less than 400 base pairs, and less than 300 base pairs, respectively.

FIG. 2 (see Example 2) illustrates the successful enrichment of relatively short nucleic acids in relation to the relatively long nucleic acids. The fold enrichment is calculated to be approximately 30% enrichment (e.g., 100%–(9%/13%)) of the male fetal DNA, and is achieved by selecting for nucleic acids 300 nucleotides or base pairs and lower.

Amplification

In some embodiments, it may be desirable to amplify the target sequence using any of several nucleic acid amplification procedures (described in greater detail below). Nucleic acid amplification may be particularly beneficial when target sequences exist at low copy number, or the target sequences are non-host sequences and represent a small portion of the total nucleic acid in the sample (e.g., fetal nucleic acid in a maternal nucleic acid background). In some embodiments, amplification of target sequences may aid in detection of gene dosage imbalances, as might be seen in genetic disorders involving chromosomal aneuploidy, for example. In some embodiments it may be desirable to amplify target nucleic acids that have been size selected using methods and compositions described herein. In certain embodiments, total nucleic acid isolated from substantially cell free samples may be amplified prior to using size selection methods and compositions described herein. In some embodiments, size selection of nucleic acid species of a particular size range (e.g., between about 50 to about 300 nucleotides of base pairs, or between about 50 to about 200 nucleotides or base pairs, for example) can be performed prior to amplification, to allow amplification and further enrichment of only target nucleic acid species. Nucleic acid amplification often involves enzymatic synthesis of nucleic acid amplicons (copies), which contain a sequence complementary to a nucleotide sequence species being amplified. An amplification product (amplicon) of a particular nucleotide sequence species (e.g., target sequence) is referred to herein as an "amplified nucleic acid species." Amplifying target sequences and detecting the amplicon synthesized, can improve the sensitivity of an assay, since fewer target sequences are needed at the beginning of the assay, and can improve detection of target sequences.

The terms "amplify", "amplification", "amplification reaction", or "amplifying" refers to any in vitro processes for multiplying the copies of a target sequence of nucleic acid. Amplification sometimes refers to an "exponential" increase in target nucleic acid. However, "amplifying" as used herein can also refer to linear increases in the numbers of a select target sequence of nucleic acid, but is different than a one-time, single primer extension step. In some embodiments, a one-time, single oligonucleotide extension step can be used to generate a double stranded nucleic acid feature (e.g., synthesize the complement of a restriction endonuclease cleavage site contained in a single stranded oligonucleotide species, thereby creating a restriction site).

In some embodiments, a limited amplification reaction, also known as pre-amplification, can be performed. Pre-amplification is a method in which a limited amount of amplification occurs due to a small number of cycles, for example 10 cycles, being performed. Pre-amplification can allow some amplification, but stops amplification prior to the exponential phase, and typically produces about 500 copies of the desired nucleotide sequence(s). Use of pre-amplification may also limit inaccuracies associated with depleted reactants in standard PCR reactions, and also may reduce amplification biases due to nucleotide sequence or species abundance of the target. In some embodiments, a one-time primer extension may be used may be performed as a prelude to linear or exponential amplification. In some embodiments, amplification of the target nucleic acid may not be required, due to the use of ultra sensitive detections methods (e.g., single nucleotide sequencing, sequencing by synthesis and the like).

Where amplification may be desired, any suitable amplification technique can be utilized. Non-limiting examples of methods for amplification of polynucleotides include, polymerase chain reaction (PCR); ligation amplification (or ligase chain reaction (LCR)); amplification methods based on the use of Q-beta replicase or template-dependent polymerase (see US Patent Publication Number US20050287592); helicase-dependant isothermal amplification (Vincent et al., "Helicase-dependent isothermal DNA amplification". EMBO reports 5 (8): 795-800 (2004)); strand displacement amplification (SDA); thermophilic SDA nucleic acid sequence based amplification (3SR or NASBA) and transcription-associated amplification (TAA). Non-limiting examples of PCR amplification methods include standard PCR, AFLP-PCR, Allele-specific PCR, Alu-PCR, Asymmetric PCR, Colony PCR, Hot start PCR, Inverse PCR (IPCR), In situ PCR (ISH), Intersequence-specific PCR (ISSR-PCR), Long PCR, Multiplex PCR, Nested PCR, Quantitative PCR, Reverse Transcriptase PCR (RT-PCR), Real Time PCR, Single cell PCR, Solid phase PCR, combinations thereof, and the like. Reagents and hardware for conducting PCR are commercially available.

In some embodiments, amplification target nucleic acid may be accomplished by any suitable method available to one of skill in the art or selected from the listing above (e.g., ligase chain reaction (LCR), transcription-mediated amplification, and self-sustained sequence replication or nucleic acid sequence-based amplification (NASBA)). More recently developed branched-DNA technology also may be used to amplify the signal of target nucleic acids. For a review of branched-DNA (bDNA) signal amplification for direct quantification of nucleic acid sequences in clinical samples, see Nolte, Adv. Clin. Chem. 33:201-235, 1998.

Amplification also can be accomplished using digital PCR, in certain embodiments (e.g., Kalinina and colleagues (Kalinina et al., "Nanoliter scale PCR with TaqMan detection." Nucleic Acids Research. 25; 1999-2004, (1997); Vogelstein and Kinzler (Digital PCR. Proc Natl Acad Sci USA. 96; 9236-41, (1999); PCT Patent Publication No. WO05023091A2 (incorporated herein in its entirety); US Patent Publication No. 20070202525 (incorporated herein in its entirety)). Digital PCR takes advantage of nucleic acid (DNA, cDNA or RNA) amplification on a single molecule level, and offers a highly sensitive method for quantifying low copy number nucleic acid. Systems for digital amplification and analysis of nucleic acids are available (e.g., Fluidigm® Corporation).

In some embodiments, where RNA nucleic acid species may be used for detection of fetal sequences, a DNA copy (cDNA) of the RNA transcripts of interest can be synthesized prior to the amplification step. The cDNA copy can be synthesized by reverse transcription, which may be carried out as a separate step, or in a homogeneous reverse transcription-polymerase chain reaction (RT-PCR), a modification of the polymerase chain reaction for amplifying RNA. Methods suitable for PCR amplification of ribonucleic acids are described by Romero and Rotbart in Diagnostic Molecular Biology: Principles and Applications pp. 401-406; Persing et al., eds., Mayo Foundation, Rochester, Minn., 1993; Egger et al., J. Clin. Microbiol. 33:1442-1447, 1995; and U.S. Pat. No. 5,075,212.

Use of a primer extension reaction also can be applied in methods of the technology. A primer extension reaction operates, for example, by discriminating nucleic acid sequences, SNP alleles for example, at a single nucleotide mismatch (e.g., a mismatch between paralogous sequences, or SNP alleles). The terms "paralogous sequence" or "paralogous sequences" refer to sequences that have a common evolutionary origin but which may be duplicated over time in the genome of interest. Paralogous sequences may conserve gene structure (e.g., number and relative position of introns and exons and preferably transcript length), as well as sequence. Therefore, the methods described herein can be used to detect sequence mismatches in SNP-alleles or in evolutionarily conserved regions that differ by one or more point mutations, insertions or deletions (both will hereinafter be referred to as "mismatch site" or "sequence mismatch").

The mismatch may be detected by the incorporation of one or more deoxynucleotides and/or dideoxynucleotides to a primer extension primer or oligonucleotide species, which hybridizes to a region adjacent to the SNP site (e.g., mismatch site). The extension oligonucleotide generally is extended with a polymerase. In some embodiments, a detectable tag, detectable moiety or detectable moiety is incorporated into the extension oligonucleotide or into the nucleotides added on to the extension oligonucleotide (e.g., biotin or streptavidin). The extended oligonucleotide can be detected by any known suitable detection process (e.g., mass spectrometry; sequencing processes). In some embodiments, the mismatch site is extended only by one or two complementary deoxynucleotides or dideoxynucleotides that are tagged by a specific label or generate a primer extension product with a specific mass, and the mismatch can be discriminated and quantified.

For embodiments using primer extension methods to amplify a target sequence, the extension of the oligonucleotide species is not limited to a single round of extension, and is therefore distinguished from "one-time primer extension" described above. Non-limiting examples of primer extension or oligonucleotide extension methods suitable for use with embodiments described herein are described in U.S. Pat. Nos. 4,656,127; 4,851,331; 5,679,524; 5,834,189; 5,876,934; 5,908,755; 5,912,118; 5,976,802; 5,981,186; 6,004,744; 6,013,431; 6,017,702; 6,046,005; 6,087,095; 6,210,891; and WO 01/20039, for example.

A generalized description of an amplification process is presented herein. Oligonucleotide species compositions described herein and target nucleic acid are contacted, and complementary sequences anneal to one another, for example. Oligonucleotides can anneal to a nucleic acid, at or near (e.g., adjacent to, abutting, and the like) a target sequence of interest. A reaction mixture, containing all components necessary for full enzymatic functionality, is added to the oligonucleotide species—target nucleic acid hybrid, and amplification can occur under suitable conditions. Components of an amplification reaction may include, but are not limited to, e.g., oligonucleotide species compositions (e.g., individual oligonucleotides, oligonucleotide pairs, oligonucleotide sets and the like) a polynucleotide template (e.g., nucleic acid containing a target sequence), polymerase, nucleotides, dNTPs, an appropriate endonuclease and the like. Extension conditions are sometimes a subset of, or substantially similar to amplification conditions.

In some embodiments, non-naturally occurring nucleotides or nucleotide analogs, such as analogs containing a detectable moiety or feature (e.g., fluorescent or colorimetric label) may be used, for example. Polymerases can be selected by a person of ordinary skill and include polymerases for thermocycle amplification (e.g., Taq DNA Polymerase; Q-Bio™ Taq DNA Polymerase (recombinant truncated form of Taq DNA Polymerase lacking 5'-3'exo activity); SurePrime™ Polymerase (chemically modified Taq DNA polymerase for "hot start" PCR); Arrow™ Taq DNA Polymerase (high sensitivity and long template amplification)) and polymerases for thermostable amplification (e.g., RNA polymerase for transcription-mediated amplification (TMA) described at World Wide Web URL "genprobe.com/pdfs/tma_whiteppr.pdf"). Other enzyme components can be added, such as reverse transcriptase for transcription mediated amplification (TMA) reactions, for example.

The terms "near" or "adjacent to" when referring to a nucleotide target sequence refers to a distance or region between the end of the primer and the nucleotide or nucleotides of interest. As used herein adjacent is in the range of about 5 nucleotides to about 500 nucleotides (e.g., about 5 nucleotides away from nucleotide of interest, about 10, about 20, about 30, about 40, about 50, about 60, about 70, about 80, about 90, about 100, about 150, about 200, about 250, about 300, abut 350, about 400, about 450 or about 500 nucleotides from a nucleotide of interest).

Each amplified nucleic acid species independently can be about 10 to about 1000 base pairs in length in some embodiments. In certain embodiments, an amplified nucleic acid species is about 20 to about 250 base pairs in length, sometimes is about 50 to about 150 base pairs in length and sometimes is about 100 base pairs in length. Thus, in some embodiments, the length of each of the amplified nucleic acid species products independently is about 10, 15, 20, 25, 30, 35, 40, 45, 50, 55, 60, 65, 70, 75, 80, 82, 84, 86, 88, 90, 92, 94, 96, 98, 100, 102, 104, 106, 108, 110, 112, 114, 116, 118, 120, 125, 130, 135, 140, 145, 150, 175, 200, 250, 300, 350, 400, 450, 500, 550, 600, 650, 700, 750, 800, 850, 900, 950 or 1000 base pairs (bp) in length.

An amplification product may include naturally occurring nucleotides, non-naturally occurring nucleotides, nucleotide analogs and the like and combinations of the foregoing. An amplification product often has a nucleotide sequence that is identical to or substantially identical to a target sequence or complement thereof. A "substantially identical" nucleotide sequence in an amplification product will generally have a high degree of sequence identity to the nucleotide sequence species being amplified or complement thereof (e.g., about 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater than 99% sequence identity), and variations sometimes are a result of infidelity of the polymerase used for extension and/or amplification, or additional nucleotide sequence(s) added to the primers used for amplification.

PCR conditions can be dependent upon primer sequences, target abundance, and the desired amount of amplification, and therefore, one of skill in the art may choose from a number of PCR protocols available (see, e.g., U.S. Pat. Nos. 4,683,195 and 4,683,202; and PCR Protocols: A Guide to Methods and Applications, Innis et al., eds, 1990. PCR often is carried out as an automated process with a thermostable enzyme. In this process, the temperature of the reaction mixture is cycled through a denaturing region, a primer-annealing region, and an extension reaction region automatically. Machines specifically adapted for this purpose are commercially available. A non-limiting example of a PCR protocol that may be suitable for embodiments described herein is, treating the sample at 95° C. for 5 minutes; repeating forty-five cycles of 95° C. for 1 minute, 59° C. for 1 minute, 10 seconds, and 72° C. for 1 minute 30 seconds; and then treating the sample at 72° C. for 5 minutes. Additional PCR protocols are described in the example section. Multiple cycles frequently are performed using a commercially available thermal cycler. Suitable isothermal amplification processes known and selected by the person of ordinary skill in the art also may be applied, in certain embodiments.

In some embodiments, multiplex amplification processes may be used to amplify target sequences, such that multiple amplicons are simultaneously amplified in a single, homogenous reaction. As used herein "multiplex amplification" refers to a variant of PCR where simultaneous amplification of many target sequences in one reaction vessel may be accomplished by using more than one pair of primers (e.g., more than one primer set). Multiplex amplification may be useful for analysis of deletions, mutations, and polymorphisms, or quantitative assays, in some embodiments. In certain embodiments multiplex amplification may be used for detecting paralog sequence imbalance, genotyping applications where simultaneous analysis of multiple markers is required, detection of pathogens or genetically modified organisms, or for microsatellite analyses. In some embodiments multiplex amplification may be combined with another amplification (e.g., PCR) method (e.g., nested PCR or hot start PCR, for example) to increase amplification specificity and reproducibility. In some embodiments, multiplex amplification processes may be used to amplify the Y-chromosome loci described herein.

In certain embodiments, nucleic acid amplification can generate additional nucleic acid species of different or substantially similar nucleic acid sequence. In certain embodiments described herein, contaminating or additional nucleic acid species, which may contain sequences substantially complementary to, or may be substantially identical to, the target sequence, can be useful for sequence quantification, with the proviso that the level of contaminating or additional sequences remains constant and therefore can be a reliable marker whose level can be substantially reproduced. Additional considerations that may affect sequence amplification reproducibility are; PCR conditions (number of cycles, volume of reactions, melting temperature difference between primers pairs, and the like), concentration of target nucleic acid in sample (e.g. fetal nucleic acid in maternal nucleic acid background, viral nucleic acid in host background), the number of chromosomes on which the nucleotide species of interest resides (e.g., paralogous sequences or SNP-alleles), variations in quality of prepared sample, and the like. The terms "substantially reproduced" or "substantially reproducible" as used herein refer to a result (e.g., quantifiable amount of nucleic acid) that under substantially similar conditions would occur in substantially the same way about 75% of the time or greater, about 80%, about 85%, about 90%, about 95%, or about 99% of the time or greater.

In some embodiments, amplification may be performed on a solid support. In some embodiments, primers may be associated with a solid support. In certain embodiments, target nucleic acid (e.g., template nucleic acid or target sequences) may be associated with a solid support. A nucleic acid (primer or target) in association with a solid support often is referred to as a solid phase nucleic acid.

In some embodiments, nucleic acid molecules provided for amplification are in a "microreactor". As used herein, the term "microreactor" refers to a partitioned space in which a nucleic acid molecule can hybridize to a solid support nucleic acid molecule. Examples of microreactors include, without limitation, an emulsion globule (described hereafter) and a void in a substrate. A void in a substrate can be a pit, a pore or a well (e.g., microwell, nanowell, picowell, micropore, or nanopore) in a substrate constructed from a solid material useful for containing fluids (e.g., plastic (e.g., polypropylene, polyethylene, polystyrene) or silicon) in certain embodiments. Emulsion globules are partitioned by an immiscible phase as described in greater detail hereafter. In some embodiments, the microreactor volume is large enough to accommodate one solid support (e.g., bead) in the microreactor and small enough to exclude the presence of two or more solid supports in the microreactor.

The term "emulsion" as used herein refers to a mixture of two immiscible and unblendable substances, in which one substance (the dispersed phase) often is dispersed in the other substance (the continuous phase). The dispersed phase can be an aqueous solution (i.e., a solution comprising water) in certain embodiments. In some embodiments, the dispersed phase is composed predominantly of water (e.g., greater than 70%, greater than 75%, greater than 80%, greater than 85%, greater than 90%, greater than 95%, greater than 97%, greater than 98% and greater than 99% water (by weight)). Each discrete portion of a dispersed phase, such as an aqueous dispersed phase, is referred to herein as a "globule" or "microreactor." A globule sometimes may be spheroidal, substantially spheroidal or semi-spheroidal in shape, in certain embodiments.

The terms "emulsion apparatus" and "emulsion component(s)" as used herein refer to apparatus and components that can be used to prepare an emulsion. Non-limiting examples of emulsion apparatus include without limitation counter-flow, cross-current, rotating drum and membrane apparatus suitable for use by a person of ordinary skill to prepare an emulsion. An emulsion component forms the continuous phase of an emulsion in certain embodiments, and includes without limitation a substance immiscible with water, such as a component comprising or consisting essentially of an oil (e.g., a heat-stable, biocompatible oil (e.g., light mineral oil)). A biocompatible emulsion stabilizer can be utilized as an emulsion component. Emulsion stabilizers include without limitation Atlox 4912, Span 80 and other biocompatible surfactants.

In some embodiments, components useful for biological reactions can be included in the dispersed phase. Globules of the emulsion can include (i) a solid support unit (e.g., one bead or one particle); (ii) sample nucleic acid molecule; and (iii) a sufficient amount of extension agents to elongate solid phase nucleic acid and amplify the elongated solid phase nucleic acid (e.g., extension nucleotides, polymerase, primer). In some embodiments, endonucleases and components necessary for endonuclease function may be included in the components useful for biological reactions as described below in the example section. Inactive globules in the emulsion may include a subset of these components (e.g., solid support and extension reagents and no sample nucleic acid) and some can be empty (i.e., some globules will include no solid support, no sample nucleic acid and no extension agents).

Emulsions may be prepared using known suitable methods (e.g., Nakano et al. "Single-molecule PCR using water-in-oil emulsion;" Journal of Biotechnology 102 (2003) 117-124). Emulsification methods include without limitation adjuvant methods, counter-flow methods, cross-current methods, rotating drum methods, membrane methods, and the like. In certain embodiments, an aqueous reaction mixture containing a solid support (hereafter the "reaction mixture") is prepared and then added to a biocompatible oil. In certain embodiments, the reaction mixture may be added dropwise into a spinning mixture of biocompatible oil (e.g., light mineral oil (Sigma)) and allowed to emulsify. In some embodiments, the reaction mixture may be added dropwise into a cross-flow of biocompatible oil. The size of aqueous globules in the emulsion can be adjusted, such as by varying the flow rate and speed at which the components are added to one another, for example.

The size of emulsion globules can be selected by the person of ordinary skill in certain embodiments based on two competing factors: (i) globules are sufficiently large to encompass one solid support molecule, one sample nucleic acid molecule, and sufficient extension agents for the degree of elongation and amplification required; and (ii) globules are sufficiently small so that a population of globules can be amplified by conventional laboratory equipment (e.g., thermocycling equipment, test tubes, incubators and the like). Globules in the emulsion can have a nominal, mean or average diameter of about 5 microns to about 500 microns, about 10 microns to about 350 microns, about 50 to 250 microns, about 100 microns to about 200 microns, or about 5, 10, 15, 20, 25, 30, 35, 40, 45, 50, 55, 60, 65, 70, 75, 80, 85, 90, 95, 100, 200, 300, 400 or 500 microns in certain embodiments.

In certain embodiments, amplified nucleic acid species in a set are of identical length, and sometimes the amplified nucleic acid species in a set are of a different length. For example, one amplified nucleic acid species may be longer than one or more other amplified nucleic acid species in the set by about 1 to about 100 nucleotides (e.g., about 2, 3, 4, 5, 6, 7, 8, 9, 10, 11, 12, 13, 14, 15, 16, 17, 18, 19, 20, 30, 40, 50, 60, 70, 80 or 90 nucleotides longer).

In some embodiments, a ratio can be determined for the amount of one amplified nucleic acid species in a set to the amount of another amplified nucleic acid species in the set (hereafter a "set ratio"). In some embodiments, the amount of one amplified nucleic acid species in a set is about equal to the amount of another amplified nucleic acid species in the set (i.e., amounts of amplified nucleic acid species in a set are about 1:1), which generally is the case when the number of chromosomes or the amount of DNA representative of nucleic acid species in a sample bearing each nucleotide sequence species amplified is about equal. The term "amount" as used herein with respect to amplified nucleic acid species refers to any suitable measurement, including, but not limited to, copy number, weight (e.g., grams) and concentration (e.g., grams per unit volume (e.g., milliliter); molar units). In some embodiments, the ratio of fetal nucleic acid to maternal nucleic acid (or conversely maternal nucleic acid to fetal nucleic acid) can be used in conjunction with measurements of the ratios of mismatch sequences for determination of chromosomal abnormalities possibly associated with sex chromosomes. That is, the percentage of fetal nucleic acid detected in a maternal nucleic acid background or the ratio of fetal to maternal nucleic acid in a sample, can be used to detect chromosomal aneuploidies.

In certain embodiments, the amount of one amplified nucleic acid species in a set can differ from the amount of another amplified nucleic acid species in a set, even when the number of chromosomes in a sample bearing each nucleotide sequence species amplified is about equal. In some embodiments, amounts of amplified nucleic acid species within a set may vary up to a threshold level at which a chromosome abnormality can be detected with a confidence level of about 95% (e.g., about 90, 91, 92, 93, 94, 95, 96, 97, 98, 99, or greater than 99%). In certain embodiments, the amounts of the amplified nucleic acid species in a set vary by about 50% or less (e.g., about 45, 40, 35, 30, 25, 20, 15, 10, 5, 4, 3, 2 or 1%, or less than 1%). Thus, in certain embodiments amounts of amplified nucleic acid species in a set may vary from about 1:1 to about 1:1.5. Without being limited by theory, certain factors can lead to the observation that the amount of one amplified nucleic acid species in a set can differ from the amount of another amplified nucleic acid species in a set, even when the number of chromosomes in a sample bearing each nucleotide sequence species amplified is about equal. Such factors may include different amplification efficiency rates and/or amplification from a chromosome not intended in the assay design.

Each amplified nucleic acid species in a set generally is amplified under conditions that amplify that species at a substantially reproducible level. The term "substantially reproducible level" as used herein refers to consistency of amplification levels for a particular amplified nucleic acid species per unit template nucleic acid (e.g., per unit template nucleic acid that contains the particular nucleotide sequence species amplified). A substantially reproducible level varies by about 1% or less in certain embodiments, after factoring the amount of template nucleic acid giving rise to a particular amplification nucleic acid species (e.g., normalized for the amount of template nucleic acid). In some embodiments, a substantially reproducible level varies by 5%, 4%, 3%, 2%, 1.5%, 1%, 0.5%, 0.1%, 0.05%, 0.01%, 0.005% or 0.001% after factoring the amount of template nucleic acid giving rise to a particular amplification nucleic acid species.

In some embodiments amplification nucleic acid species (e.g., amplified target sequences) of oligonucleotide species composition sets described herein may be generated in one reaction vessel. In some embodiments amplification of mismatch sequences may be performed in a single reaction vessel. In certain embodiments, mismatch sequences (on the same or different chromosomes) may be amplified by a single oligonucleotide species pair or set. In some embodiments target sequences may be amplified by a single oligonucleotide species pair or set. In some embodiments target sequences in a set may be amplified with two or more oligonucleotide species pairs. In some embodiments a subsequence of a target nucleic acid may be amplified using a single oligonucleotide species pair or set. In some embodiments a subsequence of a target nucleic acid may be amplified using two or more oligonucleotide species pairs.

Polymerase Extendable Oligonucleotide Species Compositions

In certain embodiments, relatively short nucleic acid of a nucleic acid composition is enriched using methods and compositions described herein, and the all, or a subset of, the enriched relatively short nucleic acid is analyzed. An oligonucleotide species that hybridizes to one or more nucleic acids (e.g., target nucleic acids) in the enriched nucleic acid sometimes are utilized. Oligonucleotide species can be useful for amplification, detection, quantification and sequencing of target nucleic acids. In some embodiments the oligonucleotide species compositions may be complementary to, and hybridize or anneal specifically to or near (e.g., adjacent to) sequences that flank a target region therein. In some embodiments the oligonucleotide species compositions described herein are used in sets, where a set contains at least a pair. In some embodiments a set of oligonucleotide species may include a third or a fourth nucleic acid (e.g., two pairs of oligonucleotide species or nested sets of oligonucleotide species, for example). A plurality of oligonucleotide species pairs may constitute a primer set in certain embodiments (e.g., about 2, 3, 4, 5, 6, 7, 8, 9, 10, 15, 20, 25, 30, 35, 40, 45, 50, 55, 60, 65, 70, 75, 80, 85, 90, 95 or 100 pairs). In some embodiments a plurality of oligonucleotide species sets, each set comprising pair(s) of primers, may be used.

The term "oligonucleotide species" as used herein refers to a nucleic acid that comprises a nucleotide sequence capable of hybridizing or annealing to a target nucleic acid, at or near (e.g., adjacent to) a specific region of interest. As used herein, the term "PCR oligonucleotide species composition(s)" refers to oligonucleotides that can be used in a polymerase chain reaction (PCR) to amplify a target nucleotide sequence, for example. In certain embodiments, at least one of the PCR oligonucleotide species for amplification of a nucleotide sequence encoding a target nucleic acid can be a sequence-specific oligonucleotide species composition. In some embodiments, oligonucleotide species compositions described herein may be modified (e.g., addition of a universal primer sequence) to improve multiplexing.

Oligonucleotide species compositions described herein can allow for specific determination of a target nucleic acid nucleotide sequence or detection of the target nucleic acid sequence (e.g., presence or absence of a sequence or copy number of a sequence), or feature thereof, for example. Oligonucleotide species compositions described herein may also be used to detect amplification products or extension products, in certain embodiments. The oligonucleotide compositions and methods of use described herein are useful for minimizing or eliminating extension and/or amplification artifacts (e.g., "primer-dimers" and artifacts caused by annealing and extension during temperature transitions in a PCR thermocycling profile, for example) that can sometimes occur in nucleic acid extension or amplification based assays. The oligonucleotide species compositions described herein include endonuclease cleavage sites for thermostable endonucleases that can be used in methods (single tube assays, multiplexed assays and the like), also described herein, that combine hybridization, cleavage and extension or amplification conditions to allow specific target identification and/or amplification.

The oligonucleotide species compositions described herein are often synthetic, but naturally occurring nucleic acid sequences with similar structure and/or function may be used, in some embodiments. The term "specific", "specifically" or "specificity", as used herein with respect to nucleic acids, refers to the binding or hybridization of one molecule to another molecule, such as a primer for a target polynucleotide sequence. That is, "specific", "specifically" or "specificity" refers to the recognition, contact, and formation of a stable complex between two molecules, as compared to substantially less recognition, contact, or complex formation of either of those two molecules with other molecules. As used herein, the term "anneal" refers to the formation of a stable complex between two molecules. The terms "oligonucleotide species", "oligonucleotide species composition", "oligonucleotide composition", "primer", "oligo", or "oligonucleotide" may be used interchangeably throughout the document, when referring to primers.

The oligonucleotide species compositions described herein can be designed and synthesized using suitable processes, and may be of any length suitable for hybridizing to a nucleotide sequence of interest (e.g., where the nucleic acid is in liquid phase or bound to a solid support) and performing analysis processes described herein. Oligonucleotide species compositions described herein may be designed based upon a target nucleotide sequence. An oligonucleotide species composition in some embodiments may be about 10 to about 100 nucleotides, about 10 to about 70 nucleotides, about 10 to about 50 nucleotides, about 15 to about 30 nucleotides, or about 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95 or 100 nucleotides in length. An oligonucleotide species composition may be composed of naturally occurring and/or non-naturally occurring nucleotides (e.g., labeled nucleotides), or a mixture thereof. Oligonucleotide species composition embodiments suitable for use with method embodiments described herein may be synthesized and labeled using known techniques. Oligonucleotides (e.g., primers) may be chemically synthesized according to the solid phase phosphoramidite triester method first described by Beaucage and Caruthers, Tetrahedron Letts., 22:1859-1862, 1981, using an automated synthesizer, as described in Needham-VanDevanter et al., Nucleic Acids Res. 12:6159-6168, 1984. Purification of oligonucleotides can be effected by native acrylamide gel electrophoresis or by anion-exchange high-performance liquid chromatography (HPLC), for example, as described in Pearson and Regnier, J. Chrom., 255:137-149, 1983.

All or a portion of an oligonucleotide species composition nucleic acid sequence (naturally occurring or synthetic) may be substantially complementary to a target nucleic acid sequence, in some embodiments. As referred to herein, "substantially complementary" with respect to sequences refers to nucleotide sequences that will hybridize with each other. The stringency of the hybridization conditions can be altered to tolerate varying amounts of sequence mismatch. Included are regions of counterpart, target and capture nucleotide sequences 55% or more, 56% or more, 57% or more, 58% or more, 59% or more, 60% or more, 61% or more, 62% or more, 63% or more, 64% or more, 65% or more, 66% or more, 67% or more, 68% or more, 69% or more, 70% or more, 71% or more, 72% or more, 73% or more, 74% or more, 75% or more, 76% or more, 77% or more, 78% or more, 79% or more, 80% or more, 81% or more, 82% or more, 83% or more, 84% or more, 85% or more, 86% or more, 87% or more, 88% or more, 89% or more, 90% or more, 91% or more, 92% or more, 93% or more, 94% or more, 95% or more, 96% or more, 97% or more, 98% or more or 99% or more complementary to each other.

Oligonucleotide compositions that contain subsequences that are substantially complimentary to a target nucleic acid sequence are also substantially identical to the compliment of the target nucleic acid sequence. That is, primers can be substantially identical to the anti-sense strand of the nucleic acid. As referred to herein, "substantially identical" with respect to sequences refers to nucleotide sequences that are 55% or more, 56% or more, 57% or more, 58% or more, 59% or more, 60% or more, 61% or more, 62% or more, 63% or more, 64% or more, 65% or more, 66% or more, 67% or more, 68% or more, 69% or more, 70% or more, 71% or more, 72% or more, 73% or more, 74% or more, 75% or more, 76% or more, 77% or more, 78% or more, 79% or more, 80% or more, 81% or more, 82% or more, 83% or more, 84% or more, 85% or more, 86% or more, 87% or more, 88% or more, 89% or more, 90% or more, 91% or more, 92% or more, 93% or more, 94% or more, 95% or more, 96% or more, 97% or more, 98% or more or 99% or more identical to each other. One test for determining whether two nucleotide sequences are substantially identical is to determine the percent of identical nucleotide sequences shared.

Oligonucleotide species sequences and length may affect hybridization to target nucleic acid sequences. Depending on the degree of mismatch between the oligonucleotide species and target nucleic acid, low, medium or high stringency conditions may be used to effect oligonucleotide/target annealing. As used herein, the term "stringent conditions" refers to conditions for hybridization and washing. Methods for hybridization reaction temperature condition optimization are known to those of skill in the art, and may be found in Current Protocols in Molecular Biology, John Wley & Sons, N.Y., 6.3.1-6.3.6 (1989). Aqueous and non-aqueous methods are described in that reference and either can be used. Non-limiting examples of stringent hybridization conditions are hybridization in 6× sodium chloride/sodium citrate (SSC) at about 45° C., followed by one or more washes in 0.2×SSC, 0.1% SDS at 50° C. Another example of stringent hybridization conditions are hybridization in 6× sodium chloride/sodium citrate (SSC) at about 45° C., followed by one or more washes in 0.2×SSC, 0.1% SDS at 55° C. A further example of stringent hybridization conditions is hybridization in 6× sodium chloride/sodium citrate (SSC) at about 45° C., followed by one or more washes in 0.2×SSC, 0.1% SDS at 60° C. Often, stringent hybridization conditions are hybridization in 6× sodium chloride/sodium citrate (SSC) at about 45° C., followed by one or more washes in 0.2×SSC, 0.1% SDS at 65° C. More often, stringency conditions are 0.5M sodium phosphate, 7% SDS at 65° C., followed by one or more washes at 0.2×SSC, 1% SDS at 65° C. Stringent hybridization temperatures can also be altered (i.e. lowered) with the addition of certain organic solvents, formamide for example. Organic solvents, like formamide, reduce the thermal stability of double-stranded polynucleotides, so that hybridization can be performed at lower temperatures, while still maintaining stringent conditions and extending the useful life of nucleic acids that may be heat labile.

In embodiments using extension or amplification methods described herein, "stringent conditions" can also refer to conditions under which an intact oligonucleotide species composition can anneal to a target nucleic acid, but where one or more cleaved fragments of the oligonucleotide species composition cannot anneal to the target nucleic acid (e.g., intact oligonucleotide anneals at 65 C and one or more fragments anneals at 50 C). In some embodiments, the "stringent conditions" for extension and/or amplification methods described herein are; substantially similar to, a subset of, or include as a subset, hybridization conditions, cleavage conditions, extension conditions, amplification conditions or combinations thereof.

As used herein, the phrase "hybridizing" or grammatical variations thereof, refers to binding of a first nucleic acid molecule to a second nucleic acid molecule under low, medium or high stringency conditions, or under nucleic acid synthesis conditions. Hybridizing can include instances where a first nucleic acid molecule binds to a second nucleic acid molecule, where the first and second nucleic acid molecules are complementary. As used herein, "specifically hybridizes" refers to preferential hybridization under nucleic acid synthesis conditions of an oligonucleotide species, to a nucleic acid molecule having a sequence complementary to the oligonucleotide species compared to hybridization to a nucleic acid molecule not having a complementary sequence. For example, specific hybridization includes the hybridization of an oligonucleotide species composition to a target nucleic acid sequence that is complementary to at least a portion of the oligonucleotide species composition.

In some embodiments oligonucleotide species compositions can include a nucleotide subsequence that may be complementary to a solid phase nucleic acid oligonucleotide hybridization sequence or substantially complementary to a solid phase nucleic acid primer hybridization sequence (e.g., about 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater than 99% identical to the primer hybridization sequence complement when aligned). An oligonucleotide species composition may contain a nucleotide subsequence not complementary to or not substantially complementary to a solid phase nucleic acid oligonucleotide hybridization sequence (e.g., at the 3' or 5' end of the nucleotide subsequence in the oligonucleotide species composition complementary to or substantially complementary to the solid phase oligonucleotide hybridization sequence).

An oligonucleotide species composition, in certain embodiments, may contain a detectable feature, moiety, molecule or entity (e.g., a fluorophore, radioisotope, colorimetric agent, particle, enzyme and the like). In some embodiments, a detectable feature may be a capture agent or a blocking agent. In some embodiments each oligonucleotide species may contain a blocking moiety. In some embodiments the blocking moiety of a first oligonucleotide species is different than the blocking moiety of a second oligonucleotide species. Non-limiting examples of blocking agents include; phosphate group, thiol group, phosphorothioate group, amino modifier, biotin, biotin-TEG, cholesteryl-TEG, digoxigenin NHS ester, thiol modifier C3 S-S (Disulfide), inverted dT, C3 spacer and the like. In some embodiments more than one blocking group can be incorporated into an oligonucleotide species at, or near, one more endonuclease cleavage sites to allow the oligonucleotide species composition to be sequentially deblocked to allow multiple rounds of extension.

When desired, the nucleic acid can be modified to include a detectable feature or blocking moiety using any method known to one of skill in the art. The feature may be incorporated as part of the synthesis, or added on prior to using the oligonucleotide species composition in any of the processes described herein. Incorporation of a detectable feature may be performed either in liquid phase or on solid phase. In some embodiments the detectable feature may be useful for detection of targets. In some embodiments the detectable feature may be useful for the quantification target nucleic acids (e.g., determining copy number of a particular sequence or species of nucleic acid). Any detectable feature suitable for detection of an interaction or biological activity in a system can be appropriately selected and utilized by the artisan. Examples of detectable features are fluorescent labels such as fluorescein, rhodamine, and others (e.g., Anantha, et al., Biochemistry (1998) 37:2709 2714; and Qu & Chaires, Methods Enzymol. (2000) 321:353 369); radioactive isotopes (e.g., 125I, 131I, 35S, 31P, 32P, 33P, 14C, 3H, 7Be, 28Mg, 57Co, 65Zn, 67Cu, 68Ge, 82Sr, 83Rb, 95Tc, 96Tc, 103Pd, 109Cd, and 127Xe); light scattering labels (e.g., U.S. Pat. No. 6,214,560, and commercially available from Genicon Sciences Corporation, CA); chemiluminescent labels and enzyme substrates (e.g., dioxetanes and acridinium esters), enzymic or protein labels (e.g., green fluorescence protein (GFP) or color variant thereof, luciferase, peroxidase); other chromogenic labels or dyes (e.g., cyanine), and other cofactors or biomolecules such as digoxigenin, strepdavidin, biotin (e.g., members of a binding pair such as biotin and avidin for example), affinity capture moieties, 3' blocking agents (e.g., phosphate group, thiol group, phosphorothioate, amino modifier, biotin, biotin-TEG, cholesteryl-TEG, digoxigenin NHS ester, thiol modifier C3 S-S (Disulfide), inverted dT, C3 spacer) and the like. In some embodiments an oligonucleotide species composition may be labeled with an affinity capture moiety. Also included in detectable features are those labels useful for mass modification for detection with mass spectrometry (e.g., matrix-assisted laser desorption ionization (MALDI) mass spectrometry and electrospray (ES) mass spectrometry).

An oligonucleotide species composition also may refer to a polynucleotide sequence that hybridizes to a subsequence of a target nucleic acid or another oligonucleotide species and facilitates the detection of an oligonucleotide, a target nucleic acid or both, and amplification products or extension products, as with molecular beacons, for example. The term "molecular beacon" as used herein refers to detectable molecule, wherein the detectable feature, or property, of the molecule is detectable only under certain specific conditions, thereby enabling it to function as a specific and informative signal. Non-limiting examples of detectable properties are optical properties, electrical properties, magnetic properties, chemical properties and time or speed through an opening of known size.

In some embodiments a molecular beacon can be a single-stranded oligonucleotide capable of forming a stem-loop structure, where the loop sequence may be complementary to a target nucleic acid sequence of interest and is flanked by short complementary arms that can form a stem. The oligonucleotide may be labeled at one end with a fluorophore and at the other end with a quencher molecule. In the stem-loop conformation, energy from the excited fluorophore is transferred to the quencher, through long-range dipole-dipole coupling similar to that seen in fluorescence resonance energy transfer, or FRET, and released as heat instead of light. When the loop sequence is hybridized to a specific target sequence, the two ends of the molecule are separated and the energy from the excited fluorophore is emitted as light, generating a detectable signal. Molecular beacons offer the added advantage that removal of excess probe is unnecessary due to the self-quenching nature of the unhybridized probe. In some embodiments molecular beacon probes can be designed to either discriminate or tolerate mismatches between the loop and target sequences by modulating the relative strengths of the loop-target hybridization and stem formation. As referred to herein, the term "mismatched nucleotide" or a "mismatch" refers to a nucleotide that is not complementary to the target sequence at that position or positions. A probe may have at least one mismatch, but can also have 2, 3, 4, 5, 6 or 7 or more mismatched nucleotides.

In some embodiments the oligonucleotide species compositions described herein can contain internal subsequences that may form stem-loop structures, where the stem-loop sequences are not complementary to any sequence in the template DNA. The Tm of the internal structure is too low for it to form a stem-loop structure, unless the two sides are brought together by the annealing of the 5' and 3' ends to the template (e.g., the reverse of a molecular beacon).

Detection

Relatively short nucleic acid enriched by the methods and compositions described herein can be analyzed, in certain embodiments. For example, the presence, absence or amount of a particular nucleic acid (e.g., target nucleic acid) or subsequence thereof (e.g., polymorphism) may be detected in some embodiments. Thus, polymorphisms, polynucleotide sequences generated, amplified nucleic acid species (e.g. amplicons or amplification products) or detectable products (e.g., extension products), prepared from the foregoing, can be detected by a suitable detection process in some embodiments. Non-limiting examples of methods of detection, quantification, sequencing and the like are; mass detection of mass modified amplicons (e.g., matrix-assisted laser desorption ionization (MALDI) mass spectrometry and electrospray (ES) mass spectrometry), a primer extension method (e.g., iPLEX™; Sequenom, Inc.), microsequencing methods (e.g., a modification of primer extension methodology), ligase sequence determination methods (e.g., U.S. Pat. Nos. 5,679,524 and 5,952,174, and WO 01/27326), mismatch sequence determination methods (e.g., U.S. Pat. Nos. 5,851,770; 5,958,692; 6,110,684; and 6,183,958), direct DNA sequencing, restriction fragment length polymorphism (RFLP analysis), allele specific oligonucleotide (ASO) analysis, methylation-specific PCR (MSPCR), pyrosequencing analysis, acycloprime analysis, Reverse dot blot, GeneChip microarrays, Dynamic allele-specific hybridization (DASH), Peptide nucleic acid (PNA) and locked nucleic acids (LNA) probes, TaqMan, Molecular Beacons, Intercalating dye, FRET primers, AlphaScreen, SNPstream, genetic bit analysis (GBA), Multiplex minisequencing, SNaPshot, GOOD assay, Microarray miniseq, arrayed primer extension (APEX), Microarray primer extension (e.g., microarray sequence determination methods), Tag arrays, Coded microspheres, Template-directed incorporation (TDI), fluorescence polarization, Colorimetric oligonucleotide ligation assay (OLA), Sequence-coded OLA, Microarray ligation, Ligase chain reaction, Padlock probes, Invader assay, hybridization methods (e.g., hybridization using at least one probe, hybridization using at least one fluorescently labeled probe, and the like), conventional dot blot analyses, single strand conformational polymorphism analysis (SSCP, e.g., U.S. Pat. Nos. 5,891,625 and 6,013,499; Orita et al., Proc. Natl. Acad. Sci. U.S.A 86: 27776-2770 (1989)), denaturing gradient gel electrophoresis (DGGE), heteroduplex analysis, mismatch cleavage detection, and techniques described in Sheffield et al., Proc. Natl. Acad. Sci. USA 49: 699-706 (1991), White et al., Genomics 12: 301-306 (1992), Grompe et al., Proc. Natl. Acad. Sci. USA 86: 5855-5892 (1989), and Grompe, Nature Genetics 5: 111-117 (1993), cloning and sequencing, electrophoresis, the use of hybridization probes and quantitative real time polymerase chain reaction (QRT-PCR), digital PCR, nanopore sequencing, chips and combinations thereof. The detection and quantification of alleles or paralogs can be carried out using the "closed-tube" methods described in U.S. patent application Ser. No. 11/950,395, which was filed Dec. 4, 2007. In some embodiments the amount of each amplified nucleic acid species is determined by mass spectrometry, primer extension, sequencing (e.g., any suitable method, for example nanopore or pyrosequencing), Quantitative PCR (Q-PCR or QRT-PCR), digital PCR, combinations thereof, and the like.

In addition to the methods of detection listed above, the following detection methods may also be used to detect amplified nucleic acid species (e.g., target sequences). In some embodiments, the amplified nucleic acid species can be sequenced directly using any suitable nucleic acid sequencing method. Non-limiting examples of nucleic acid sequencing methods useful for process described herein are; pyrosequencing, nanopore based sequencing methods (e.g., sequencing by synthesis), sequencing by ligation, sequencing by hybridization, microsequencing (primer extension based polymorphism detection), and conventional nucleotide sequencing (e.g., dideoxy sequencing using conventional methods).

In some embodiments, the amplified sequence(s) may be cloned prior to sequence analysis. That is, the amplified nucleic acid species may be ligated into a nucleic acid cloning vector by any process known to one of skill in the art. Cloning of the amplified nucleic acid species may be performed by including unique restriction sites in oligonucleotide species subsequences, which can be used to generate a fragment flanked by restriction sites useful for cloning into an appropriately prepared vector, in some embodiments. In certain embodiments blunt-ended cloning can be used to clone amplified nucleic acid species into an appropriately prepared cloning vector. Cloning of the amplified nucleic acid species may be useful for further manipulation, modification, storage, and analysis of the target sequence of interest. In some embodiments, oligonucleotide species compositions may be designed to overlap an SNP site to allow analysis by allele-specific PCR. Allele-specific PCR may be used to discriminate between nucleic acids in a nucleic acid composition (e.g., fetal target in nucleic acid isolated from maternal sample, for example), because only the correctly hybridized primers will be amplified. In some embodiments, the amplified nucleic acid species may be further analyzed by hybridization (e.g., liquid or solid phase hybridization using sequence specific probes, for example).

Amplified nucleic acids (including amplified nucleic acids that result from reverse transcription) may be modified nucleic acids. Reverse transcribed nucleic acids also may be modified nucleic acids. Modified nucleic acids can include nucleotide analogs, and in certain embodiments include a detectable feature and/or a capture agent (e.g., biomolecules or members of a binding pair, as listed below). In some embodiments the detectable feature and the capture agent can be the same moiety. Modified nucleic acids can be detected by detecting a detectable feature or "signal-generating moiety" in some embodiments. The term "signal-generating" as used herein refers to any atom or molecule that can provide a detectable or quantifiable effect and that can be attached to a nucleic acid. In certain embodiments, a detectable feature generates a unique light signal, a fluorescent signal, a luminescent signal, an electrical property, a chemical property, a magnetic property and the like.

Detectable features include, but are not limited to, nucleotides (labeled or unlabelled), compomers, sugars, peptides, proteins, antibodies, chemical compounds, conducting polymers, binding moieties such as biotin, mass tags, colorimetric agents, light emitting agents, chemiluminescent agents, light scattering agents, fluorescent tags, radioactive tags, charge tags (electrical or magnetic charge), volatile tags and hydrophobic tags, biomolecules (e.g., members of a binding pair antibody/antigen, antibody/antibody, antibody/antibody fragment, antibody/antibody receptor, antibody/protein A or protein G, hapten/anti-hapten, biotin/avidin, biotin/streptavidin, folic acid/folate binding protein, vitamin B12/intrinsic factor, chemical reactive group/complementary chemical reactive group (e.g., sulfhydryl/maleimide, sulfhydryl/haloacetyl derivative, amine/isotriocyanate, amine/succinimidyl ester, and amine/sulfonyl halides) and the like, some of which are further described below. In some embodiments a probe or oligonucleotide species may contain a signal-generating moiety that hybridizes to a target and alters the passage of the target nucleic acid through a nanopore, and can generate a signal when released from the target nucleic acid when it passes through the nanopore (e.g., alters the speed or time through a pore of known size).

A solution containing amplicons produced by an amplification process, or a solution containing extension products produced by an extension process, can be subjected to further processing. For example, a solution can be contacted with an agent that removes phosphate moieties from free nucleotides that have not been incorporated into an amplicon or extension product. An example of such an agent is a phosphatase (e.g., alkaline phosphatase). Amplicons and extension products also may be associated with a solid phase, may be washed, may be contacted with an agent that removes a terminal phosphate (e.g., exposure to a phosphatase), may be contacted with an agent that removes a terminal nucleotide (e.g., exonuclease), may be contacted with an agent that cleaves (e.g., endonuclease, ribonuclease), and the like.

Mass spectrometry is a particularly effective method for the detection of nucleic acids (e.g., PCR amplicon, primer extension product, detector probe cleaved from a target nucleic acid). Presence of a target nucleic acid is verified by comparing the mass of the detected signal with the expected mass of the target nucleic acid. The relative signal strength, e.g., mass peak on a spectra, for a particular target nucleic acid indicates the relative population of the target nucleic acid amongst other nucleic acids, thus enabling calculation of a ratio of target to other nucleic acid or sequence copy number directly from the data. For a review of genotyping methods using Sequenom® standard iPLEX™ assay and MassARRAY® technology, see Jurinke, C., Oeth, P., van den Boom, D., "MALDI-TOF mass spectrometry: a versatile tool for high-performance DNA analysis." Mol. Biotechnol. 26, 147-164 (2004); and Oeth, P. et al., "iPLEX™ Assay: Increased Plexing Efficiency and Flexibility for MassARRAY® System through single base primer extension with mass-modified Terminators." SEQUENOM Application Note (2005). For a review of detecting and quantifying target nucleic using cleavable detector probes (e.g., oligonucleotide compositions described herein) that are cleaved during the amplification process and detected by mass spectrometry, see U.S. patent application Ser. No. 11/950,395, which was filed Dec. 4, 2007, and is hereby incorporated by reference. Such approaches may be adapted to detection of chromosome abnormalities using oligonucleotide species compositions and methods described herein.

In some embodiments, amplified nucleic acid species may be detected by (a) contacting the amplified nucleic acid species (e.g., amplicons) with extension oligonucleotide species compositions (e.g., detection or detector oligonucleotides or primers), (b) preparing extended extension oligonucleotide species compositions, and (c) determining the relative amount of the one or more mismatch nucleotides (e.g., SNP that exist between SNP-alleles or paralogous sequences) by analyzing the extended detection oligonucleotide species compositions (e.g., extension oligonucleotides, or detection of extension products). In certain embodiments one or more mismatch nucleotides may be analyzed by mass spectrometry. In some embodiments amplification, using methods described herein, may generate between about 1 to about 100 amplicon sets, about 2 to about 80 amplicon sets, about 4 to about 60 amplicon sets, about 6 to about 40 amplicon sets, and about 8 to about 20 amplicon sets (e.g., about 1, 2, 3, 4, 5, 6, 7, 8, 9, 10, 15, 20, 25, 30, 35, 40, 45, 50, 55, 60, 65, 70, 75, 80, 85, 90, 95, or about 100 amplicon sets).

An example using mass spectrometry for detection of amplicon sets (e.g., sets of amplification products) is presented herein. Amplicons may be contacted (in solution or on solid phase) with a set of oligonucleotides (the same oligonucleotide species compositions used for amplification or different oligonucleotides representative of subsequences in the oligo or target nucleic acid) under hybridization conditions, where: (1) each oligonucleotide in the set comprises a hybridization sequence capable of specifically hybridizing to one amplicon under the hybridization conditions when the amplicon is present in the solution, (2) each oligonucleotide in the set comprises a distinguishable tag located 5' of the hybridization sequence, (3) a feature of the distinguishable tag of one oligonucleotide detectably differs from the features of distinguishable tags of other oligonucleotides in the set; and (4) each distinguishable tag specifically corresponds to a specific amplicon and thereby specifically corresponds to a specific target nucleic acid. The hybridized amplicon and "detection" oligonucleotide species are subjected to nucleotide synthesis conditions that allow extension of the detection oligonucleotide by one or more nucleotides (labeled with a detectable entity or moiety, or unlabeled), where one of the one or more nucleotides can be a terminating nucleotide. In some embodiments one or more of the nucleotides added to the oligonucleotide species may comprises a capture agent. In embodiments where hybridization occurred in solution, capture of the oligo/amplicon to solid support may be desirable. The detectable moieties or entities can be released from the extended detection oligonucleotide species composition, and detection of the moiety determines the presence, absence, copy number of the nucleotide sequence of interest, or in some embodiments can provide information regarding the status of a reaction. In certain embodiments, the extension may be performed once yielding one extended oligonucleotide. In some embodiments, the extension may be performed multiple times (e.g., under amplification conditions) yielding multiple copies of the extended oligonucleotide. In some embodiments performing the extension multiple times can produce a sufficient number of copies such that interpretation of signals, representing copy number of a particular sequence, can be made with a confidence level of 95% or more (e.g., confidence level of 95% or more, 96% or more, 97% or more, 98% or more, 99% or more, or a confidence level of 99.5% or more). In some embodiments, the method for detecting amplicon sets can be used to detect extension products.

Methods provided herein allow for high-throughput detection of nucleic acid species in a plurality of nucleic acids (e.g., nucleotide sequence species, amplified nucleic acid species and detectable products generated from the foregoing). Multiplexing refers to the simultaneous detection of more than one nucleic acid species. General methods for performing multiplexed reactions in conjunction with mass spectrometry are known (see, e.g., U.S. Pat. Nos. 6,043,031, 5,547,835 and International PCT application No. WO 97/37041). Multiplexing provides an advantage that a plurality of nucleic acid species (e.g., some having different sequence variations) can be identified in as few as a single mass spectrum, as compared to having to perform a separate mass spectrometry analysis for each individual target nucleic acid species. Methods provided herein lend themselves to high-throughput, highly automated processes for analyzing sequence variations with high speed and accuracy, in some embodiments. In certain embodiments, methods herein may be multiplexed at high levels in a single reaction.

Microarrays may be adapted for use with oligonucleotide species compositions and method embodiments described herein. A microarray can be utilized for determining whether a polymorphic variant is present or absent in a nucleic acid sample. A microarray may include any oligonucleotides species compositions described herein, and methods for making and using oligonucleotide microarrays suitable for prognostic use are disclosed in U.S. Pat. Nos. 5,492,806; 5,525,464; 5,589,330; 5,695,940; 5,849,483; 6,018,041; 6,045,996; 6,136,541; 6,142,681; 6,156,501; 6,197,506; 6,223,127; 6,225,625; 6,229,911; 6,239,273; WO 00/52625; WO 01/25485; and WO 01/29259. The microarray typically comprises a solid support and the oligonucleotides may be linked to this solid support by covalent bonds or by non-covalent interactions. The oligonucleotides may also be linked to the solid support directly or by a spacer molecule. A microarray may comprise one or more oligonucleotides complementary to a polymorphic target nucleic acid site. Microarrays may be used with multiplexed protocols described herein.

In certain embodiments, the number of nucleic acid species multiplexed include, without limitation, about 1 to about 500 (e.g., about 1-3, 3-5, 5-7, 7-9, 9-11, 11-13, 13-15, 15-17, 17-19, 19-21, 21-23, 23-25, 25-27, 27-29, 29-31, 31-33, 33-35, 35-37, 37-39, 39-41, 41-43, 43-45, 45-47, 47-49, 49-51, 51-53, 53-55, 55-57, 57-59, 59-61, 61-63, 63-65, 65-67, 67-69, 69-71, 71-73, 73-75, 75-77, 77-79, 79-81, 81-83, 83-85, 85-87, 87-89, 89-91, 91-93, 93-95, 95-97, 97-101, 101-103, 103-105, 105-107, 107-109, 109-111, 111-113, 113-115, 115-117, 117-119, 121-123, 123-125, 125-127, 127-129, 129-131, 131-133, 133-135, 135-137, 137-139, 139-141, 141-143, 143-145, 145-147, 147-149, 149-151, 151-153, 153-155, 155-157, 157-159, 159-

161, 161-163, 163-165, 165-167, 167-169, 169-171, 171-173, 173-175, 175-177, 177-179, 179-181, 181-183, 183-185, 185-187, 187-189, 189-191, 191-193, 193-195, 195-197, 197-199, 199-201, 201-203, 203-205, 205-207, 207-209, 209-211, 211-213, 213-215, 215-217, 217-219, 219-221, 221-223, 223-225, 225-227, 227-229, 229-231, 231-233, 233-235, 235-237, 237-239, 239-241, 241-243, 243-245, 245-247, 247-249, 249-251, 251-253, 253-255, 255-257, 257-259, 259-261, 261-263, 263-265, 265-267, 267-269, 269-271, 271-273, 273-275, 275-277, 277-279, 279-281, 281-283, 283-285, 285-287, 287-289, 289-291, 291-293, 293-295, 295-297, 297-299, 299-301, 301-303, 303-305, 305-307, 307-309, 309-311, 311-313, 313-315, 315-317, 317-319, 319-321, 321-323, 323-325, 325-327, 327-329, 329-331, 331-333, 333-335, 335-337, 337-339, 339-341, 341-343, 343-345, 345-347, 347-349, 349-351, 351-353, 353-355, 355-357, 357-359, 359-361, 361-363, 363-365, 365-367, 367-369, 369-371, 371-373, 373-375, 375-377, 377-379, 379-381, 381-383, 383-385, 385-387, 387-389, 389-391, 391-393, 393-395, 395-397, 397-401, 401-403, 403-405, 405-407, 407-409, 409-411, 411-413, 413-415, 415-417, 417-419, 419-421, 421-423, 423-425, 425-427, 427-429, 429-431, 431-433, 433-435, 435-437, 437-439, 439-441, 441-443, 443-445, 445-447, 447-449, 449-451, 451-453, 453-455, 455-457, 457-459, 459-461, 461-463, 463-465, 465-467, 467-469, 469-471, 471-473, 473-475, 475-477, 477-479, 479-481, 481-483, 483-485, 485-487, 487-489, 489-491, 491-493, 493-495, 495-497, 497-501).

Design methods for achieving resolved mass spectra with multiplexed assays often include primer and oligonucleotide species composition design methods and reaction design methods. For primer and oligonucleotide species composition design in multiplexed assays, the same general guidelines for oligonucleotide species composition design apply for uniplexed reactions. The oligonucleotide species compositions described herein are designed to minimize or eliminate artifacts, thus avoiding false priming and primer dimers, the only difference being more oligonucleotides species are involved for multiplex reactions. For mass spectrometry applications, analyte peaks in the mass spectra for one assay are sufficiently resolved from a product of any assay with which that assay is multiplexed, including pausing peaks and any other by-product peaks. Also, analyte peaks optimally fall within a user-specified mass window, for example, within a range of 5,000-8,500 Da. In some embodiments multiplex analysis may be adapted to mass spectrometric detection of chromosome abnormalities, for example. In certain embodiments multiplex analysis may be adapted to various single nucleotide or nanopore based sequencing methods described herein. Commercially produced micro-reaction chambers or devices or arrays or chips may be used to facilitate multiplex analysis, and are commercially available.

Nucleotide sequence species, amplified nucleic acid species, or detectable products generated from the foregoing may be subject to sequence analysis. The term "sequence analysis" as used herein refers to determining a nucleotide sequence of an extension or amplification product. The entire sequence or a partial sequence of an extension or amplification product can be determined, and the determined nucleotide sequence is referred to herein as a "read." For example, one-time "primer extension" products or linear amplification products may be analyzed directly without further amplification in some embodiments (e.g., by using single-molecule sequencing methodology (described in greater detail hereafter)). In certain embodiments, linear amplification products may be subject to further amplification and then analyzed (e.g., using sequencing by ligation or pyrosequencing methodology (described in greater detail hereafter)). Reads may be subject to different types of sequence analysis. Any suitable sequencing method can be utilized to detect, and determine the amount of, nucleotide sequence species, amplified nucleic acid species, or detectable products generated from the foregoing. Examples of certain sequencing methods are described hereafter.

The terms "sequence analysis apparatus" and "sequence analysis component(s)" used herein refer to apparatus, and one or more components used in conjunction with such apparatus, that can be used by a person of ordinary skill to determine a nucleotide sequence from amplification products resulting from processes described herein (e.g., linear and/or exponential amplification products). Examples of sequencing platforms include, without limitation, the 454 platform (Roche) (Margulies, M. et al. 2005 Nature 437, 376-380), Illumina Genomic Analyzer (or Solexa platform) or SOLID System (Applied Bios stems) or the Helicos True Single Molecule DNA sequencing technology (Harris T D et al. 2008 Science, 320, 106-109), the single molecule, real-time (SMRT™) technology of Pacific Biosciences, and nanopore sequencing (Soni GV and Meller A. 2007 Clin Chem 53: 1996-2001). Such platforms allow sequencing of many nucleic acid molecules isolated from a specimen at high orders of multiplexing in a parallel manner (Dear Brief Funct Genomic Proteomic 2003; 1: 397-416). Each of these platforms allows sequencing of clonally expanded or non-amplified single molecules of nucleic acid fragments. Certain platforms involve, for example, (i) sequencing by ligation of dye-modified probes (including cyclic ligation and cleavage), (ii) pyrosequencing, and (iii) single-molecule sequencing. Nucleotide sequence species, amplification nucleic acid species and detectable products generated there from can be considered a "study nucleic acid" for purposes of analyzing a nucleotide sequence by such sequence analysis platforms.

Sequencing by ligation is a nucleic acid sequencing method that relies on the sensitivity of DNA ligase to base-pairing mismatch. DNA ligase joins together ends of DNA that are correctly base paired. Combining the ability of DNA ligase to join together only correctly base paired DNA ends, with mixed pools of fluorescently labeled oligonucleotides or primers, enables sequence determination by fluorescence detection. Longer sequence reads may be obtained by including primers containing cleavable linkages that can be cleaved after label identification. Cleavage at the linker removes the label and regenerates the 5' phosphate on the end of the ligated oligonucleotide species, preparing the oligonucleotide for another round of ligation. In some embodiments oligonucleotide species compositions may be labeled with more than one fluorescent label (e.g., 1 fluorescent label, 2, 3, or 4 fluorescent labels).

An example of a system that can be used by a person of ordinary skill based on sequencing by ligation generally involves the following steps. Clonal bead populations can be prepared in emulsion microreactors containing target nucleic acid sequences ("template"), amplification reaction components (e.g., including cleavage reaction components where applicable), beads and oligonucleotide species compositions described herein. After amplification, templates are denatured and bead enrichment is performed to separate beads with extended templates from undesired beads (e.g., beads with no extended templates). The template on the selected beads undergoes a 3' modification to allow covalent bonding to the slide, and modified beads can be deposited onto a glass slide. Deposition chambers offer the ability to segment a slide into one, four or eight chambers during the bead loading process. For sequence analysis, primers hybridize to the adapter sequence. A set of four-color dye-labeled probes competes for ligation to the sequencing oligonucleotide species. Specificity of probe ligation is achieved by interrogating every 4th and 5th base during the ligation series. Five to seven rounds of ligation, detection and cleavage record the color at every 5th position with the number of rounds determined by the type of library used. Following each round of ligation, a new complimentary primer offset by one base in the 5' direction is laid down for another series of ligations. Oligonucleotide species reset and ligation rounds (5-7 ligation cycles per round) are repeated sequentially five times to generate 25-35 base pairs of sequence for a single tag. With mate-paired sequencing, this process is repeated for a second tag. Such a system can be used to exponentially amplify amplification products generated by a process described herein, e.g., by ligating a heterologous nucleic acid to the first amplification product generated by a process described herein and performing emulsion amplification using the same or a different solid support originally used to generate the first amplification product. Such a system also may be used to analyze amplification products directly generated by a process described herein by bypassing an exponential amplification process and directly sorting the solid supports described herein on the glass slide.

Pyrosequencing is a nucleic acid sequencing method based on sequencing by synthesis, which relies on detection of a pyrophosphate released on nucleotide incorporation. Generally, sequencing by synthesis involves synthesizing, one nucleotide at a time, a DNA strand complimentary to the strand whose sequence is being sought. Target nucleic acids may be immobilized to a solid support, hybridized with a sequencing oligonucleotide species (e.g., oligonucleotide species compositions described herein, for example), incubated with DNA polymerase, an appropriate endonuclease, ATP sulfurylase, luciferase, apyrase, adenosine 5' phosphsulfate and luciferin. Nucleotide solutions are sequentially added and removed. Correct incorporation of a nucleotide releases a pyrophosphate, which interacts with ATP sulfurylase and produces ATP in the presence of adenosine 5' phosphsulfate, fueling the luciferin reaction, which produces a chemiluminescent signal allowing sequence determination. The amount of light generated is proportional to the number of bases added. Accordingly, the sequence downstream of the sequencing oligonucleotide species can be determined.

An example of a system that can be used by a person of ordinary skill based on pyrosequencing generally involves the following steps: ligating an adaptor nucleic acid to a study nucleic acid and hybridizing the study nucleic acid to a bead; amplifying a nucleotide sequence in the study nucleic acid in an emulsion; sorting beads using a picoliter multiwell solid support; and sequencing amplified nucleotide sequences by pyrosequencing methodology (e.g., Nakano et al., "Single-molecule PCR using water-in-oil emulsion;" Journal of Biotechnology 102: 117-124 (2003)). Such a system can be used to exponentially amplify amplification products generated by a process described herein, e.g., by ligating a heterologous nucleic acid to the first amplification product generated by a process described herein.

Certain single-molecule sequencing embodiments are based on the principal of sequencing by synthesis, and utilize single-pair Fluorescence Resonance Energy Transfer (single pair FRET) as a mechanism by which photons are emitted as a result of successful nucleotide incorporation. The emitted photons often are detected using intensified or high sensitivity cooled charge-couple-devices in conjunction with total internal reflection microscopy (TIRM). Photons are only emitted when the introduced reaction solution contains the correct nucleotide for incorporation into the growing nucleic acid chain that is synthesized as a result of the sequencing process. In FRET based single-molecule sequencing, energy is transferred between two fluorescent dyes, sometimes polymethine cyanine dyes Cy3 and Cy5, through long-range dipole interactions. The donor is excited at its specific excitation wavelength and the excited state energy is transferred, non-radiatively to the acceptor dye, which in turn becomes excited. The acceptor dye eventually returns to the ground state by radiative emission of a photon. The two dyes used in the energy transfer process represent the "single pair", in single pair FRET. Cy3 often is used as the donor fluorophore and often is incorporated as the first labeled nucleotide. Cy5 often is used as the acceptor fluorophore and is used as the nucleotide label for successive nucleotide additions after incorporation of a first Cy3 labeled nucleotide. The fluorophores generally are within 10 nanometers of each for energy transfer to occur successfully.

An example of a system that can be used based on single-molecule sequencing generally involves hybridizing an oligonucleotide species to a target nucleic acid sequence to generate a complex; associating the complex with a solid phase; iteratively extending the oligonucleotide species by a nucleotide tagged with a fluorescent molecule; and capturing an image of fluorescence resonance energy transfer signals after each iteration (e.g., U.S. Pat. No. 7,169,314; Braslavsky et al., PNAS 100(7): 3960-3964 (2003)). Such a system can be used to directly sequence amplification products (linearly or exponentially amplified products) generated by processes described herein. In some embodiments the amplification products can be hybridized to an oligonucleotide that contains sequences complementary to immobilized capture sequences present on a solid support, a bead or glass slide for example. Hybridization of the oligonucleotide species—amplification product complexes with the immobilized capture sequences, immobilizes amplification products to solid supports for single pair FRET based sequencing by synthesis. The oligonucleotide species often is fluorescent, so that an initial reference image of the surface of the slide with immobilized nucleic acids can be generated. The initial reference image is useful for determining locations at which true nucleotide incorporation is occurring. Fluorescence signals detected in array locations not initially identified in the "primer only" reference image are discarded as non-specific fluorescence. Following immobilization of the oligonucleotide species—amplification product complexes, the bound nucleic acids often are sequenced in parallel by the iterative steps of, a) polymerase extension in the presence of one fluorescently labeled nucleotide, b) detection of fluorescence using appropriate microscopy, TIRM for example, c) removal of fluorescent nucleotide, and d) return to step a with a different fluorescently labeled nucleotide.

In some embodiments, nucleotide sequencing may be by solid phase single nucleotide sequencing methods and processes. Solid phase single nucleotide sequencing methods involve contacting target nucleic acid and solid support under conditions in which a single molecule of sample nucleic acid hybridizes to a single molecule of a solid support. Such conditions can include providing the solid support molecules and a single molecule of target nucleic acid in a "microreactor." Such conditions also can include providing a mixture in which the target nucleic acid molecule can hybridize to solid phase nucleic acid on the solid support. Single nucleotide sequencing methods useful in the embodiments described herein are described in U.S. Provisional Patent Application Ser. No. 61/021,871 filed Jan. 17, 2008.

In certain embodiments, nanopore sequencing detection methods include (a) contacting a target nucleic acid for sequencing ("base nucleic acid," e.g., linked probe molecule) with sequence-specific detectors (e.g., oligonucleotide species compositions described herein), under conditions in which the detectors specifically hybridize to substantially complementary subsequences of the base nucleic acid; (b) detecting signals from the detectors and (c) determining the sequence of the base nucleic acid according to the signals detected. In certain embodiments, the detectors hybridized to the base nucleic acid are disassociated from the base nucleic acid (e.g., sequentially dissociated) when the detectors interfere with a nanopore structure as the base nucleic acid passes through a pore, and the detectors disassociated from the base sequence are detected. In some embodiments, a detector disassociated from a base nucleic acid emits a detectable signal, and the detector hybridized to the base nucleic acid emits a different detectable signal or no detectable signal. In certain embodiments, nucleotides in a nucleic acid (e.g., linked probe molecule) are substituted with specific nucleotide sequences corresponding to specific nucleotides ("nucleotide representatives"), thereby giving rise to an expanded nucleic acid (e.g., U.S. Pat. No. 6,723,513), and the detectors hybridize to the nucleotide representatives in the expanded nucleic acid, which serves as a base nucleic acid. In such embodiments, nucleotide representatives may be arranged in a binary or higher order arrangement (e.g., Soni and Meller, Clinical Chemistry 53(11): 1996-2001 (2007)). In some embodiments, a nucleic acid is not expanded, does not give rise to an expanded nucleic acid, and directly serves a base nucleic acid (e.g., a linked probe molecule serves as a non-expanded base nucleic acid), and detectors are directly contacted with the base nucleic acid. For example, a first detector may hybridize to a first subsequence and a second detector may hybridize to a second subsequence, where the first detector and second detector each have detectable labels that can be distinguished from one another, and where the signals from the first detector and second detector can be distinguished from one another when the detectors are disassociated from the base nucleic acid. In certain embodiments, detectors include a region that hybridizes to the base nucleic acid (e.g., two regions), which can be about 3 to about 100 nucleotides in length (e.g., about 4, 5, 6, 7, 8, 9, 10, 11, 12, 13, 14, 15, 16, 17, 18, 19, 20, 25, 30, 35, 40, 50, 55, 60, 65, 70, 75, 80, 85, 90, or 95 nucleotides in length). A detector also may include one or more regions of nucleotides that do not hybridize to the base nucleic acid. In some embodiments, a detector is a molecular beacon. In some embodiments a detector can be an oligonucleotide species composition having an internal stem-loop that can function as a detectable feature when cleaved from the intact oligonucleotide species composition, as described herein. A detector often comprises one or more detectable features independently selected from those described herein. Each detectable feature or label can be detected by any convenient detection process capable of detecting a signal generated by each label (e.g., magnetic, electric, chemical, optical and the like). For example, a CD camera can be used to detect signals from one or more distinguishable quantum dots linked to a detector.

In certain sequence analysis embodiments, reads may be used to construct a larger nucleotide sequence, which can be facilitated by identifying overlapping sequences in different reads and by using identification sequences in the reads. Such sequence analysis methods and software for constructing larger sequences from reads are known to the person of ordinary skill (e.g., Venter et al., Science 291: 1304-1351 (2001)). Specific reads, partial nucleotide sequence constructs, and full nucleotide sequence constructs may be compared between nucleotide sequences within a sample nucleic acid (i.e., internal comparison) or may be compared with a reference sequence (i.e., reference comparison) in certain sequence analysis embodiments. Internal comparisons sometimes are performed in situations where a sample nucleic acid is prepared from multiple samples or from a single sample source that contains sequence variations. Reference comparisons sometimes are performed when a reference nucleotide sequence is known and an objective is to determine whether a sample nucleic acid contains a nucleotide sequence that is substantially similar or the same, or different, than a reference nucleotide sequence. Sequence analysis can be facilitated by the use of sequence analysis apparatus and components described above.

Target nucleic acid sequences also can be detected using standard electrophoretic techniques. Although the detection step can sometimes be preceded by an amplification step, amplification is not required in the embodiments described herein. Examples of methods for detection and quantification of target nucleic acid sequences using electrophoretic techniques can be found in the art. A non-limiting example is presented herein. After running a sample (e.g., mixed nucleic acid sample isolated from maternal serum, or amplification nucleic acid species, for example) in an agarose or polyacrylamide gel, the gel may be labeled (e.g., stained) with ethidium bromide (see, Sambrook and Russell, Molecular Cloning: A Laboratory Manual 3d ed., 2001). The presence of a band of the same size as the standard control is an indication of the presence of a target nucleic acid sequence, the amount of which may then be compared to the control based on the intensity of the band, thus detecting and quantifying the target sequence of interest. In some embodiments, restriction enzymes capable of distinguishing between maternal and paternal alleles may be used to detect and quantify target nucleic acid species. In certain embodiments, oligonucleotide species compositions specific to target nucleic acids (e.g., a specific allele, for example) can be used to detect the presence of the target sequence of interest. The oligonucleotides can also be used to indicate the amount of the target nucleic acid molecules in comparison to the standard control, based on the intensity of signal imparted by the oligonucleotide species.

Sequence-specific oligonucleotide species hybridization can be used to detect a particular nucleic acid in a mixture or mixed population comprising other species of nucleic acids. Under sufficiently stringent hybridization conditions, the oligonucleotide species (e.g., probes) hybridize specifically only to substantially complementary sequences. The stringency of the hybridization conditions can be relaxed to tolerate varying amounts of sequence mismatch. A number of hybridization formats are known in the art, which include but are not limited to, solution phase, solid phase, or mixed phase hybridization assays. The following documents provide an overview of the various hybridization assay formats: Singer et al., Biotechniques 4:230, 1986; Haase et al., Methods in Virology, pp. 189-226, 1984; Wilkinson, In situ Hybridization, Wilkinson ed., IRL Press, Oxford University Press, Oxford; and Hames and Higgins eds., Nucleic Acid Hybridization: A Practical Approach, IRL Press, 1987.

Hybridization complexes can be detected by techniques known in the art. Nucleic acid probes (e.g., oligonucleotide species) capable of specifically hybridizing to a target nucleic acid (e.g., mRNA or amplified DNA) can be labeled by any suitable method, and the labeled probe used to detect the presence of hybridized nucleic acids. One commonly used method of detection is autoradiography, using probes labeled with 3H, 125I, 35S, 14C, 32P, or the like. The choice of radioactive isotope depends on research preferences due to ease of synthesis, stability, and half-lives of the selected isotopes. Other labels include compounds (e.g., biotin and digoxigenin), which bind to antiligands or antibodies labeled with fluorophores, chemiluminescent agents, and enzymes. In some embodiments, probes can be conjugated directly with labels such as fluorophores, chemiluminescent agents or enzymes. The choice of label depends on sensitivity required, ease of conjugation with the probe, stability requirements, and available instrumentation.

"Primer extension" polymorphism detection methods also referred to herein as "microsequencing" methods, typically are carried out by hybridizing a complementary oligonucleotide species to a nucleic acid carrying the polymorphic site. In these methods, the oligonucleotide typically hybridizes adjacent to the polymorphic site. The term "adjacent" as used in reference to "microsequencing" methods, refers to the 3' end of the extension oligonucleotide being sometimes 1 nucleotide from the 5' end of the polymorphic site, often 2 or 3, and at times 4, 5, 6, 7, 8, 9, or 10 nucleotides from the 5' end of the polymorphic site, in the nucleic acid when the extension oligonucleotide is hybridized to the nucleic acid. The extension oligonucleotide then is extended by one or more nucleotides, often 1, 2, or 3 nucleotides, and the number and/or type of nucleotides that are added to the extension oligonucleotide determine which polymorphic variant or variants are present. Oligonucleotide extension methods are disclosed, for example, in U.S. Pat. Nos. 4,656,127; 4,851,331; 5,679,524; 5,834,189; 5,876,934; 5,908,755; 5,912,118; 5,976,802; 5,981,186; 6,004,744; 6,013,431; 6,017,702; 6,046,005; 6,087,095; 6,210,891; and WO 01/20039. The extension products can be detected in any manner, such as by fluorescence methods (see, e.g., Chen & Kwok, Nucleic Acids Research 25: 347-353 (1997) and Chen et al., Proc. Natl. Acad. Sci. USA 94/20: 10756-10761 (1997)) or by mass spectrometric methods (e.g., MALDI-TOF mass spectrometry) and other methods described herein. Oligonucleotide extension methods using mass spectrometry are described, for example, in U.S. Pat. Nos. 5,547,835; 5,605,798; 5,691,141; 5,849,542; 5,869, 242; 5,928,906; 6,043,031; 6,194,144; and 6,258,538.

Microsequencing detection methods often incorporate an amplification process that precedes the extension step. The amplification process typically amplifies a region from a nucleic acid sample that comprises the polymorphic site. Amplification can be carried out utilizing methods described above, below in the example section or for example using a pair of oligonucleotide species compositions described herein, in a polymerase chain reaction (PCR), in which one oligonucleotide species typically is complementary to a region 3' of the polymorphism and the other typically is complementary to a region 5' of the polymorphism. A PCR oligonucleotide species pair may be used in methods disclosed in U.S. Pat. Nos. 4,683,195; 4,683,202, 4,965,188; 5,656,493; 5,998,143; 6,140,054; WO 01/27327; and WO 01/27329 for example. PCR oligonucleotide species pairs may also be used in any commercially available machines that perform PCR, such as any of the GeneAmp® Systems available from Applied Biosystems.

Whole genome sequencing may also be utilized for discriminating alleles of target nucleic acids (e.g., RNA transcripts or DNA), in some embodiments. Examples of whole genome sequencing methods include, but are not limited to, nanopore-based sequencing methods, sequencing by synthesis and sequencing by ligation, as described above.

Data Processing

After conducting an enrichment process described herein, enriched nucleic acid or a subset of the enriched nucleic acid or target nucleic acid thereof (collectively enriched nucleic acid"), may be detected and/or analyzed by any suitable method and any suitable detection device, such as a method or detection device described herein. In some embodiments, one or more target nucleic acids in the enriched nucleic acid may be detected and/or analyzed.

Presence or absence of an outcome can be determined from the detection and/or analysis results. The term "outcome" as used herein refers to a phenotype indicated by the presence, absence or amount of one or more nucleic acids in the enriched nucleic acid. Non-limiting examples of outcomes include presence or absence of a fetus (e.g., pregnancy test), prenatal or neonatal disorder, chromosome abnormality, chromosome aneuploidy (e.g., trisomy 21, trisomy 18, trisomy 13), cell proliferation condition, other disease condition and the like. As described herein, algorithms, software, processors and/or machines, for example, can be utilized to (i) process detection data pertaining to enriched nucleic acid, and/or (ii) identify the presence or absence of an outcome.

Presence or absence of an outcome may be determined for all samples tested, and in some embodiments, presence or absence of a outcome is determined in a subset of the samples (e.g., samples from individual pregnant females). In certain embodiments, an outcome is determined for about 60, 65, 70, 75, 76, 77, 78, 79, 80, 81, 82, 83, 84, 85, 86, 87, 88, 89, 90, 91, 92, 93, 94, 95, 96, 97, 98, 99%, or greater than 99%, of samples analyzed in a set. A set of samples can include any suitable number of samples, and in some embodiments, a set has about 10, 15, 20, 25, 30, 35, 40, 45, 50, 55, 60, 65, 70, 75, 80, 90, 100, 200, 300, 400, 500, 600, 700, 800, 900 or 1000 samples, or more than 1000 samples. The set may be considered with respect to samples tested in a particular period of time, and/or at a particular location. The set may be otherwise defined by, for example, gestational age and/or ethnicity. The set may be comprised of a sample which is subdivided into subsamples or replicates all or some of which may be tested. The set may comprise a sample from the same subject collected at two different times. In certain embodiments, an outcome is determined about 60% or more of the time for a given sample analyzed (e.g., about 65, 70, 75, 76, 77, 78, 79, 80, 81, 82, 83, 84, 85, 86, 87, 88, 89, 90, 91, 92, 93, 94, 95, 96, 97, 98, 99%, or more than 99% of the time for a given sample). In certain embodiments, analyzing a higher number of characteristics (e.g., sequence variations) that discriminate alleles can increase the percentage of outcomes determined for the samples (e.g., discriminated in a multiplex analysis). In some embodiments, one or more tissue or fluid samples (e.g., one or more blood samples) are provided by a subject (e.g., pregnant female). In certain embodiments, one or more RNA or DNA samples, or two or more replicate RNA or DNA samples, are isolated from a single tissue or fluid sample, and analyzed by methods described herein.

Presence or absence of an outcome can be expressed in any suitable form, and in conjunction with any suitable variable, collectively including, without limitation, ratio, deviation in ratio, frequency, distribution, probability (e.g., odds ratio, p-value), likelihood, percentage, value over a threshold, or risk factor, associated with the presence of a outcome for a subject or sample. An outcome may be provided with one or more variables, including, but not limited to, sensitivity, specificity, standard deviation, probability, ratio, coefficient of variation (CV), threshold, score, probability, confidence level, or combination of the foregoing, in certain embodiments.

In certain embodiments, one or more of ratio, sensitivity, specificity and/or confidence level are expressed as a percentage. In some embodiments, the percentage, independently for each variable, is greater than about 90% (e.g., about 90, 91, 92, 93, 94, 95, 96, 97, 98 or 99%, or greater than 99% (e.g., about 99.5%, or greater, about 99.9% or greater, about 99.95% or greater, about 99.99% or greater)). Coefficient of variation (CV) in some embodiments is expressed as a percentage, and sometimes the percentage is about 10% or less (e.g., about 10, 9, 8, 7, 6, 5, 4, 3, 2 or 1%, or less than 1% (e.g., about 0.5% or less, about 0.1% or less, about 0.05% or less, about 0.01% or less)). A probability (e.g., that a particular outcome determined by an algorithm is not due to chance) in certain embodiments is expressed as a p-value, and sometimes the p-value is about 0.05 or less (e.g., about 0.05, 0.04, 0.03, 0.02 or 0.01, or less than 0.01 (e.g., about 0.001 or less, about 0.0001 or less, about 0.00001 or less, about 0.000001 or less)).

For example, scoring or a score may refer to calculating the probability that a particular outcome is actually present or absent in a subject/sample. The value of a score may be used to determine for example the variation, difference, or ratio of amplified nucleic detectable product that may correspond to the actual outcome. For example, calculating a positive score from detectable products can lead to an identification of an outcome, which is particularly relevant to analysis of single samples.

In certain embodiments, simulated (or simulation) data can aid data processing for example by training an algorithm or testing an algorithm. Simulated data may for instance involve hypothetical various samples of different concentrations of fetal and maternal nucleic acid in serum, plasma and the like. Simulated data may be based on what might be expected from a real population or may be skewed to test an algorithm and/or to assign a correct classification based on a simulated data set. Simulated data also is referred to herein as "virtual" data. Fetal/maternal contributions within a sample can be simulated as a table or array of numbers (for example, as a list of peaks corresponding to the mass signals of enriched nucleic acids of a reference biomolecule or amplified nucleic acid sequence), as a mass spectrum, as a pattern of bands on a gel, label intensity, or as a representation of any technique that measures mass distribution. Simulations can be performed in most instances by a computer program. One possible step in using a simulated data set is to evaluate the confidence of the identified results, i.e. how well the selected positives/negatives match the sample and whether there are additional variations. A common approach is to calculate the probability value (p-value) which estimates the probability of a random sample having better score than the selected one. As p-value calculations can be prohibitive in certain circumstances, an empirical model may be assessed, in which it is assumed that at least one sample matches a reference sample (with or without resolved variations). Alternatively other distributions such as Poisson distribution can be used to describe the probability distribution.

In certain embodiments, an algorithm can assign a confidence value to the true positives, true negatives, false positives and false negatives calculated. The assignment of a likelihood of the occurrence of a outcome can also be based on a certain probability model.

Simulated data often is generated in an in silico process. As used herein, the term "in silico" refers to research and experiments performed using a computer. In silico methods include, but are not limited to, molecular modeling studies, karyotyping, genetic calculations, biomolecular docking experiments, and virtual representations of molecular structures and/or processes, such as molecular interactions.

As used herein, a "data processing routine" refers to a process that can be embodied in software that determines the biological significance of acquired data (i.e., the ultimate results of an assay). For example, a data processing routine can determine the amount of each nucleotide sequence species based upon the data collected. A data processing routine also may control an instrument and/or a data collection routine based upon results determined. A data processing routine and a data collection routine often are integrated and provide feedback to operate data acquisition by the instrument, and hence provide assay-based judging methods provided herein.

As used herein, software refers to computer readable program instructions that, when executed by a computer, perform computer operations. Typically, software is provided on a program product containing program instructions recorded on a computer readable medium, including, but not limited to, magnetic media including floppy disks, hard disks, and magnetic tape; and optical media including CD-ROM discs, DVD discs, magneto-optical discs, and other such media on which the program instructions can be recorded.

Different methods of predicting abnormality or normality can produce different types of results. For any given prediction, there are four possible types of outcomes: true positive, true negative, false positive or false negative. The term "true positive" as used herein refers to a subject correctly diagnosed as having a outcome. The term "false positive" as used herein refers to a subject wrongly identified as having a outcome. The term "true negative" as used herein refers to a subject correctly identified as not having a outcome. The term "false negative" as used herein refers to a subject wrongly identified as not having a outcome. Two measures of performance for any given method can be calculated based on the ratios of these occurrences: (i) a sensitivity value, the fraction of predicted positives that are correctly identified as being positives (e.g., the fraction of nucleotide sequence sets correctly identified by level comparison detection/determination as indicative of outcome, relative to all nucleotide sequence sets identified as such, correctly or incorrectly), thereby reflecting the accuracy of the results in detecting the outcome; and (ii) a specificity value, the fraction of predicted negatives correctly identified as being negative (the fraction of nucleotide sequence sets correctly identified by level comparison detection/determination as indicative of chromosomal normality, relative to all nucleotide sequence sets identified as such, correctly or incorrectly), thereby reflecting accuracy of the results in detecting the outcome.

The term "sensitivity" as used herein refers to the number of true positives divided by the number of true positives plus the number of false negatives, where sensitivity (sens) may be within the range of $0 \leq sens \leq 1$. Ideally, method embodiments herein have the number of false negatives equaling zero or close to equaling zero, so that no subject is wrongly identified as not having at least one outcome when they indeed have at least one outcome. Conversely, an assessment often is made of the ability of a prediction algorithm to classify negatives correctly, a complementary measurement to sensitivity. The term "specificity" as used herein refers to the number of true negatives divided by the number of true negatives plus the number of false positives, where sensitivity (spec) may be within the range of 0 spec 1. Ideally, methods embodiments herein have the number of false positives equaling zero or close to equaling zero, so that no subject wrongly identified as having at least one outcome when they do not have the outcome being assessed. Hence, a method that has sensitivity and specificity equaling one, or 100%, sometimes is selected.

One or more prediction algorithms may be used to determine significance or give meaning to the detection data collected under variable conditions that may be weighed independently of or dependently on each other. The term "variable" as used herein refers to a factor, quantity, or function of an algorithm that has a value or set of values. For example, a variable may be the design of a set of amplified nucleic acid species, the number of sets of amplified nucleic acid species, percent fetal genetic contribution tested, percent maternal genetic contribution tested, type of outcome assayed, type of sex-linked abnormalities assayed, the age of the mother and the like. The term "independent" as used herein refers to not being influenced or not being controlled by another. The term "dependent" as used herein refers to being influenced or controlled by another. For example, a particular chromosome and a trisomy event occurring for the particular chromosome that results in a viable being are variables that are dependent upon each other.

Any suitable type of method or prediction algorithm may be utilized to give significance to the data of the present technology within an acceptable sensitivity and/or specificity. For example, prediction algorithms such as Mann-Whitney U Test, binomial test, log odds ratio, Chi-squared test, z-test, t-test, ANOVA (analysis of variance), regression analysis, neural nets, fuzzy logic, Hidden Markov Models, multiple model state estimation, and the like may be used. One or more methods or prediction algorithms may be determined to give significance to the data having different independent and/or dependent variables of the present technology. And one or more methods or prediction algorithms may be determined not to give significance to the data having different independent and/or dependent variables of the present technology. One may design or change parameters of the different variables of methods described herein based on results of one or more prediction algorithms (e.g., number of sets analyzed, types of nucleotide species in each set). For example, applying the Chi-squared test to detection data may suggest that specific ranges of maternal age are correlated to a higher likelihood of having an offspring with a specific outcome, hence the variable of maternal age may be weighed differently verses being weighed the same as other variables.

In certain embodiments, several algorithms may be chosen to be tested. These algorithms then can be trained with raw data. For each new raw data sample, the trained algorithms will assign a classification to that sample (e.g., trisomy or normal). Based on the classifications of the new raw data samples, the trained algorithms' performance may be assessed based on sensitivity and specificity. Finally, an algorithm with the highest sensitivity and/or specificity or combination thereof may be identified.

For a chromosome abnormality, such as aneuploidy for example, chromosome ratio of about 1:1 is expected for a normal, euploid fetus. In some embodiments a ratio of nucleotide sequence species in a set is expected to be about 1.0:1.0, which can indicate the nucleotide sequence species in the set are in different chromosomes present in the same number in the subject. When nucleotide sequence species in a set are on chromosomes present in different numbers in the subject (for example, in trisomy 21) the set ratio which is detected is lower or higher than about 1.0:1.0. Where extracellular nucleic acid is utilized as template nucleic acid, the measured set ratio often is not 1.0:1.0 (euploid) or 1.0:1.5 (e.g., trisomy 21), due to a variety of factors. The expected measured ratio can vary, so long as such variation is substantially reproducible and detectable. For example, a particular set might provide a reproducible measured ratio (for example of peaks in a mass spectrograph) of 1.0:1.2 in a euploid measurement. The aneuploid measurement for such a set might then be, for example, 1.0:1.3. The, for example, 1.3 versus 1.2 measurement is the result of measuring the fetal nucleic acid against a background of maternal nucleic acid, which decreases the signal that would otherwise be provided by a "pure" fetal sample, such as from amniotic fluid or from a fetal cell.

In certain embodiments, provided are methods for identifying the presence or absence of an outcome that comprise: (a) providing a system, wherein the system comprises distinct software modules, and wherein the distinct software modules comprise a signal detection module, a logic processing module, and a data display organization module; (b) detecting signal information indicating the presence, absence or amount of enriched nucleic acid; (c) receiving, by the logic processing module, the signal information; (d) calling the presence or absence of an outcome by the logic processing module; and (e) organizing, by the data display organization model in response to being called by the logic processing module, a data display indicating the presence or absence of the outcome.

Provided also are methods for identifying the presence or absence of an outcome, which comprise providing signal information indicating the presence, absence or amount of enriched nucleic acid; providing a system, wherein the system comprises distinct software modules, and wherein the distinct software modules comprise a signal detection module, a logic processing module, and a data display organization module; receiving, by the logic processing module, the signal information; calling the presence or absence of an outcome by the logic processing module; and, organizing, by the data display organization model in response to being called by the logic processing module, a data display indicating the presence or absence of the outcome.

Provided also are methods for identifying the presence or absence of an outcome, which comprise providing a system, wherein the system comprises distinct software modules, and wherein the distinct software modules comprise a signal detection module, a logic processing module, and a data display organization module; receiving, by the logic processing module, signal information indicating the presence, absence or amount of enriched nucleic acid; calling the presence or absence of an outcome by the logic processing module; and, organizing, by the data display organization model in response to being called by the logic processing module, a data display indicating the presence or absence of the outcome.

By "providing signal information" is meant any manner of providing the information, including, for example, computer communication means from a local, or remote site, human data entry, or any other method of transmitting signal information. The signal information may be generated in one location and provided to another location.

By "obtaining" or "receiving" signal information is meant receiving the signal information by computer communication means from a local, or remote site, human data entry, or any other method of receiving signal information. The signal information may be generated in the same location at which it is received, or it may be generated in a different location and transmitted to the receiving location.

By "indicating" or "representing" the amount is meant that the signal information is related to, or correlates with, for example, the amount of enriched nucleic acid or presence or absence of enriched nucleic acid. The information may be, for example, the calculated data associated with the presence or absence of enriched nucleic acid as obtained, for example, after converting raw data obtained by mass spectrometry.

Also provided are computer program products, such as, for example, a computer program products comprising a computer usable medium having a computer readable program code embodied therein, the computer readable program code adapted to be executed to implement a method for identifying the presence or absence of an outcome, which comprises (a) providing a system, wherein the system comprises distinct software modules, and wherein the distinct software modules comprise a signal detection module, a logic processing module, and a data display organization module; (b) detecting signal information indicating the presence, absence or amount of enriched nucleic acid; (c) receiving, by the logic processing module, the signal information; (d) calling the presence or absence of an outcome by the logic processing module; and, organizing, by the data display organization model in response to being called by the logic processing module, a data display indicating the presence or absence of the outcome.

Also provided are computer program products, such as, for example, computer program products comprising a computer usable medium having a computer readable program code embodied therein, the computer readable program code adapted to be executed to implement a method for identifying the presence or absence of an outcome, which comprises providing a system, wherein the system comprises distinct software modules, and wherein the distinct software modules comprise a signal detection module, a logic processing module, and a data display organization module; receiving signal information indicating the presence, absence or amount of enriched nucleic acid; calling the presence or absence of an outcome by the logic processing module; and, organizing, by the data display organization model in response to being called by the logic processing module, a data display indicating the presence or absence of the outcome.

Signal information may be, for example, mass spectrometry data obtained from mass spectrometry of a enriched nucleic acid, or of amplified nucleic acid. As the enriched nucleic acid may be amplified into a nucleic acid that is detected, the signal information may be detection information, such as mass spectrometry data, obtained from enriched nucleic acid or stoichiometrically amplified nucleic acid from the enriched nucleic acid, for example. The mass spectrometry data may be raw data, such as, for example, a set of numbers, or, for example, a two dimensional display of the mass spectrum. The signal information may be converted or transformed to any form of data that may be provided to, or received by, a computer system. The signal information may also, for example, be converted, or transformed to identification data or information representing an outcome. An outcome may be, for example, a fetal allelic ratio, or a particular chromosome number in fetal cells. Where the chromosome number is greater or less than in euploid cells, or where, for example, the chromosome number for one or more of the chromosomes, for example, 21, 18, or 13, is greater than the number of other chromosomes, the presence of a chromosomal disorder may be identified.

Also provided is a machine for identifying the presence or absence of an outcome wherein the machine comprises a computer system having distinct software modules, and wherein the distinct software modules comprise a signal detection module, a logic processing module, and a data display organization module, wherein the software modules are adapted to be executed to implement a method for identifying the presence or absence of an outcome, which comprises (a) detecting signal information indicating the presence, absence or amount of enriched nucleic acid; (b) receiving, by the logic processing module, the signal information; (c) calling the presence or absence of an outcome by the logic processing module, wherein a ratio of alleles different than a normal ratio is indicative of a chromosomal disorder; and (d) organizing, by the data display organization model in response to being called by the logic processing module, a data display indicating the presence or absence of the outcome. The machine may further comprise a memory module for storing signal information or data indicating the presence or absence of a chromosomal disorder. Also provided are methods for identifying the presence or absence of an outcome, wherein the methods comprise the use of a machine for identifying the presence or absence of an outcome.

Also provided are methods identifying the presence or absence of an outcome that comprises: (a) detecting signal information, wherein the signal information indicates presence, absence or amount of enriched nucleic acid; (b) transforming the signal information into identification data, wherein the identification data represents the presence or absence of the outcome, whereby the presence or absence of the outcome is identified based on the signal information; and (c) displaying the identification data.

Also provided are methods for identifying the presence or absence of an outcome that comprises: (a) providing signal information indicating the presence, absence or amount of enriched nucleic acid; (b) transforming the signal information representing into identification data, wherein the identification data represents the presence or absence of the outcome, whereby the presence or absence of the outcome is identified based on the signal information; and (c) displaying the identification data.

Also provided are methods for identifying the presence or absence of an outcome that comprises: (a) receiving signal information indicating the presence, absence or amount of enriched nucleic acid; (b) transforming the signal information into identification data, wherein the identification data represents the presence or absence of the outcome, whereby the presence or absence of the outcome is identified based on the signal information; and (c) displaying the identification data.

For purposes of these, and similar embodiments, the term "signal information" indicates information readable by any electronic media, including, for example, computers that represent data derived using the present methods. For example, "signal information" can represent the amount of a enriched nucleic acid or amplified nucleic acid. Signal information, such as in these examples, that represents physical substances may be transformed into identification data, such as a visual display that represents other physical substances, such as, for example, a chromosome disorder, or a chromosome number. Identification data may be displayed in any appropriate manner, including, but not limited to, in a computer visual display, by encoding the identification data into computer readable media that may, for example, be transferred to another electronic device (e.g., electronic record), or by creating a hard copy of the display, such as a print out or physical record of information. The information may also be displayed by auditory signal or any other means of information communication. In some embodiments, the signal information may be detection data obtained using methods to detect a enriched nucleic acid.

Once the signal information is detected, it may be forwarded to the logic-processing module. The logic-processing module may "call" or "identify" the presence or absence of an outcome.

Provided also are methods for transmitting genetic information to a subject, which comprise identifying the presence or absence of an outcome wherein the presence or absence of the outcome has been determined from determining the presence, absence or amount of enriched nucleic acid from a sample from the subject; and transmitting the presence or absence of the outcome to the subject. A method may include transmitting prenatal genetic information to a human pregnant female subject, and the outcome may be presence or absence of a chromosome abnormality or aneuploidy, in certain embodiments.

The term "identifying the presence or absence of an outcome" or "an increased risk of an outcome," as used herein refers to any method for obtaining such information, including, without limitation, obtaining the information from a laboratory file. A laboratory file can be generated by a laboratory that carried out an assay to determine the presence or absence of an outcome. The laboratory may be in the same location or different location (e.g., in another country) as the personnel identifying the presence or absence of the outcome from the laboratory file. For example, the laboratory file can be generated in one location and transmitted to another location in which the information therein will be transmitted to the subject. The laboratory file may be in tangible form or electronic form (e.g., computer readable form), in certain embodiments.

The term "transmitting the presence or absence of the outcome to the subject" or any other information transmitted as used herein refers to communicating the information to the subject, or family member, guardian or designee thereof, in a suitable medium, including, without limitation, in verbal, document, or file form.

Also provided are methods for providing to a subject a medical prescription based on genetic information, which comprise identifying the presence or absence of an outcome, wherein the presence or absence of the outcome has been determined from the presence, absence or amount of enriched nucleic acid from a sample from the subject; and providing a medical prescription based on the presence or absence of the outcome to the subject.

The term "providing a medical prescription based on prenatal genetic information" refers to communicating the prescription to the subject, or family member, guardian or designee thereof, in a suitable medium, including, without limitation, in verbal, document or file form.

The medical prescription may be for any course of action determined by, for example, a medical professional upon reviewing the prenatal genetic information. For example, the prescription may be for a pregnant female subject to undergo an amniocentesis procedure. Or, in another example, the medical prescription may be for the subject to undergo another genetic test. In yet another example, the medical prescription may be medical advice to not undergo further genetic testing.

Also provided are files, such as, for example, a file comprising the presence or absence of a chromosomal disorder in the fetus of the pregnant female subject, wherein the presence or absence of the outcome has been determined from the presence, absence or amount of enriched nucleic acid in a sample from the subject.

Also provided are files, such as, for example, a file comprising the presence or absence of outcome for a subject, wherein the presence or absence of the outcome has been determined from the presence, absence or amount of enriched nucleic acid in a sample from the subject. The file may be, for example, but not limited to, a computer readable file, a paper file, or a medical record file.

Computer program products include, for example, any electronic storage medium that may be used to provide instructions to a computer, such as, for example, a removable storage device, CD-ROMS, a hard disk installed in hard disk drive, signals, magnetic tape, DVDs, optical disks, flash drives, RAM or floppy disk, and the like.

The systems discussed herein may further comprise general components of computer systems, such as, for example, network servers, laptop systems, desktop systems, handheld systems, personal digital assistants, computing kiosks, and the like. The computer system may comprise one or more input means such as a keyboard, touch screen, mouse, voice recognition or other means to allow the user to enter data into the system. The system may further comprise one or more output means such as a CRT or LCD display screen, speaker, FAX machine, impact printer, inkjet printer, black and white or color laser printer or other means of providing visual, auditory or hardcopy output of information.

The input and output means may be connected to a central processing unit which may comprise among other components, a microprocessor for executing program instructions and memory for storing program code and data. In some embodiments the methods may be implemented as a single user system located in a single geographical site. In other embodiments methods may be implemented as a multi-user system. In the case of a multi-user implementation, multiple central processing units may be connected by means of a network. The network may be local, encompassing a single department in one portion of a building, an entire building, span multiple buildings, span a region, span an entire country or be worldwide. The network may be private, being owned and controlled by the provider or it may be implemented as an Internet based service where the user accesses a web page to enter and retrieve information.

The various software modules associated with the implementation of the present products and methods can be suitably loaded into the a computer system as desired, or the software code can be stored on a computer-readable medium such as a floppy disk, magnetic tape, or an optical disk, or the like. In an online implementation, a server and web site maintained by an organization can be configured to provide software downloads to remote users. As used herein, "module," including grammatical variations thereof, means, a self-contained functional unit which is used with a larger system. For example, a software module is a part of a program that performs a particular task.

Thus, provided herein is a machine comprising one or more software modules described herein, where the machine can be, but is not limited to, a computer (e.g., server) having a storage device such as floppy disk, magnetic tape, optical disk, random access memory and/or hard disk drive, for example.

The present methods may be implemented using hardware, software or a combination thereof and may be implemented in a computer system or other processing system. An example computer system may include one or more processors. A processor can be connected to a communication bus. The computer system may include a main memory, sometimes random access memory (RAM), and can also include a secondary memory. The secondary memory can include, for example, a hard disk drive and/or a removable storage drive, representing a floppy disk drive, a magnetic tape drive, an optical disk drive, memory card etc. The removable storage drive reads from and/or writes to a removable storage unit in a well-known manner. A removable storage unit includes, but is not limited to, a floppy disk, magnetic tape, optical disk, etc. which is read by and written to by, for example, a removable storage drive. As will be appreciated, the removable storage unit includes a computer usable storage medium having stored therein computer software and/or data.

In alternative embodiments, secondary memory may include other similar means for allowing computer programs or other instructions to be loaded into a computer system. Such means can include, for example, a removable storage unit and an interface device. Examples of such can include a program cartridge and cartridge interface (such as that found in video game devices), a removable memory chip (such as an EPROM, or PROM) and associated socket, and other removable storage units and interfaces which allow software and data to be transferred from the removable storage unit to a computer system.

The computer system may also include a communications interface. A communications interface allows software and data to be transferred between the computer system and external devices. Examples of communications interface can include a modem, a network interface (such as an Ethernet card), a communications port, a PCMCIA slot and card, etc. Software and data transferred via communications interface are in the form of signals, which can be electronic, electromagnetic, optical or other signals capable of being received by communications interface. These signals are provided to communications interface via a channel. This channel carries signals and can be implemented using wire or cable, fiber optics, a phone line, a cellular phone link, an RF link and other communications channels. Thus, in one example, a communications interface may be used to receive signal information to be detected by the signal detection module.

In a related aspect, the signal information may be input by a variety of means, including but not limited to, manual input devices or direct data entry devices (DDEs). For example, manual devices may include, keyboards, concept keyboards, touch sensitive screens, light pens, mouse, tracker balls, joysticks, graphic tablets, scanners, digital cameras, video digitizers and voice recognition devices. DDEs may include, for example, bar code readers, magnetic strip codes, smart cards, magnetic ink character recognition, optical character recognition, optical mark recognition, and turnaround documents. In one embodiment, an output from a gene or chip reader my serve as an input signal.

EXAMPLES

The examples set forth below illustrate certain embodiments and do not limit the technology.

Example 1: Size Selection Based DNA Extraction

Figure 1B:
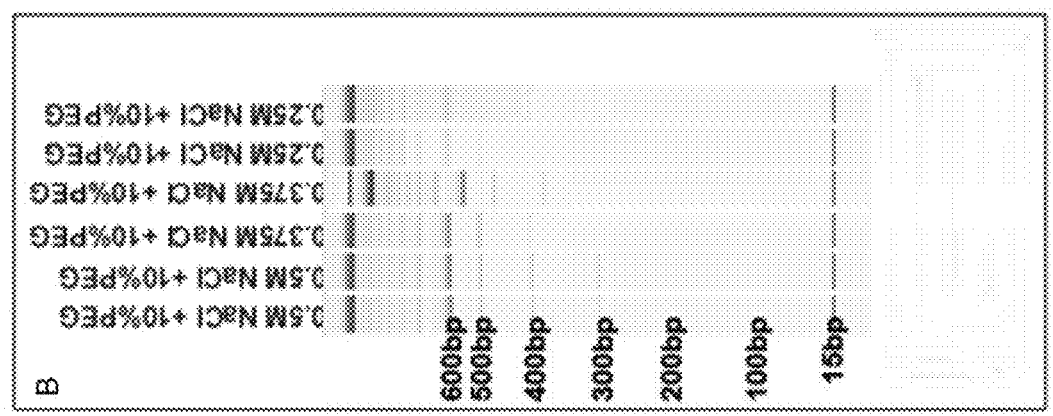
Figure 1A:
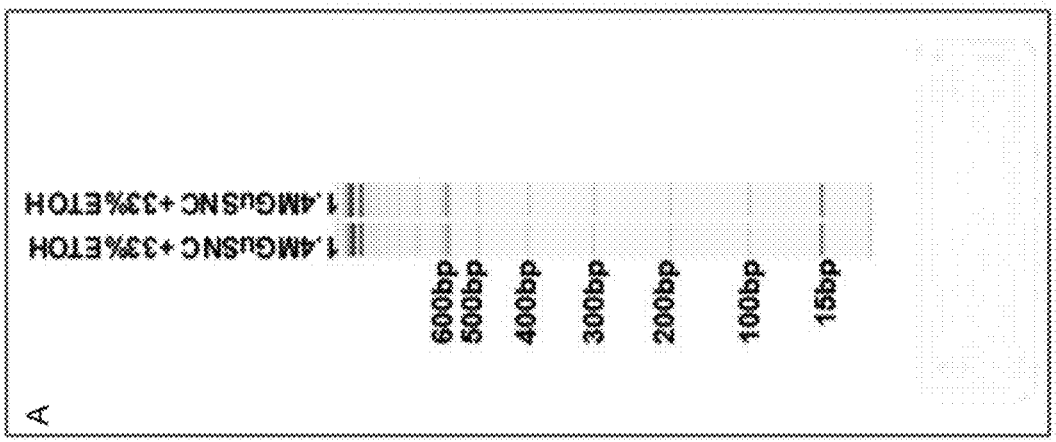

FIGS. 1A, 1B and 1C illustrate the results of size selection based DNA extraction using a 1-kilobase (kb) ladder and various salt concentrations. The DNA is first bound to a silica dioxide solid support at a high salt concentration of guanidine thiocyanate to bind all nucleic acids in a nucleic acid composition (FIG. 1A). Different salt concentrations were used to select for different sizes of nucleic acids from the beads. Nucleic acids within specific size ranges (e.g., 100 to 200 bp, 200 to 300 bp and the like) can be enriched or extracted based on the use of particular salt concentrations, as described below and presented in Table 1 (see Example 3).

To identify salt concentrations useful for eluting nucleic acids of varying sizes from the solid support beads, a titration of different salt concentrations was used to remove the smaller nucleic acid fragments of a 1-kb ladder from the beads and determine the salt concentrations at which different sized, bound, nucleic acids were eluted from the beads (FIG. 1B). This was accomplished by first binding substantially all of the nucleic acid composition (e.g., the 1-kb ladder) to the beads, then applying different salt concentrations (0.25M FIG. 1B lanes 1-2, 0.375M FIG. 1B lanes 3-4, and 0.5M NaCl FIG. 1B lanes 5-6) to the same beads to extract (e.g., elute) the smaller fragments, leaving behind the larger fragments. The larger fragments were eluted off the beads and analyzed in an Agilent BioAnalyzer. For selection of smaller size DNA fragments, the titration of different salts was performed as above (e.g., 0.25M FIG. 1C lanes 1-2, 0.375M FIG. 1C lanes 3-4, and 0.5M NaCl FIG. 1C lanes 5-6) to remove the smaller fragments from the beads. The supernatant containing the eluted fragments was removed to a new tube, contacted with new beads in the presence of a high concentration of guanidine thiocyanate chaotropic salt (e.g., binding or adsorbing), followed by extracting and concentrating the small fragments (FIG. 1C).

In some embodiments, the method can be employed to facilitate size selective separation of nucleic acid ranges useful for further analysis using many different methods, such as enrichment of fetal or disease nucleic acids from a background of maternal or healthy nucleic acids or library preparations for sequencing, for example. Figure specific methods are further described below.

FIG. 1A
1. 1 µg of 1-kb ladder was added to a final concentration of 1.4M GuSCN, 33% ETOH and sufficient silica dioxide magnetic beads to bind all of the DNA. The mixture was shaken at 800 revolutions per minute (RPM) at room temperature for 10 minutes.
2. The mixture was placed in a magnetic field and the supernatant was removed.
3. 400 µl of a 90% ETOH solution was added to the beads, placed in a magnetic field and removed twice to wash out the inhibitors.
4. The beads were allowed to air dry 5 minutes to remove the ETOH wash.
5. 10 µl of DEPC $H_2O$ was added the beads to elute the DNA.
6. 1.5 µl of the sample was run on an Agilent BioAnalyzer DNA 1000 chip.

FIG. 1B
1. 1 µg of 1-kb ladder was added to a final concentration of 1.4M GuSCN, 33% ETOH and sufficient silica dioxide magnetic beads to bind all of the DNA. The mixture was shaken at 800 revolutions per minute (RPM) at room temperature for 10 minutes.

2. The mixture was placed in a magnetic field and the supernatant was removed.
3. 400 μl of a 90% ETOH solution was added to the beads, placed in a magnetic field and removed twice to wash out the inhibitors.

Table A shows ratios of relatively small to relatively large nucleic acid eluted from the solid supports (200 bp or less and the 300 bp or less fractions), and ratios of relatively large to relatively small nucleic acid associated with solid supports (greater than 200 bp and greater than 300 bp fractions) for various dissociation conditions.

TABLE A

| Base Pairs for a 1 kb Ladder | 0.5M NaCl/10% PEG8000 | 0.375M NaCl/10% PEG8000 | 0.25M NaCl/10% PEG8000 | 0.5M NaCl/18% PEG8000 | 0.375M NaCl/18% PEG8000 | 0.25M NaCl/18% PEG8000 |
|---|---|---|---|---|---|---|
| 200 bp or less | 2.3 | 1.6 | 0.23 | 0.7 | 0.9 | 0.25 |
| >200 bp | 16 | 68 | 109 | 1.4 | 1.2 | 3.8 |
| 300 bp or less | 3.6 | 3.48 | 0.53 | 0.9 | 1 | 0.3 |
| >300 bp | 6.4 | 28 | 62 | 0.7 | 1 | 3.48 |

4. The beads were allowed to air dry 5 minutes to remove the ETOH wash.
5. The beads are added to a solution containing 10% Crowding Agent and salt at a final concentration of 0.5M, 0.375M or 0.25M NaCl, and incubated at 45° C. for 10 minutes.
6. The mixture was placed in a magnetic field and the supernatant was removed.
7. 400 μl of a 90% ETOH solution was added to the beads, placed in a magnetic field and removed twice to wash out the inhibitors.
8. The beads were allowed to air dry 5 minutes to remove the ETOH wash.
9. 10 μl of DEPC H$_2$O was added the beads to elute the DNA.
10. 1.5 μl of the sample was run on an Agilent BioAnalyzer DNA 1000 chip.

FIG. 1C
1. 1 μg of 1-kb ladder was added to a final concentration of 1.4M GuSCN, 33% ETOH and sufficient silica dioxide magnetic beads to bind all of the DNA. The mixture was shaken at 800 revolutions per minute (RPM) at room temperature for 10 minutes.
2. The mixture was placed in a magnetic field and the supernatant was removed.
3. 400 μl of a 90% ETOH solution was added to the beads, placed in a magnetic field and removed twice to wash out the inhibitors.
4. The beads were allowed to air dry 5 minutes to remove the ETOH wash.
5. The beads are added to a solution containing 10% crowding agent and salt at a final concentration of 0.5M, 0.375M or 0.25M NaCl, and incubated at 45° C. for 10 minutes.
6. The mixture was placed in a magnetic field and the supernatant was removed.
7. The supernatant was added to a solution containing a final concentration of 1.4M GuSCN and 33% ETOH and sufficient silica dioxide magnetic beads to bind all of the DNA.
8. 400 μl of a 90% ETOH solution was added to the beads, placed in a magnetic field and removed twice to wash out the inhibitors.
9. The beads were allowed to air dry 5 minutes to remove the ETOH wash.
10. 10 μl of DEPC H$_2$O was added the beads to elute the DNA.
11. 1.5 μl of the sample was run on an Agilent BioAnalyzer DNA 1000 chip.

Example 2: Isolation of DNA in a Plasma Sample

The methods and compositions provided herein can be used to selectively enrich and/or extract DNA based on its size in a maternal plasma sample (see FIG. 2). Whole blood was collected from a pregnant female and centrifuged to obtain the plasma fraction containing cell free DNA from both mother and fetus. Extracellular maternal nucleic acid ranges in size distribution from about 50 bp to about 800 bp, while fetal DNA ranges from about 50 bp to about 300 bp (Chan et al (2004) and Li et al (2004). The difference in size ranges at the upper end of the nucleic acid fragment size range, as seen between maternal and fetal nucleic acids, allows for size specific enrichment of fetal nucleic acid. The results illustrated in FIG. 2 show a 30% enrichment of a male fetal DNA from maternal DNA by selecting for sizes 300 bp, with the greatest enrichment seen 200 bp. Without enrichment, fetal DNA is 9% of the total nucleic acid isolated from maternal plasma. Enrichment was performed by using three different salt titrations 0.375M NaCl/10% PEG, 0.5M NaCl/10% PEG, and 1M NaCl/10% PEG, which selects for less than 500 base pairs, less than 400 base pairs, and less than 300 base pairs, respectively. In FIG. 2, 30% enrichment (e.g., 100%−(9%/13%)) of the male fetal DNA is achieved by selecting for 300 bp and lower.

1. Protein Denaturation and Protein Digestion

An aqueous buffer with a pH in the range of about 5 to about 8 and containing; a low concentration of chaotropic salt (e.g., less than 30% solution (weight per volume, or w/v), for example), a detergent at 5-20% w/v, 1-50 mM EDTA, and protease or proteinase k at 5-100 mg/ml was added to a blood plasma sample to denature proteins and inactivate nucleases. The solution was mixed thoroughly, and incubated according to the requirements for the chosen protein degrading enzyme (e.g., 30 minutes at 55° C., for example).

2. Binding of Nucleic Acids

The sample was contacted with a solid support (e.g., beads, for example) and adjusted to a final concentration of 1.4M GuSCN and 33% ETOH. The mixture was incubated with rotation at room temperature for 20 minutes.

3. Separation of the Solid Support from the Solution

The beads were separated from the supernatant by centrifugation or magnetic field.

4. Washing the Beads to Remove Inhibitors

The beads were resuspended in 800 μl of 90% ETOH, placed in a magnetic field and the wash solution removed. Washes were typically performed twice to ensure removal of substantially all PCR inhibitors.

5. Size Selection of Nucleic Acids Isolated from Plasma Samples

The washed beads, to which total serum DNA was bound, were resuspended in a solution containing 10% Crowding Agent and a specific salt concentration chosen according to the specific size range of nucleic acids desired. The beads were mixed thoroughly, and incubated for 10 minutes at 45° C.

6. Separation of Eluted Nucleic Acids Fragments and Binding to New Beads

The beads are placed in a magnetic field and the supernatant was collected and transferred to a new tube. The concentration of the solution was adjusted to 1.4M GuSCN and 33% ETOH to bind the eluted fragments (e.g., small fragments) contained in the supernatant solution.

7. Washing

The beads were resuspended in 800 μl of 90% ETOH, placed in a magnetic field and the wash solution removed. Washes were typically performed twice to ensure removal of substantially all PCR inhibitors. The beads with the larger fragments were also washed using the same conditions, to allow a comparison of the size ranges eluted under the various salt conditions. The larger fragments can also be analyzed further. All beads were subjected to air drying to remove any remaining alcohol that might inhibit further analysis.

8. Elution

The target nucleic acids were eluted from the solid support by addition of a sufficient quantity of sterile water or aqueous buffered solution (e.g., 1×TE pH 7-8.5). The elution can be performed at ambient temperature or by exposing to heat. The eluate was collected and prepared for further analysis

9. Analysis of the Target DNA

An aliquot of the eluted DNA is subjected to PCR using multiplexed primers and a reference target of known copy number and sequence, as listed in Table 2 (presented below in Example 4). The PCR conditions used to amplify the target nucleic acid were; 50° C. for 3 minutes, 93° C. for 10 minutes, 45 cycles of 93° C. for 5 seconds, 60° C. for 30 seconds and 72° C. for 1 minute and 15 seconds, followed by a hold at 72° C. for 10 minutes. The PCR products were analyzed with MassArray spectrometry, using qGE protocols to determine copy number ratio of male fetus Y chromosome DNA to total DNA using PLAC 4 genes and RhD loci. The data illustrates successful enrichment and extraction of small fragments containing fetal nucleic acids.

Table 1 illustrates the percent recovery of specific size fractions of nucleic acid, using specific dissociation conditions, from the total nucleic acid isolated from a substantially cell free sample.

| | Large Fragments | | | | | |
|---|---|---|---|---|---|---|
| Base Pairs for a 1 kb Ladder | 0.5M NaCl/10% PEG8000 Large Fragments | 0.375M NaCl/10% PEG8000 Large Fragments | 0.25M NaCl/10% PEG8000 Large Fragments | 0.5M NaCl/18% PEG8000 Large Fragments | 0.375M NaCl/18% PEG8000 Large Fragments | 0.25M NaCl/18% PEG8000 Large Fragments |
| 100 bp | 0% | 0% | 0% | 0% | 0% | 0% |
| 200 bp | 0% | 0% | 0% | 51% | 0% | 0% |
| 300 bp | 0% | 13% | 0% | 60% | 11% | 0% |
| 400 bp | 39% | 50% | 0% | 84% | 27% | 12% |
| 500 bp | 78% | 80% | 0% | 100% | 34% | 17% |
| 600 bp | 100% | 97% | 0% | 100% | 34% | 27% |
| 700 bp | 100% | 100% | 0% | 100% | 51% | 44% |
| 800 bp | 100% | 100% | 0% | 100% | 61% | 52% |
| 900 bp | 100% | 100% | 21% | 100% | 72% | 59% |
| 1000 bp | 100% | 100% | 35% | 100% | 80% | 65% |
| 1200 bp | 100% | 100% | 100% | 100% | 100% | 114% |
| 1300 bp | 100% | 100% | 77% | 100% | 22% | 18% |

| | Small Fragments | | | | | |
|---|---|---|---|---|---|---|
| Base Pairs for a 1 kb Ladder | 0.5M NaCl/10% PEG8000 Small Fragments | 0.375M NaCl/10% PEG8000 Small Fragments | 0.25M NaCl/10% PEG8000 Small Fragments | 0.5M NaCl/18% PEG8000 Small Fragments | 0.375M NaCl/18% PEG8000 Small Fragments | 0.25M NaCl/18% PEG8000 Small Fragments |
| 100 bp | 100% | 100% | 100% | 100% | 100% | 100% |
| 200 bp | 100% | 100% | 100% | 49% | 100% | 100% |
| 300 bp | 100% | 87% | 100% | 40% | 89% | 100% |
| 400 bp | 61% | 50% | 100% | 16% | 73% | 88% |
| 500 bp | 22% | 20% | 100% | 0% | 66% | 83% |
| 600 bp | 0% | 3% | 100% | 0% | 66% | 73% |
| 700 bp | 0% | 0% | 100% | 0% | 49% | 56% |
| 800 bp | 0% | 0% | 100% | 0% | 39% | 48% |
| 900 bp | 0% | 0% | 79% | 0% | 28% | 41% |
| 1000 bp | 0% | 0% | 65% | 0% | 20% | 35% |
| 1200 bp | 0% | 0% | 0% | 0% | 0% | 0% |
| 1300 bp | 0% | 0% | 23% | 0% | 78% | 82% |

TABLE 2 provides the sequences of oligonucleotides, and probes used to analyze the nucleic acids recovered using the methods and compositions described herein.

| SNP_ID | Forward Primers | Reverse Primers | Probe |
|---|---|---|---|
| RhD Ex4 | ACGTTGGAT GGACTATCA GGGCTTGCC CCG | ACGTTGG ATGTGCG AACACGT AGATGTG CA | cTGCAGA CAGACTA CCACATG AAC |
| RhD Ex7-D1 | ACGTTGGAT GAGCTCCAT CATGGGCTA CAAC | ACGTTGG ATGTTGC CGGCTCC GACGGTA TC | CTTGCTGG GTCTGCTT GGAGAGAT CA |
| SRY | ACGTTGGAT GAGATGGCT CTAGAGAAT CCC | ACGTTGG ATGGCAT TTTCCAC TGGTATC CC | CCAGAATG CGAAACTC |
| P4_rs8130833NE | ACGTTGGAT GTATAGAAC CATGTTTAG G | ACGTTGGA TGACCATT TGGGTTAA ATAC | TTTGGGTT AAATACAA GTTAGA |
| P4_rs4818219Cur | ACGTTGGAT GTCTGGGAC TAGTACCCA AAG | ACGTTGGA TGAAAGCC ACTGACAA GCAGAC | GGGATGGC TTGCGCAG TG |
| P4_rs8130833 Competitor | ACGTTGGAT GACCATTTG GGTTAAATA C | ACGTTGGA TGTATAGA ACCATGTT TAGG | GCATGTTT AGGCCAGA TATATTCG |
| P4_rs4818219 Competitor | ACGTTGGAT GTCTGGGAC TAGTACCCA AAG | ACGTTGGA TGAAAGCC ACTGACAA GCAGAC | CCAAAGCAC CTAGCTCTC |
| Control | ACGTTGGAT GAGTGGACT CCAGGTAAG ATG | ACGTTGGA TGGATGGC AGCCTGAA TATGTC | FCGATTCCT AGAACTGTT |
| RhD Ex5-D2 | ACGTTGGAT GAATCGAAA GGAAGAATG CCG | ACGTTGGA TGCTGAGA TGGCTGTC ACCACG | CCCGTGTTC AACACCTAC TATGCT |
| X/Y | TCGACCCGG AGCACGTTG GAACACTCC ATGACTCCA ACCC | TCGACCCG GAGCACGT TGGAGCTG GTAGGGCT GCTGGGC | CCCAGCAGC CAAACCTCC CTC |
| SRY Competitor Template | GATCAGAGG CGCAAGATG GCTCTAGAG AATCCCAGA ATGCGAAAC TCTGAGATC AGCAAGCAG CTGGGATAC CAGTGGAAA ATGCTTACT GAAGCCGA | | |
| RHD-Ex5 Competitor Template | AAGGATGAC CCTGAGATG GCTGTCACC ACGCTGACT GCTATAGCA TAGTAGGTG | | |

TABLE 2-continued provides the sequences of oligonucleotides, and probes used to analyze the nucleic acids recovered using the methods and compositions described herein.

| SNP_ID | Forward Primers | Reverse Primers | Probe |
|---|---|---|---|
| | | TTGAACACG GCATTCTTC CTTTCGATT GGACTTCTC A | |
| RHD-Ex4 Competitor | | TTCTCCAAG GACTATCAG GGCTTGCCC CGGACGACA CTCACTGCT | |

Example 3: Embodiments

Provided hereafter are certain non-limiting embodiments. Not all embodiments are sequentially labeled.

A1. A method for enriching relatively short nucleic acid from a nucleic acid composition, which comprises:
  (a) contacting nucleic acid of a nucleic acid composition with a solid phase under association conditions, wherein:
    (i) the nucleic acid of the nucleic acid composition comprises relatively short nucleic acid and relatively long nucleic acid,
    (ii) the relatively short nucleic acid is about 300 base pairs or less, and
    (iii) the relatively long nucleic acid is larger than about 300 base pairs;
    whereby the relatively short nucleic acid and the relatively long nucleic acid are associated with the solid phase;
  (b) introducing the solid phase after (a) to dissociation conditions that comprise a volume exclusion agent and a salt, wherein:
    (i) the salt is not a chaotropic salt, and
    (ii) the relatively short nucleic acid preferentially dissociates from the solid phase under the dissociation conditions as compared to the relatively long nucleic, thereby yielding dissociated nucleic acid; and
  (c) separating the dissociated nucleic acid from the solid phase, whereby the relatively short nucleic acid is enriched in the dissociated nucleic acid relative to in the nucleic acid composition.

A1.1 The method of embodiment A1, wherein the nucleic acid composition is a biological composition.

A1.2 The method of embodiment A1.1, wherein the biological composition is a substantially cell-free biological composition.

A1.3 The method of embodiment A1.1, wherein the nucleic acid is cell-free nucleic acid.

A2. The method of embodiment A1.2, wherein the substantially cell-free biological composition is from a pregnant female.

A3. The method of embodiment A2, wherein the pregnant female is in the first trimester of pregnancy.

A4. The method of any one of embodiments A1.2-A3, wherein the substantially cell-free biological composition is blood serum.

A5. The method of any one of embodiments A1.2-A3, wherein the substantially cell-free biological composition is blood plasma.

A6. The method of any one of embodiments A1.2-A3, wherein the substantially cell-free biological composition is urine.

A6.5. The method of any one of embodiments A1-A6, wherein the solid phase is a collection of particles.

A7. The method of embodiment A6.5, wherein the particles comprise silica.

A7.1. The method of embodiment A7, wherein the silica comprises silica dioxide.

A8. The method of embodiment A7 or A7.1, wherein the particles further comprise an agent that confers a paramagnetic property to the particles.

A9. The method of embodiment A8, wherein the agent comprises a metal.

A9.1. The method of embodiment A9, wherein the agent is a metal oxide.

A10. The method of any one of embodiments A1-A9.1, wherein the solid phase does not comprise a functional group that interacts with the nucleic acid.

A11. The method of embodiment A10, wherein the solid phase does not comprise a carboxy functional group.

A11.1. The method of any one of embodiments A1-A11, wherein the solid phase has a net charge.

A11.2. The method of embodiment A11.1, wherein the net charge is positive.

A11.3. The method of embodiment A11.1, wherein the net charge is negative.

A12. The method of any one of embodiments A1-A11.3, wherein the dissociated nucleic acid comprises deoxyribonucleic acid (DNA).

A13. The method of any one of embodiments A1-A12, wherein the dissociated nucleic acid comprises ribonucleic acid (RNA).

A14. The method of any one of one of embodiments A1-A12, wherein the dissociated nucleic acid consists essentially of DNA.

A15. The method of any one of embodiments A1-A11.3, wherein the dissociated nucleic acid consists essentially of RNA.

B1. The method of any one of embodiments A1-A15, wherein the association conditions comprise a C1-C6 alkyl alcohol.

B2. The method of any one of embodiments A1-A15, wherein the association conditions consist essentially of a C1-C6 alkyl alcohol.

B3. The method of any one of embodiments A1-A15, wherein the association conditions do not comprise a C1-C6 alkyl alcohol.

B4. The method of any one of embodiments B1-B3, wherein the alcohol comprises ethanol.

B5. The method of any one of embodiments A1-A15, wherein the association conditions comprise a salt.

B6. The method of any one of embodiments A1-A15, wherein the association conditions consist essentially of a salt.

B7. The method of any one of embodiments A1-A15, wherein the association conditions do not comprise a salt.

B8. The method of any one of embodiments B5-B7, wherein the salt comprises a chaotropic salt, an ionic salt or combination thereof.

B9. The method of any one of embodiments A1-A15, wherein the association conditions comprise a volume exclusion agent.

B10. The method of any one of embodiments A1-A15, wherein the association conditions consist essentially of a volume exclusion agent.

B11. The method of any one of embodiments A1-A15, wherein the association conditions do not comprise a volume exclusion agent.

B12. The method of any one of embodiments B9-B11, wherein the volume exclusion agent comprises a polyalkyl glycol, dextran, Ficoll, polyvinyl pyrollidone or combination thereof.

B13. The method of any one of embodiments A1-A15 and B1-B12, wherein the relatively short nucleic acid is about 200 base pairs or less and the relatively long nucleic acid is larger than about 200 base pairs.

B14. The method of embodiment B13, wherein the relatively short nucleic acid is about 50 to about 180 base pairs.

B15. The method of any one of embodiments A1-A15 and B1-B14, wherein about 30% to about 90% of the nucleic acid of the nucleic acid composition associates with the solid phase.

B16. The method of embodiment B15, wherein about 60% of the nucleic acid of the nucleic acid composition associates with the solid phase.

B17. The method of any one of embodiments A1-A15 and B1-B16, which further comprises washing the solid phase after (a).

B17.1. The method of embodiment B17, wherein the solid phase is washed under conditions that remove material of the nucleic acid composition not associated with the solid phase from the solid phase.

B17.2. The method of embodiment B17, wherein the solid phase is washed under conditions that dissociate any non-nucleic acid material of the nucleic acid composition from the solid phase.

C1. The method of any one of embodiments A1-A15 and B1-B17, wherein the salt comprises an ionic salt.

C2. The method of embodiment C1, wherein the ionic salt is sodium chloride.

C3. The method of embodiment C1 or C2, wherein the dissociation conditions comprise about 0.25M to about 0.5M of the ionic salt.

C4. The method of any one of embodiments A1-A15, B1-B17 and C1-C3, wherein the volume exclusion agent comprises a polyalkyl alcohol, dextran, Ficoll, polyvinyl pyrollidone or combination thereof.

C5. The method of embodiment C4, wherein the polyalkyl alcohol is polyethylene glycol (PEG).

C6. The method of embodiment C5, wherein the PEG is PEG 8000

C7. The method of embodiment C5 or C6, wherein the dissociation conditions comprise about 10% PEG.

C8. The method of any one of embodiments A1-A15, B1-B17 and C1-C7, wherein the salt and the volume exclusion agent are present in the dissociation conditions at concentrations according to Table 1.

C9. The method of any one of embodiments A1-A15, B1-B17 and C1-C8, wherein the relatively short nucleic acid preferentially dissociates from the solid phase under the dissociation conditions as compared to the relatively long nucleic acid at a ratio of about 1.05 to about 5 relatively short nucleic acid to relatively long nucleic acid.

C11. The method of any one of embodiments A1-A15, B1-B17 and C1-C10, wherein the relatively short nucleic acid is enriched about 10% to about 45% in the dissociated nucleic acid relative to in the nucleic acid composition.

C12. The method of any one of embodiments A1-A15, B1-B17 and C1-C11, wherein the solid phase is paramagnetic and the dissociated nucleic acid is separated from the solid phase by a magnet.

C13. The method of any one of embodiments A1-A15, B1-B17 and C1-C11, wherein the solid phase is separated from the dissociated nucleic acid by centrifugation.

C14. The method of any one of embodiments A1-A15, B1-B17 and C1-C13, wherein the solid phase is separated from the dissociated nucleic acid by transferring the dissociated nucleic acid to an environment that does not contain the solid phase used in (a) of embodiment A1.

C15. The method of any one of embodiments A1-A15, B1-B17 and C1-C13, wherein the solid phase is separated from the dissociated nucleic acid by transferring the solid phase to an environment that does not contain the dissociated nucleic acid.

C16. The method of embodiment C14 or C15, wherein the environment is a vessel.

C17. The method of any one of embodiments A1-A15, B1-B17 and C1-C16, which further comprises associating the dissociated nucleic acid to a second solid phase.

C18. The method of embodiment C17, which further comprises dissociating the dissociated nucleic acid from the second solid phase, thereby releasing the dissociated nucleic acid from the second solid phase.

D1. The method of any one of embodiments A1-A15, B1-B17 and C1-C18, which further comprises analyzing the dissociated nucleic acid and/or nucleic acid associated with the solid phase after (c) by mass spectrometry.

D2. The method of any one of embodiments A1-A15, B1-B17 and C1-C18, which further comprises contacting the dissociated nucleic acid and/or nucleic acid associated with the solid phase after (c) with an oligonucleotide that hybridizes to the dissociated nucleic acid and is extended under extension conditions, thereby yielding extended oligonucleotide.

D3. The method of any one of embodiments A1-A15, B1-B17 and C1-C18, which further comprises amplifying the dissociated nucleic acid and/or the nucleic acid associated with the solid phase after (c), thereby yielding amplified product.

D4. The method of embodiment D3, which further comprises contacting the amplified product with an oligonucleotide that hybridizes to the amplified product and is extended under extension conditions, thereby yielding extended oligonucleotide.

D5. The method of any one of embodiments D2-D4, which further comprises analyzing the extended oligonucleotide or the amplified product.

D6. The method of embodiment D5, wherein the extended oligonucleotide or the amplified product is analyzed by mass spectrometry.

D7. The method of any one of embodiments A1-A15, B1-B17, C1-C18 and D1-D6, which further comprises detecting the presence or absence of fetal nucleic acid.

D8. The method of embodiment D7, which comprises detecting the presence or absence of a fetal-specific nucleotide sequence.

D9. The method of embodiment D8, wherein the fetal-specific nucleotide sequence is a Y-chromosome sequence.

D10. The method of embodiment D8, wherein the fetal-specific nucleotide sequence is a mRNA sequence.

D11. The method of any one of embodiments A1-A15, B1-B17, C1-C18 and D1-D10, which further comprises detecting the presence or absence of a prenatal disorder.

D12. The method of embodiment D11, wherein the prenatal disorder is a chromosome abnormality.

D13. The method of embodiment D12, wherein the chromosome abnormality is a trisomy.

D14. The method of embodiment D13, wherein the trisomy is trisomy 21, trisomy 18, trisomy 13 or combination thereof.

D15. The method of any one of embodiments A1-A15, B1-B17, C1-C18 and D1-D14, which further comprises detecting the presence or absence of a cell proliferation disorder.

D16. The method of embodiment D15, wherein the cell proliferation disorder is a cancer.

The entirety of each patent, patent application, publication and document referenced herein hereby is incorporated by reference. Citation of the above patents, patent applications, publications and documents is not an admission that any of the foregoing is pertinent prior art, nor does it constitute any admission as to the contents or date of these publications or documents.

Modifications may be made to the foregoing without departing from the basic aspects of the technology. Although the technology has been described in substantial detail with reference to one or more specific embodiments, those of ordinary skill in the art will recognize that changes may be made to the embodiments specifically disclosed in this application, yet these modifications and improvements are within the scope and spirit of the technology.

The technology illustratively described herein suitably may be practiced in the absence of any element(s) not specifically disclosed herein. Thus, for example, in each instance herein any of the terms "comprising," "consisting essentially of," and "consisting of" may be replaced with either of the other two terms. The terms and expressions which have been employed are used as terms of description and not of limitation, and use of such terms and expressions do not exclude any equivalents of the features shown and described or portions thereof, and various modifications are possible within the scope of the claimed technology. The term "a" or "an" can refer to one of or a plurality of the elements it modifies (e.g., "a reagent" can mean one or more reagents) unless it is contextually clear either one of the elements or more than one of the elements is described. The term "about" as used herein refers to a value within 10% of the underlying parameter (i.e., plus or minus 10%), and use of the term "about" at the beginning of a string of values modifies each of the values (i.e., "about 1, 2 and 3" refers to about 1, about 2 and about 3). For example, a weight of "about 100 grams" can include weights between 90 grams and 110 grams. Further, when a listing of values is described herein (e.g., about 50%, 60%, 70%, 80%, 85% or 86%) the listing includes all intermediate and fractional values thereof (e.g., 54%, 85.4%). Thus, it should be understood that although the present technology has been specifically disclosed by representative embodiments and optional features, modification and variation of the concepts herein disclosed may be resorted to by those skilled in the art, and such modifications and variations are considered within the scope of this technology.

Certain embodiments of the technology are set forth in the claim(s) that follow(s).

What is claimed is:

1. A method for enriching short nucleic acid from a nucleic acid composition, which comprises:
   (a) contacting cell-free nucleic acid from a substantially cell-free biological composition with a solid phase under an association condition, wherein:
      (i) the cell-free nucleic acid comprises short nucleic acid and long nucleic acid,
      (ii) the short nucleic acid is 200 base pairs or less,
      (iii) the long nucleic acid is larger than 200 base pairs,
      (iv) the association condition comprises a salt, and
      (v) the association condition does not include polyethylene glycol (PEG), whereby the short nucleic acid and the long nucleic acid associate with the solid phase;
   (b) introducing the solid phase from (a) to a dissociation condition that comprises a volume exclusion agent and/or a salt, wherein:
      (i) the salt is not a chaotropic salt,
      (ii) the short nucleic acid dissociates from the solid phase under the dissociation condition, thereby yielding dissociated nucleic acid, and
      (iii) the volume exclusion agent comprises a polyalkyl glycol, dextran, ficoll, polyvinyl pyrrolidone, or combination thereof; and
   (c) separating the dissociated nucleic acid from the solid phase by transferring the dissociated nucleic acid to a vessel that does not contain the solid phase used in (b) or by transferring the solid phase used in (b) to a vessel that does not contain the dissociated nucleic acid, thereby enriching the short nucleic acid relative to the long nucleic acid in the dissociated nucleic acid compared to the cell-free nucleic acid in (a).

2. The method of claim 1, wherein the substantially cell-free biological composition is from a pregnant female.

3. The method of claim 1, wherein the substantially cell-free biological composition is blood serum.

4. The method of claim 1, wherein the substantially cell-free biological composition is blood plasma.

5. The method of claim 1, wherein the substantially cell-free biological composition is urine.

6. The method of claim 1, wherein the solid phase is a collection of particles.

7. The method of claim 6, wherein the particles comprise silica.

8. The method of claim 1, wherein the solid phase does not comprise a functional group that interacts with the nucleic acid.

9. The method of claim 1, wherein the solid phase has a net charge.

10. The method of claim 1, wherein the salt in (b) comprises an ionic salt.

11. The method of claim 10, wherein the ionic salt is sodium chloride.

12. The method of claim 1, wherein the short nucleic acid is about 50 to about 180 base pairs.

13. The method of claim 1, wherein the short nucleic acid is about 160 base pairs or less.

14. The method of claim 1, which further comprises washing the solid phase after (a).

15. The method of claim 1, wherein the solid phase is paramagnetic, and (c) further comprises separating the dissociated nucleic acid from the solid phase by a magnet.

16. The method of claim 1, wherein the short nucleic acid is enriched about 10% to about 45% in the dissociated nucleic acid relative to the cell-free nucleic acid in (a).

17. The method of claim 1, wherein (c) further comprises separating the dissociated nucleic acid from the solid phase by centrifugation.

18. The method of claim 1, wherein the salt in (a) is a chaotropic salt.

19. The method of claim 18, wherein the chaotropic salt is a guanidine salt.

* * * * *

```
                            SEQUENCE LISTING

<160> NUMBER OF SEQ ID NOS: 36

<210> SEQ ID NO 1
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
acgttggatg gactatcagg gcttgccccg                                          30

<210> SEQ ID NO 2
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
acgttggatg agctccatca tgggctacaa c                                        31

<210> SEQ ID NO 3
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
acgttggatg agatggctct agagaatccc                                          30

<210> SEQ ID NO 4
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
acgttggatg tatagaacca tgtttagg                                            28

<210> SEQ ID NO 5
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
acgttggatg tctgggacta gtacccaaag                                          30

<210> SEQ ID NO 6
<211> LENGTH: 28
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 6
acgttggatg accatttggg ttaaatac                                         28

<210> SEQ ID NO 7
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
acgttggatg tctgggacta gtacccaaag                                       30

<210> SEQ ID NO 8
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
acgttggatg agtggactcc aggtaagatg                                       30

<210> SEQ ID NO 9
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
acgttggatg aatcgaaagg aagaatgccg                                       30

<210> SEQ ID NO 10
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
tcgacccgga gcacgttgga acactccatg actccaaccc                            40

<210> SEQ ID NO 11
<211> LENGTH: 98
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
gatcagaggc gcaagatggc tctagagaat cccagaatgc gaaactctga gatcagcaag      60
cagctgggat accagtggaa aatgcttact gaagccga                              98

<210> SEQ ID NO 12
<211> LENGTH: 91
<212> TYPE: DNA
<213> ORGANISM: Artificial Sequence
<220> FEATURE:
<223> OTHER INFORMATION: Description of Artificial Sequence: Synthetic
      primer
```

<400> SEQUENCE: 12
aaggatgacc ctgagatggc tgtcaccacg ctgactgcta tagcatagta ggtgttgaac    60
acggcattct tcctttcgat tggacttctc a                                   91

<210> SEQ ID NO 13
<211> LENGTH: 108
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
ttctccaagg actatcaggg cttgccccgg acgacactca ctgctcttac tgggttttat    60
tgcagacaga ctaccacatg aacgtgatgc acatctacgt gttcgcag                108

<210> SEQ ID NO 14
<211> LENGTH: 108
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
attccccaca gctccatcat gggctacaac tagcttgctg ggtctgcttg gagagatcaa    60
ctttgtgctg ctggtgcttg ataccgtcgg agccggcaat ggcatgtg               108

<210> SEQ ID NO 15
<211> LENGTH: 67
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
aacaccattt gggttaaata cacaagtctt gtcgaatata tctggcctaa acatggttct    60
atatact                                                              67

<210> SEQ ID NO 16
<211> LENGTH: 79
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
agaaaagcca ctgacaagca gacagaatac tactgtcaat ataggagagc taggtgcttt    60
gggtactagt cccagagct                                                 79

<210> SEQ ID NO 17
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
acgttggatg tgcgaacacg tagatgtgca                                     30

<210> SEQ ID NO 18
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
acgttggatg ttgccggctc cgacggtatc                                30

<210> SEQ ID NO 19
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
acgttggatg gcattttcca ctggtatccc                                30

<210> SEQ ID NO 20
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
acgttggatg accatttggg ttaaatac                                  28

<210> SEQ ID NO 21
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
acgttggatg aaagccactg acaagcagac                                30

<210> SEQ ID NO 22
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
acgttggatg tatagaacca tgtttagg                                  28

<210> SEQ ID NO 23
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
acgttggatg aaagccactg acaagcagac                                30

```
<210> SEQ ID NO 24
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
acgttggatg gatggcagcc tgaatatgtc                                          30

<210> SEQ ID NO 25
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
acgttggatg ctgagatggc tgtcaccacg                                          30

<210> SEQ ID NO 26
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
tcgacccgga gcacgttgga gctggtaggg ctgctgggc                                39

<210> SEQ ID NO 27
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 27
ctgcagacag actaccacat gaac                                                24

<210> SEQ ID NO 28
<211> LENGTH: 26
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 28
cttgctgggt ctgcttggag agatca                                              26

<210> SEQ ID NO 29
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 29
ccagaatgcg aaactc                                                         16
```

```
<210> SEQ ID NO 30
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 30
tttgggttaa atacaagtta ga                                            22

<210> SEQ ID NO 31
<211> LENGTH: 18
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 31
gggatggctt gcgcagtg                                                 18

<210> SEQ ID NO 32
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 32
gcatgtttag gccagatata ttcg                                          24

<210> SEQ ID NO 33
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 33
ccaaagcacc tagctctcc                                                19

<210> SEQ ID NO 34
<211> LENGTH: 18
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 34
tcgattccta gaactgtt                                                 18

<210> SEQ ID NO 35
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 35
cccgtgttca acacctacta tgct                                          24

<210> SEQ ID NO 36
```

```
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 36
cccagcagcc aaacctccct c                                              21
```